United States Patent [19]

Ogura et al.

[11] Patent Number: 4,837,217
[45] Date of Patent: Jun. 6, 1989

[54] PYRIDAZINONE DERIVATIVES, PREPARATION THEREOF, AND INSECTICIDAL, ACARICIDAL, NEMATICIDAL, FUNGICIDAL COMPOSITIONS

[75] Inventors: Tomoyuki Ogura; Yasuo Kawamura; Masatoshi Baba, all of Funabashi, Japan; Shigeru Ishii, East Lansing, Mich.; Kiminori Hirata, Shiraoka, Japan; Masaki Kudo, Shiraoka, Japan; Yoshinori Ochiai, Shiraoka, Japan; Masayoshi Hirose, Tokyo, Japan

[73] Assignee: Nissan Chemical Industries, Ltd., Tokyo, Japan

[21] Appl. No.: 850,533

[22] Filed: Apr. 11, 1986

[30] Foreign Application Priority Data

Apr. 19, 1985 [JP] Japan ................... 60-82297
Mar. 7, 1986 [JP] Japan ................... 61-50859

[51] Int. Cl.⁴ ............... C07D 401/12; C07D 403/12; C07D 405/12; C07D 409/12
[52] U.S. Cl. ................... 514/252; 544/238; 544/240; 544/241
[58] Field of Search ............ 544/240, 241, 238; 514/252

[56] References Cited

U.S. PATENT DOCUMENTS

| | | | |
|---|---|---|---|
| 2,832,780 | 4/1958 | King | 544/239 |
| 3,137,696 | 6/1964 | Reicheneder et al. | 544/240 |
| 3,346,577 | 10/1967 | Nakagome et al. | 544/239 |
| 4,177,273 | 12/1979 | Bennett | 544/240 |
| 4,571,397 | 2/1986 | Taniguchi et al. | 71/92 |
| 4,576,630 | 3/1986 | Parg et al. | 71/92 |
| 4,663,324 | 5/1987 | Graf et al. | 514/247 |
| 4,783,462 | 11/1988 | Mutsukado | 544/238 |

FOREIGN PATENT DOCUMENTS

| | | |
|---|---|---|
| 78450 | 5/1983 | European Pat. Off. |
| 0088384 | 9/1983 | European Pat. Off. |
| 0134439 | 6/1984 | European Pat. Off. |
| 135076 | 3/1985 | European Pat. Off. |
| 183212 | 6/1986 | European Pat. Off. |
| 0193853 | 9/1986 | European Pat. Off. |
| 199281 | 10/1986 | European Pat. Off. |
| 3143303 | 5/1983 | Fed. Rep. of Germany |
| 3328770 | 2/1985 | Fed. Rep. of Germany |
| 0225039 | 7/1985 | German Democratic Rep. |
| 41-2459 | 2/1966 | Japan |
| 41-2788 | 2/1966 | Japan |
| 42-1302 | 1/1967 | Japan |
| 43-11902 | 5/1968 | Japan |
| 43-11903 | 5/1968 | Japan |
| 43-11904 | 5/1968 | Japan |
| 43-11905 | 5/1968 | Japan |
| 43-11906 | 5/1968 | Japan |
| 43-11907 | 5/1968 | Japan |
| 43-11908 | 5/1968 | Japan |
| 43-11909 | 5/1968 | Japan |
| 44-8857 | 4/1969 | Japan |
| 44-8858 | 4/1969 | Japan |
| 44-8859 | 4/1969 | Japan |
| 44-8861 | 4/1969 | Japan |
| 44-12421 | 6/1969 | Japan |
| 61-130275 | 6/1986 | Japan |
| 61-243078 | 10/1986 | Japan |
| 61-268672 | 11/1986 | Japan |

OTHER PUBLICATIONS

Kaju, Chem. Abs. 70, 28883j (1967).
Japanese Patent Abstract of Laid-Open Appln. JP 60-4173, May 16, 1985, vol. 9, No. 112 (c-281) (1835).
Japanese Patent Abstract of Laid-Open Appln. JP 60-54319, Jul. 30, 1985, vol. 9, No. 184 (c-294) (1907).
Oymer Chemical Abstract No. 114552g, vol. 93, 1980.
Wilson Chemical Abstract No. 20533h, vol. 91, 1979.
Beska Chemical Abstract No. 124615j, vol. 78, 1972.
Kaji, Chem. Abs. 69106728h (1968).
Taniguchi Chemical Abstract No. 34565m, vol. 100, 1984.
Kaji Chemical Abstract No. 30484u, vol. 71, 1969.
Kaji Chemical Abstract No. 106728h, vol. 69, 1968.

Primary Examiner—Mark L. Berch
Attorney, Agent, or Firm—Oliff & Berridge

[57] ABSTRACT

A 3(2H)-pyridazinone derivative of the general formula (I):

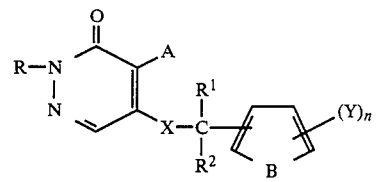

wherein
R is a straight or branched $C_2$-$C_6$ alkyl,
A is a straight or branched $C_1$-$C_6$ alkyl or a halogen atom,
X is —O— or —S—,
$R^1$ and $R^2$ are each independently hydrogen atom or $C_1$-$C_3$ alkyl,
B is —CH=CH—, —N=CH—, —N=N—, —S—, —O— or

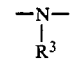

wherein $R^3$ is hydrogen or $C_1$-$C_3$ alkyl,
Y is a halogen atom, a straight or branched $C_1$-$C_6$ alkyl, a $C_3$-$C_6$ cycloalkyl or cycloalkoxy, and other substituents,
n is 0 or an integer of 1 to 3, and when n is 2 or 3, Y may be same or different, with the proviso that when B is —CH=CH—, n is an integer of 1 to 3 and at least one of Y is —O—W, as this term is defined in the specification.

A process for the preparation of said derivatives is also provided. These derivatives are useful as an active ingredient of insecticidal, acaricidal, nematicidal and/or fungicidal compositions for agricultural and horticultural uses as well as of expellent compositions for ticks parasitic on animals.

4 Claims, No Drawings

PYRIDAZINONE DERIVATIVES, PREPARATION THEREOF, AND INSECTICIDAL, ACARICIDAL, NEMATICIDAL, FUNGICIDAL COMPOSITIONS

BACKGROUND OF THE INVENTION (1) Field of the Invention

This invention relates to novel 3(2H)-pyridazinone derivatives; preparation thereof; insecticidal, acaricidal, nematicidal, fungicidal compositions for agricultural and horticultural uses; and expellent compositions for ticks parasitic on animals; said compositions containing said derivatives as an active ingredient.

(2) Description of the Prior Art:

The present inventors have previously found a part of the 3(2H)-pyridazinone derivatives represented by the following formula (IV) exhibits agricultural and horticultural insecticidal, acaricidal, nematicidal, fungicidal action (refer to European Laid-Open Patent Application Nos. 0088384 and 0134439):

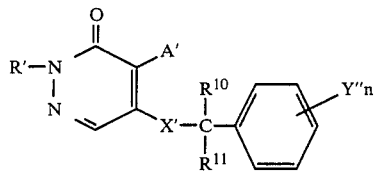

(wherein, for example, R' denotes an alkyl; A' denotes a halogen; $R^{10}$ and $R^{11}$ denote hydrogen atom or a lower alkyl; X' denotes oxygen or sulfur atom; and Y" denotes a lower alkyl, a cycloalkyl, a lower alkoxy, a lower haloalkyl, a lower haloalkoxy or a substituted phenyl).

The present inventors have further conducted researches on pyridazinone derivatives and have found that the compounds of the present invention represented by the general formula (I) given below have an excellent insecticidal, acaricidal, nematicidal and/or fungicidal action. For example, with respect to fungicidal action, the compounds represented by the general formula (IV) are effective against powdery mildew and downy mildew whereas the compounds of the present invention exhibit a strong action against red rust, rice blight and the like in addition to the above mentioned diseases, which clearly shows a wider fungicidal spectrum of the present compounds. Moreover, it was found that the compounds of the present invention have a higher activity than the known compounds represented by the formula (IV) and can effectively contol organisms which are agriculturally and horticulturally harmful even with an extremely low drug concentration. Thus, the present inventors have completed the present invention. These effects are clearly shown by the test examples given below.

SUMMARY OF THE INVENTION

The primary object of the present invention is to offer a 3(2H)-pyridazinone derivative of the general formula (I):

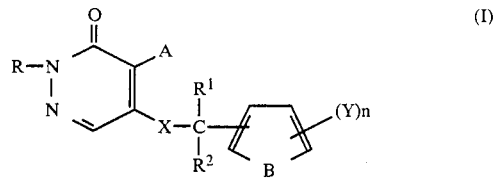

wherein
R represents a straight or branched chain alkyl having 2 to 6 carbon atoms,
A represents a straight or branched chain alkyl having 1 to 6 carbon atoms or a halogen atom,
X represents —O— or —S—,
$R^1$ and $R^2$ independently of one another represent hydrogen atom or an alkyl having 1 to 3 carbon atoms,
B represents —CH=CH—, —N=CH—, —N=N—, —S—, —O— or

wherein $R^3$ represents hydrogen or an alkyl having 1 to 3 carbon atoms,
Y represents halogen atom, a straight or branched chain alkyl having 1 to 6 carbon atoms, a cycloalkyl or cycloalkoxy having 3 to 6 carbon atoms; a straight or branched chain alkoxy or alkylthio having 1 to 6 carbon atoms; a straight or branched chain alkylsulfinyl or alkylsulfonyl having 1 to 6 carbon atoms; a haloalkyl or haloalkoxy having 1 to 4 carbon atoms; a haloalkylthio having 1 to 4 carbon atoms, an alkenyloxy having 2 to 4 carbon atoms, trimethylsilyl, an alkoxylcarbonyl having 1 to 4 carbon atoms, dimethylamino, nitro, cyano,

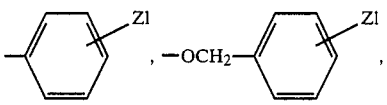

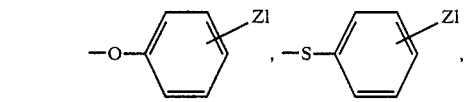

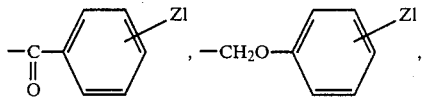

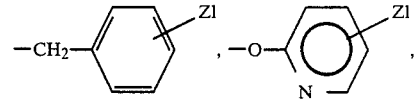

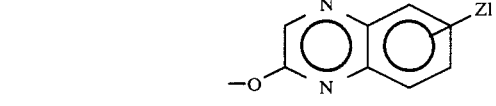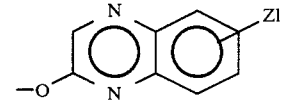

wherein
Z represents a halogen atom, a straight or branched chain alkyl or alkoxy having 1 to 6 carbon atoms, a cycloalkyl having 3 to 6 carbon atoms, a haloalkyl having 1 to 4 carbon atoms, an alkoxycarbonyl having 1 to 4 carbon atoms or nitro, l is 0 or an integer of 1 to 5, and when l is a number of 2 to 5, Z may be same or different, or Y represents —O—W, W represents a group of the formula:

$$-\overset{R^4}{\underset{R^5}{C}}-(\overset{R^6}{\underset{R^7}{C}})_m-E-R^8$$

in which $R^4$, $R^5$ and $R^6$ independently from each other represent hydrogen atom or an alkyl having 1 to 4 carbon atoms, $R^7$ represents hydrogen atom or an alkyl or alkoxyl having 1 to 3 carbon atoms, $R^8$ represents a straight or branched chain alkyl having 1 to 6 carbon atoms, a cycloalkyl having 3 to 6 carbon atoms or an alkenyl or alkynyl having 3 to 6 carbon atoms, E represents —O—, —S—, —SO—, —SO$_2$—, $$-O-\underset{\underset{O}{\|}}{C}- \text{ or } -\underset{R^9}{N}-,$$

wherein $R^9$ represents a straight or branched chain alkyl having 1 to 4 carbon atoms, or $R^8$ and $R^9$ together may form 5- or 6-membered ring. m is 0 or an integer of 1 to 3, n is 0 or an integer of 1 to 3, and when n is 2 or 3, Y may be the same or different, with the proviso that when B is —CH=CH—, n is an integer of 1 to 3 and at least one of Y is —O—W.

Another object of the present invention is to offer a process for producing said 3(2H)-pyridazinone derivative of the general formula (I).

Further object of the invention is to offer insecticidal, acaricidal, nematicidal and fungicidal compositions for agricultural and horticultural uses and expellent compositions for ticks parasitic on animals, which contain as active substances one or more of the 3(2H)-pyridazinone derivatives of the general formula (I).

A still further object of this invention is to provide a method for insecticidal, acaricidal, and/or fungicidal treatment in the agricultural and horiticultural field with the effective amount of a compound of the formula (I).

DETAILED DESCRIPTION OF THE INVENTION

Among the compounds of the present invention, following compounds are preferable in respect to the above-mentioned pest control activities.

Compounds of the general formula (IA):

(IA)

wherein R, A, X, $R^1$, $R^2$ and Y have the same meanings as given in formula (I), and n represents an integer of 1 to 3 and at least one of Y represents —O—W, in which W have the meaning as given before.

More preferable compounds are those of the general formula (IB):

(IB)

wherein

A represents a halogen or CH$_3$,

X represents O or S, $R^1$ represents hydrogen, $R^2$ represents hydrogen or CH$_3$, G represents a straight or branched chain alkylene having 1 to 6 carbon atoms, Q represents a straight or branched chain alkyl having 1 to 6 carbon atoms, and q is 1 or 2.

Another preferable compounds are those of the general formula (IC):

(IC)

wherein R, A, X, $R^1$, $R^2$ and Y have the same meanings as given in formula (I), n is 0 or an integer of 1 to 3, and B represents —N=CH—, —N=N—, —S—, —O—, or $$-\underset{R^3}{N}-.$$

Preferable compounds among those of the general formula (IC) are compounds of the general formula (ID):

(ID)

wherein

A represents a halogen or CH$_3$,

X represents O or S, $R^1$ represents hydrogen, $R^2$ represents hydrogen or CH$_3$, U represents a straight or branched chain alkyl having 1 to 6 carbon atoms, in which Hal represents a halogen atom, or a haloalkyl having 1 to 5 carbon atoms or a group of the formula —G—O—Q)$_q$, wherein G, Q and q have the same meanings as mentioned above.

Among others, more preferable compounds are those of the general formula (IE):

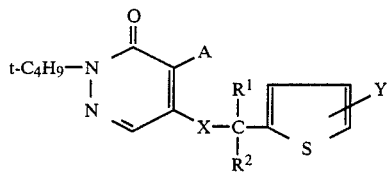

(IE)

wherein
A represents a halogen or CH$_3$,
X represents O or S,
R$^1$ represents hydrogen,
R$^2$ represents hydrogen or CH$_3$, and
Y represents a straight or branched chain alkyl having 1 to 6 carbon atoms or a straight or branched chain alkoxy having 1 to 6 carbon atoms.

Specific compounds included in the present invention are, for example, those listed in Tables 1 and 2. The compounds in Tables 1 and 2 are exemplified only for illustrating, but not limiting the present invention.

[In Tables 1 and 2, each symbol Me, Et, Pro, Bu, Pen and Hex means methyl, ethyl, propyl, butyl, pentyl and hexyl, respectively, and t, s and i means tertiary, secondary and iso, respectively].

Among the compounds exemplified in Tables 1 and 2, following compounds are preferred in respect to the pest control activity.

Nos. 7, 15, 45, 68, 71, 81, 403, 415, 424, 504, 511, 513, 517, 521, 524, 527, 533, 535, 538, 553, 554, 555, 582, 612, 616, 661, 664, 667, 671, 675, 844, 857, 872, 997, 998, 999, 1001, 1003, 1004, 1010, 1011, 1042, 1063, 1067, 1081, 1083, 1093, 1055, 1062, 1072 and 1073.

Especially preferable compounds are Nos. 45, 68, 71, 81, 403, 415, 504, 511, 513, 517, 521, 524, 527, 538, 555, 582, 612, 661, 664, 667, 671, 844, 997, 998, 1001, 1003, 1004 1081, 1083, 1062, 1063 and 1072.

In case of the compounds containing asymmetric carbon atoms, optical isomers, i.e. (+)-isomers and (−)-isomers are also included in the present invention.

The compound number in Tables 1 and 2 is referred to also in the production examples, the formulation examples and the test examples, which will be mentioned below.

TABLE 1

| No. | R | A | X | R$^1$ | O—C(R$^4$)(R$^5$)—(C(R$^6$)(R$^7$))$_m$ | ER$^8$ | (Y)$_{n-1}$ | M.P. (°C.) |
|---|---|---|---|---|---|---|---|---|
| 1 | Et | Cl | O | H | 4-OCH$_2$ | OMe | H | |
| 2 | Et | Br | O | H | 4-OCH$_2$ | OMe | H | 104.0~106.0 |
| 3 | i-Pro | Cl | O | H | 4-OCH$_2$ | OMe | H | |
| 4 | t-Bu | Me | O | H | 4-OCH$_2$ | OMe | H | |
| 5 | t-Bu | Cl | O | H | 4-OCH$_2$ | OMe | H | 70.0~73.0 |
| 6 | t-Bu | Br | O | H | 4-OCH$_2$ | OMe | H | |
| 7 | t-Bu | Cl | S | H | 4-OCH$_2$ | OMe | H | 50.0~54.0 |
| 8 | t-Bu | Br | S | H | 4-OCH$_2$ | OMe | H | |
| 9 | Hex | Cl | S | H | 4-OCH$_2$ | OMe | H | |
| 10 | i-Pro | Cl | O | H | 4-OCH$_2$ | OEt | H | |
| 11 | i-Pro | Br | O | H | 4-OCH$_2$ | OEt | H | |
| 12 | s-Bu | Cl | O | H | 4-OCH$_2$ | OEt | H | |
| 13 | t-Bu | Me | S | H | 4-OCH$_2$ | OEt | H | |
| 14 | t-Bu | Me | O | H | 4-OCH$_2$ | OEt | H | Oil |
| 15 | t-Bu | Cl | S | H | 4-OCH$_2$ | OEt | H | Oil |
| 16 | t-Bu | Br | O | H | 4-OCH$_2$ | OEt | H | Oil |
| 17 | t-Bu | Cl | O | H | 4-OCH$_2$ | OEt | H | Oil |
| 18 | t-Bu | Cl | O | H | 3-OCH$_2$ | OEt | H | |
| 19 | t-Bu | Br | O | H | 3-OCH$_2$ | OEt | H | |
| 20 | Pen | Cl | O | H | 4-OCH$_2$ | OEt | H | |
| 21 | Et | Cl | O | H | 4-OCH$_2$ | OPro | H | |
| 22 | t-Bu | Cl | O | H | 4-OCH$_2$ | OPro | H | |
| 23 | t-Bu | Br | O | H | 4-OCH$_2$ | OPro | H | |
| 24 | t-Bu | Cl | S | H | 4-OCH$_2$ | OPro | H | |
| 25 | t-Bu | Cl | O | H | 3-OCH$_2$ | OPro | H | |
| 26 | t-Bu | Me | O | H | 4-OCH$_2$ | OPro | H | |
| 27 | Et | Cl | O | H | 4-OCH$_2$ | OBu | H | |
| 28 | Et | Br | O | H | 4-OcH$_2$ | OBu | H | |
| 29 | i-Pro | Cl | O | H | 4-OCH$_2$ | OBu | H | |
| 30 | t-Bu | Me | S | H | 4-OCH$_2$ | OBu | H | |
| 31 | t-Bu | Cl | O | H | 4-OCH$_2$ | OBu | H | |
| 32 | t-Bu | Cl | S | H | 4-OCH$_2$ | OBu | H | |
| 33 | t-Bu | Br | O | H | 4-OCH$_2$ | OBu | H | |
| 34 | t-Bu | Cl | O | H | 3-OCH$_2$ | OBu | H | |
| 35 | t-Bu | Br | O | H | 3-OCH$_2$ | OBu | H | |
| 36 | t-Bu | Cl | S | H | 3-OCH$_2$ | OBu | H | |

TABLE 1-continued

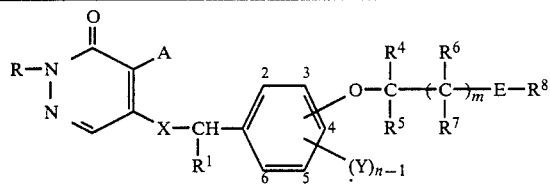

| No. | R | A | X | R¹ | O-C(R⁴)(R⁵)-(C(R⁶)(R⁷))ₘ | ER⁸ | (Y)ₙ₋₁ | M.P. (°C.) |
|---|---|---|---|---|---|---|---|---|
| 37 | Et | Cl | O | H | 4-OC₂H₄ | OMe | H | 86.7~88.4 |
| 38 | Et | Cl | S | H | 4-OC₂H₄ | OMe | 3-F | |
| 39 | t-Bu | Me | O | H | 4-OC₂H₄ | OMe | H | |
| 40 | t-Bu | Me | O | Me | 4-OC₂H₄ | OMe | H | |
| 41 | t-Bu | Me | S | H | 4-OC₂H₄ | OMe | H | |
| 42 | Pro | Cl | O | H | 4-OC₂H₄ | OMe | H | 84.6~85.7 |
| 43 | i-Pro | Cl | O | H | 4-OC₂H₄ | OMe | H | 102.0~104.0 |
| 44 | t-Bu | Cl | O | H | 4-OC₂H₄ | OMe | H | 93.5~94.3 |
| 45 | t-Bu | Cl | S | H | 4-OC₂H₄ | OMe | H | 105.6~107.3 |
| 46 | t-Bu | Cl | S | Me | 4-OC₂H₄ | OMe | H | |
| 47 | t-Bu | Cl | S | H | 4-OC₂H₄ | OMe | 3-Me | |
| 48 | t-Bu | Me | S | H | 4-OCH(CH₃)CH₂ | OMe | H | |
| 49 | t-Bu | Me | O | H | 4-OCH(CH₃)CH₂ | OMe | H | |
| 50 | t-Bu | Cl | O | H | 3-OC₂H₄ | OMe | H | |
| 51 | t-Bu | Cl | S | H | 3-OC₂H₄ | OMe | H | |
| 52 | Bu | Cl | O | H | 4-OC₂H₄ | OCH(CH₃)CH=CH₂ | H | |
| 53 | t-Bu | Cl | O | H | 4-OC₂H₄ | OCH(CH₃)CH=CH₂ | H | |
| 54 | t-Bu | Cl | S | H | 4-OC₂H₄ | OCH(CH₃)CH=CH₂ | H | |
| 55 | t-Bu | Me | O | H | 4-OCH(CH₃)CH₂ | OCH(CH₃)CH=CH₂ | H | |
| 56 | t-Bu | Me | O | H | 4-OC₂H₄ | OCH(CH₃)CH=CH₂ | H | |
| 57 | t-Bu | Cl | O | H | 4-OC₂H₄ | OCH₂CH=C(CH₃)₂ | H | |
| 58 | t-Bu | Bu | O | H | 4-OC₂H₄ | OCH₂CH=C(CH₃)₂ | H | |
| 59 | t-Bu | Cl | S | H | 4-OC₂H₄ | OCH₂CH=C(CH₃)₂ | H | |
| 60 | t-Bu | Me | O | H | 4-OCH(CH₃)CH₂ | OCH₂CH=C(CH₃)₂ | H | |
| 61 | t-Bu | Me | O | H | 4-OC₂H₄ | OCH₂CH=C(CH₃)₂ | H | |
| 62 | t-Bu | Cl | O | H | 2-OC₂H₄ | OMe | H | |
| 63 | t-Bu | Cl | O | H | 3-OC₂H₄ | OEt | H | |
| 64 | t-Bu | Me | S | H | 4-OC₂H₄ | OEt | H | |
| 65 | t-Bu | Me | O | H | 4-OC₂H₄ | OEt | H | |
| 66 | Et | Cl | O | H | 4-OC₂H₄ | OEt | H | |
| 67 | t-Bu | Cl | S | H | 4-OCH(Me)CH₂ | OEt | 3-Et | |
| 68 | t-Bu | Cl | S | H | 4-OC₂H₄ | OEt | H | 50.5~52.0 |

TABLE 1-continued

| No. | R | A | X | R¹ | O–C(R⁴)(R⁵)–(C(R⁶)(R⁷))ₘ | ER⁸ | (Y)ₙ₋₁ | M.P. (°C.) |
|---|---|---|---|---|---|---|---|---|
| 69 | t-Bu | Cl | S | H | 4-OCH(Me)CH₂ | OEt | 3-Pro—i | |
| 70 | t-Bu | Me | S | H | 4-OCH(CH₃)CH₂ | OEt | H | |
| 71 | t-Bu | Cl | O | H | 4-OC₂H₄ | OEt | H | 82.0~83.0 |
| 72 | t-Bu | Me | O | H | 4-OCH(CH₃)CH₂ | OEt | H | |
| 73 | t-Bu | Cl | O | H | 4-OC₂H₄ | OEt | 3-Me | |
| 74 | t-Bu | Br | O | H | 4-OC₂H₄ | OEt | H | |
| 75 | t-Bu | Cl | O | H | 4-OCH(Me)CH₂ | OEt | 3-Et | |
| 76 | Hex | Br | O | H | 4-OC₂H₄ | OEt | H | |
| 77 | Et | Cl | O | H | 4-OC₂H₄ | OPro | H | 79.9~83.7 |
| 78 | Et | Cl | O | H | 4-OC₂H₄ | OPro | 3-Cl | 91.0~93.5 |
| 79 | t-Bu | Me | O | H | 4-OCH(CH₃)CH₂ | OPro | H | |
| 80 | t-Bu | Me | O | H | 4-OC₂H₄ | OPro | H | |
| 81 | t-Bu | Cl | S | H | 4-OC₂H₄ | OPro | H | 59.5~63.0 |
| 82 | t-Bu | Cl | S | H | 4-OC₂H₄ | OPro | 3-Cl | 61.5~62.5 |
| 83 | t-Bu | Br | S | H | 4-OC₂H₄ | OPro | H | |
| 84 | t-Bu | Br | S | Et | 4-OC₂H₄ | OPro | H | |
| 85 | t-Bu | Me | S | H | 4-OC₂H₄ | OPro | H | |
| 86 | t-Bu | Cl | O | H | 4-OC₂H₄ | OPro | 3-Et | |
| 87 | t-Bu | Cl | O | H | 4-OC₂H₄ | OPro | H | Oil |
| 88 | t-Bu | Cl | O | H | 4-OC₂H₄ | OPro | 3-Cl | 66.0~68.0 |
| 89 | t-Bu | Br | O | H | 4-OC₂H₄ | OPro | H | |
| 90 | t-Bu | Et | O | H | 4-OC₂H₄ | OPro | H | |
| 91 | i-Pro | Cl | O | H | 4-OC₂H₄ | OPro | H | 60.3~63.5 |
| 92 | t-Bu | Me | O | H | 4-OCH(Et)CH₂ | OPro | H | |
| 93 | t-Bu | Me | S | H | 4-OCH(CH₃)CH₂ | OPro | H | |
| 94 | t-Bu | Cl | O | H | 4-OCH(Me)CH₂ | OEt | 3-Pro—i | |
| 95 | t-Bu | Me | S | H | 4-OCH(Et)CH₂ | OPro | H | |
| 96 | t-Bu | Me | O | H | 4-OC₂H₄ | OPro | 3-Me | |
| 97 | t-Bu | Pro | O | H | 4-OC₂H₄ | OPro | H | |
| 98 | t-Bu | Cl | O | H | 4-OCH(Me)CH₂ | OPro—i | 3-Et | |
| 99 | t-Bu | Hex | S | H | 4-OC₂H₄ | OPro—i | H | |
| 100 | t-Bu | Cl | S | H | 4-OC₂H₄ | OPro—i | 3-Me | |
| 101 | t-Bu | Me | S | H | 4-OC₂H₄ | OPro—i | H | |
| 102 | t-Bu | Me | O | H | 4-OC₂H₄ | OPro—i | H | |
| 103 | t-Bu | Cl | O | H | 4-OC₂H₄ | OPro—i | H | |
| 104 | t-Bu | Cl | S | H | 4-OC₂H₄ | OPro—i | H | |
| 105 | t-Bu | Cl | S | H | 4-OCH(Me)CH₂ | OPro—i | 3-Et | |
| 106 | t-Bu | Me | O | H | 4-OCH(Et)CH₂ | OPro—i | H | |
| 107 | t-Bu | Cl | O | H | 4-OC₂H₄ | OPro—i | 3-Me | |
| 108 | t-Bu | Cl | S | Me | 4-OC₂H₄ | OPro—i | H | |
| 109 | t-Bu | Me | S | H | 4-OCH(Et)CH₂ | OPro—i | H | |
| 110 | t-Bu | Cl | O | H | 4-OC₂H₄ | OPro—i | 3-Et | |

TABLE 1-continued

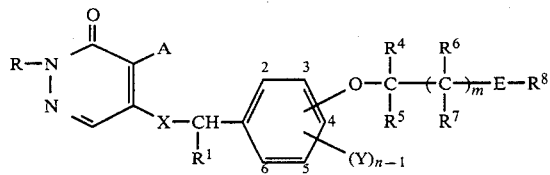

| No. | R | A | X | R¹ | $\begin{array}{c}R^4\ R^6\\O-C-(C)_m\\R^5\ R^7\end{array}$ | ER⁸ | (Y)$_{n-1}$ | M.P. (°C.) |
|---|---|---|---|---|---|---|---|---|
| 111 | t-Bu | Me | O | H | CH₃<br>\|<br>4-OCHCH₂ | OPro—i | H | |
| 112 | t-Bu | Me | S | H | CH₃<br>\|<br>4-OCHCH₂ | OPro—i | H | |
| 113 | t-Bu | Cl | S | H | 3-OC₂H₄ | OPro—i | H | |
| 114 | Et | Cl | O | H | 4-OC₂H₄ | OBu | H | |
| 115 | Pro | Cl | O | H | 4-OC₂H₄ | OBu | H | |
| 116 | s-Bu | Cl | O | H | 4-OC₂H₄ | OBu | H | |
| 117 | t-Bu | Me | S | H | 4-OC₂H₄ | OBu | H | |
| 118 | t-Bu | Me | O | H | 4-OC₂H₄ | OBu | H | |
| 119 | t-Bu | i-Pro | O | H | 4-OC₂H₄ | OBu | H | |
| 120 | t-Bu | Cl | O | H | 4-OC₂H₄ | OBu | H | |
| 121 | t-Bu | Br | O | H | 4-OC₂H₄ | OBu | H | |
| 122 | t-Bu | Cl | S | H | 4-OC₂H₄ | OBu | H | |
| 123 | t-Bu | Me | O | H | CH₃<br>\|<br>4-OCHCH₂ | OBu | H | |
| 124 | t-Bu | Cl | O | H | 4-OC₂H₄ | OBu | 3-F | |
| 125 | t-Bu | Me | S | H | CH₃<br>\|<br>4-OCHCH₂ | OBu | H | |
| 126 | t-Bu | Cl | O | H | 3-OC₂H₄ | OBu | H | |
| 127 | t-Bu | Me | O | H | Et<br>\|<br>4-OCHCH₂ | OBu | H | |
| 128 | t-Bu | Cl | S | H | 3-OC₂H₄ | OBu | H | |
| 129 | t-Bu | Me | S | H | Et<br>\|<br>—OCHCH₂ | OBu | H | |
| 130 | i-Pen | Cl | O | H | 3-OC₂H₄ | OBu | H | |
| 131 | Et | Cl | O | H | 4-OC₂H₄ | OBu—i | H | |
| 132 | Pro | Cl | O | H | 4-OC₂H₄ | OBu—i | H | |
| 133 | t-Bu | Cl | O | H | 4-OC₂H₄ | OBu—i | H | |
| 134 | t-Bu | Cl | S | H | 4-OC₂H₄ | OBu—i | H | |
| 135 | t-Bu | Me | S | H | 4-OC₂H₄ | OBu—i | H | |
| 136 | t-Bu | Me | O | H | 4-OC₂H₄ | OBu—i | H | |
| 137 | t-Bu | Br | O | H | 4-OC₂H₄ | OBu—i | 3-F | |
| 138 | t-Bu | Br | O | Me | 4-OC₂H₄ | OBu—i | 3-Cl | |
| 139 | t-Bu | Br | S | H | 4-OC₂H₄ | OBu—i | H | |
| 140 | t-Bu | Me | O | H | Et<br>\|<br>4-OCHCH₂ | OBu—i | H | |
| 141 | t-Bu | Me | S | H | Et<br>\|<br>4-OCHCH₂ | OBu—i | H | |
| 142 | t-Bu | Cl | O | H | 3-OC₂H₄ | OBu—i | H | |
| 143 | Et | Cl | O | H | 4-OC₂H₄ | OBu—s | H | |
| 144 | t-Bu | Cl | O | H | 4-OC₂H₄ | OBu—s | H | |
| 145 | t-Bu | Cl | S | H | 4-OC₂H₄ | OBu—s | H | |
| 146 | t-Bu | Cl | S | Me | 4-OC₂H₄ | OBu—s | H | |
| 147 | t-Bu | Cl | O | H | 4-OC₂H₄ | OBu—s | 3-Me | |
| 148 | t-Bu | Br | O | H | 4-OC₂H₄ | OBu—s | H | |
| 149 | t-Bu | Br | S | H | 4-OC₂H₄ | OBu—s | H | |
| 150 | t-Bu | Me | O | H | 3-OC₂H₄ | OBu—s | H | |
| 151 | t-Bu | Me | S | H | 3-OC₂H₄ | OBu—s | H | |
| 152 | i-Pro | Cl | O | H | 4-OC₂H₄ | OPen | H | |
| 153 | t-Bu | Cl | O | H | 4-OC₂H₄ | OPen | H | |
| 154 | t-Bu | Cl | O | H | 4-OC₂H₄ | OPen | 3-Me | |
| 155 | t-Bu | Cl | O | H | 4-OC₂H₄ | OPen | 3-F | |
| 156 | t-Bu | Me | O | H | 4-OC₂H₄ | OPen | H | |
| 157 | t-Bu | Me | S | H | 4-OC₂H₄ | OPen | H | |
| 158 | t-Bu | Me | S | H | Me<br>\|<br>4-OCHCH₂ | OPen | H | |
| 159 | t-Bu | Cl | O | H | 3-OC₂H₄ | OPen | H | |

TABLE 1-continued

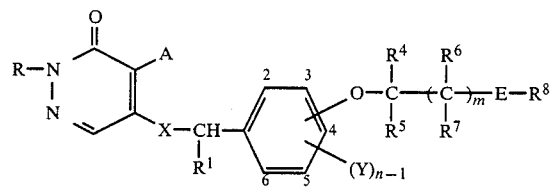

| No. | R | A | X | R¹ | O-C(R⁴)(R⁵)-(C(R⁶)(R⁷))ₘ | ER⁸ | (Y)ₙ₋₁ | M.P. (°C.) |
|---|---|---|---|---|---|---|---|---|
| 160 | Et | Cl | O | H | 4-OC₂H₄ | OCH(Me)(Pro) | H | |
| 161 | t-Bu | Cl | O | H | 4-OC₂H₄ | OCH(Me)(Pro) | 3-F | |
| 162 | t-Bu | Br | O | H | 4-OC₂H₄ | OCH(Me)(Pro) | H | |
| 163 | t-Bu | Cl | S | H | 4-OC₂H₄ | OCH(Me)(Pro) | H | |
| 164 | t-Bu | Cl | O | H | 4-OC₂H₄ | OCH(Me)(Pro) | H | |
| 165 | t-Bu | Me | O | H | 4-OC₂H₄ | OCH(Me)(Pro) | H | |
| 166 | t-Bu | Cl | O | H | 3-OC₂H₄ | OCH(Me)(Pro) | H | |
| 167 | Pro | Cl | O | H | 4-OC₂H₄ | OCH(Et)(Et) | H | |
| 168 | i-Pro | Cl | S | H | 4-OC₂H₄ | OCH(Et)(Et) | H | |
| 169 | t-Bu | Cl | O | H | 4-OC₂H₄ | OCH(Et)(Et) | H | |
| 170 | t-Bu | Cl | S | H | 4-OC₂H₄ | OCH(Et)(Et) | H | |
| 171 | t-Bu | Br | O | H | 4-OC₂H₄ | OCH(Et)(Et) | H | |
| 172 | t-Bu | Me | S | H | 4-OC₂H₄ | OCH(Et)(Et) | H | |
| 173 | t-Bu | Me | O | H | 4-OC₂H₄ | OCH(Et)(Et) | H | |

TABLE 1-continued

| No. | R | A | X | R$^1$ | $\underset{R^5\ \ R^7}{\overset{R^4\ \ R^6}{O-C-(C)_m}}$ | ER$^8$ | (Y)$_{n-1}$ | M.P. (°C.) |
|---|---|---|---|---|---|---|---|---|
| 174 | t-Bu | Me | O | H | 4-OCHCH$_2$ \| CH$_3$ | OCH(Et)(Et) | H | |
| 175 | Pro | Cl | O | H | 4-OC$_2$H$_4$ | OHex | H | |
| 176 | t-Bu | Cl | O | H | 4-OC$_2$H$_4$ | OHex | H | |
| 177 | t-Bu | Cl | S | H | 4-OC$_2$H$_4$ | OHex | H | |
| 178 | t-Bu | Me | O | H | 4-OC$_2$H$_4$ | OHex | H | |
| 179 | t-Bu | Me | S | H | 4-OC$_2$H$_4$ | OHex | H | |
| 180 | Et | Cl | O | H | 4-OC$_2$H$_4$ | OCH$_2$CH=CH$_2$ | H | |
| 181 | t-Bu | Cl | O | H | 4-OC$_2$H$_4$ | OCH$_2$CH=CH$_2$ | H | |
| 182 | t-Bu | Cl | S | H | 4-OC$_2$H$_4$ | OCH$_2$CH=CH$_2$ | H | |
| 183 | t-Bu | Cl | S | Me | 4-OC$_2$H$_4$ | OCH$_2$CH=CH$_2$ | H | |
| 184 | t-Bu | Br | O | H | 4-OC$_2$H$_4$ | OCH$_2$CH=CH$_2$ | H | |
| 185 | t-Bu | Me | S | H | 4-OC$_2$H$_4$ | OCH$_2$CH=CH$_2$ | H | |
| 186 | t-Bu | Cl | O | H | 4-OC$_2$H$_4$ | OCH$_2$CH=CH$_2$ | H | |
| 187 | t-Bu | Me | O | H | 4-OC$_2$H$_4$ | OCH$_2$CH=CH$_2$ | H | |
| 188 | t-Bu | Me | O | H | 4-OCHCH$_2$ \| CH$_3$ | OCH$_2$CH=CH$_2$ | H | |
| 189 | t-Bu | Me | S | H | 4-OCHCH$_2$ \| CH$_3$ | OCH$_2$CH=CH$_2$ | H | |
| 190 | t-Bu | Cl | O | H | 3-OC$_2$H$_4$ | OCH$_2$CH=CH$_2$ | H | |
| 191 | t-Bu | Me | O | H | 4-OCHCH$_2$ \| Et | OCH$_2$CH=CH$_2$ | H | |
| 192 | t-Bu | Me | S | H | 4-OCHCH$_2$ \| Et | OCH$_2$CH=CH$_2$ | H | |
| 193 | t-Bu | Me | O | H | 4-OC(CH$_3$)$_2$CH$_2$ | OCH$_2$CH=CH$_2$ | H | |
| 194 | t-Bu | Me | O | H | 4-OC$_2$H$_4$ | OCH$_2$CH=CHCH$_3$ | H | |
| 195 | t-Bu | Cl | O | H | 4-OC$_2$H$_4$ | OCH$_2$CH=CHCH$_3$ | H | |
| 196 | t-Bu | Cl | S | H | 4-OC$_2$H$_4$ | OCH$_2$CH=CHCH$_3$ | H | |
| 197 | t-Bu | Cl | O | H | 4-OC$_2$H$_4$ | OCH$_2$CH=CHCH$_3$ | H | |
| 198 | t-Bu | Me | O | H | 4-OCHCH$_2$ \| CH$_3$ | OCH$_2$CH=CHCH$_3$ | H | |
| 199 | t-Bu | Br | S | H | 4-OC$_2$H$_4$ | OCH$_2$CH=CHCH$_3$ | H | |
| 200 | t-Bu | Br | S | Me | 4-OC$_2$H$_4$ | OCH$_2$CH=CHCH$_3$ | H | |
| 201 | t-Bu | Me | S | H | 4-OC$_2$H$_4$ | OCH$_2$CH=CHCH$_3$ | H | |
| 202 | t-Bu | Cl | O | H | 3-OC$_2$H$_4$ | OCH$_2$CH=CHCH$_3$ | H | |
| 203 | t-Bu | Me | S | H | 4-OCHCH$_2$ \| Et | OCH$_2$CH=CHCH$_3$ | H | |
| 204 | t-Bu | Me | O | H | 4-OCHCH$_2$ \| Et | OCH$_2$CH=CHCH$_3$ | H | |
| 205 | t-Bu | Cl | O | H | 4-OCH$_2$CH$_2$CH$_2$ | OCHCH=CH$_2$ \| CH$_3$ | H | |
| 206 | t-Bu | Cl | S | H | 4-OCH$_2$CH$_2$CH$_2$ | OCHCH=CH$_2$ \| CH$_3$ | H | |
| 207 | t-Bu | Cl | O | H | 4-OCH$_2$CH$_2$CH$_2$CH$_2$ | OCHCH=CH$_2$ \| CH$_3$ | H | |
| 208 | Et | Cl | O | H | 4-OCHCH$_2$ \| Me | OCHCH=CH$_2$ \| CH$_3$ | H | |
| 209 | t-Bu | Cl | O | H | 4-OCHCH$_2$ \| Me | OCHCH=CH$_2$ \| CH$_3$ | H | |
| 210 | t-Bu | Cl | S | H | 4-OCHCH$_2$ \| Me | OCHCH=CH$_2$ \| CH$_3$ | H | |

TABLE 1-continued

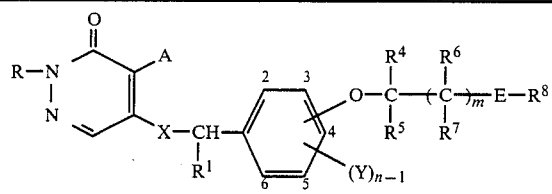

| No. | R | A | X | R¹ | O—C(R⁴)(R⁵)—(C(R⁶)(R⁷))ₘ | ER⁸ | (Y)ₙ₋₁ | M.P. (°C.) |
|---|---|---|---|---|---|---|---|---|
| 211 | t-Bu | Cl | O | H | 4-OCH₂CH(Me) | OCHCH=CH₂ with CH₃ | H | |
| 212 | t-Bu | Cl | S | H | 4-OCH₂CH(Me) | OCHCH=CH₂ with CH₃ | H | |
| 213 | t-Bu | Cl | S | H | 4-OC(CH₃)₂CH₂ | OCHCH=CH₂ with CH₃ | H | |
| 214 | t-Bu | Cl | O | H | 4-OC(CH₃)₂CH₂ | OCHCH=CH₂ with CH₃ | H | |
| 215 | t-Bu | Cl | O | H | 4-OCHCH(Me)(Me) | OCHCH=CH₂ with CH₃ | H | |
| 216 | t-Bu | Br | O | H | 4-OCHCH(Me)(Me) | OCHCH=CH₂ with CH₃ | H | |
| 217 | i-Pro | Cl | O | H | 4-OCHCH₂(Et) | OCHCH=CH₂ with CH₃ | H | |
| 218 | t-Bu | Cl | O | H | 4-OCHCH₂(Et) | OCHCH=CH₂ with CH₃ | H | |
| 219 | t-Bu | Cl | S | H | 4-OCHCH₂(Et) | OCHCH=CH₂ with CH₃ | H | |
| 220 | t-Bu | Br | O | H | 4-OCHCH₂(Et) | OCHCH=CH₂ with CH₃ | H | |
| 221 | t-Bu | Cl | O | H | 4-OCHCH₂(Pro) | OCHCH=CH₂ with CH₃ | H | |
| 222 | t-Bu | Cl | O | H | 4-OCH₂CH₂CH₂ | OCH₂CH=C(CH₃)(CH₃) | H | |
| 223 | t-Bu | Cl | O | H | 3-OCH₂CH₂CH₂ | OCH₂CH=C(CH₃)(CH₃) | H | |
| 224 | t-Bu | Cl | O | H | 4-OCHCH₂(Me) | OCH₂CH=C(CH₃)(CH₃) | H | |
| 225 | t-Bu | Cl | S | H | 4-OCHCH₂(Me) | OCH₂CH=C(CH₃)(CH₃) | H | |
| 226 | t-Bu | Br | O | H | 4-OCHCH₂(Me) | OCH₂CH=C(CH₃)(CH₃) | H | |
| 227 | t-Bu | Cl | O | H | 3-OCHCH₂(Me) | OCH₂CH=C(CH₃)(CH₃) | H | |
| 228 | t-Bu | Cl | O | H | 4-OCH₂CH(Me) | OCH₂CH=C(CH₃)(CH₃) | H | |

TABLE 1-continued

[Structure shown at top of table with substituents R, A, X, R¹, R⁴–R⁸, E, Y, positions 2,3,4,5,6]

| No. | R | A | X | R¹ | $\overset{R^4}{\underset{R^5}{O-C}}\overset{R^6}{\underset{R^7}{(C)_m}}$ | ER⁸ | $(Y)_{n-1}$ | M.P. (°C.) |
|---|---|---|---|---|---|---|---|---|
| 229 | t-Bu | Cl | S | H | 4-OCH₂CH(Me) | OCH₂CH=C(CH₃)(CH₃) | H | |
| 230 | Et | Cl | O | H | 4-OCHCH(Me)(Me) | OCH₂CH=C(CH₃)(CH₃) | 3-Me | |
| 231 | t-Bu | Cl | S | H | 4-OCHCH(Me)(Me) | OCH₂CH=C(CH₃)(CH₃) | H | |
| 232 | t-Bu | Cl | O | H | 4-OC(CH₃)₂CH₂ | OCH₂CH=C(CH₃)(CH₃) | H | |
| 233 | t-Bu | Cl | S | H | 4-OC(CH₃)₂CH₂ | OCH₂CH=C(CH₃)(CH₃) | H | |
| 234 | i-Pro | Cl | O | H | 4-OCHCH₂(Et) | OCH₂CH=C(CH₃)(CH₃) | H | |
| 235 | t-Bu | Cl | O | H | 4-OCHCH₂(Et) | OCH₂CH=C(CH₃)(CH₃) | H | |
| 236 | t-Bu | Cl | S | H | 4-OCHCH₂(Et) | OCH₂CH=C(CH₃)(CH₃) | H | |
| 237 | t-Bu | Br | O | H | 4-OCHCH₂(Et) | OCH₂CH=C(CH₃)(CH₃) | H | |
| 238 | Et | Cl | O | H | 4-OC₂H₄ | OCH₂C≡CH | H | |
| 239 | Pro | Cl | O | H | 4-OC₂H₄ | OCH₂C≡CH | H | |
| 240 | t-Bu | Me | O | H | 4-OC₂H₄ | OCH₂C≡CH | H | |
| 241 | t-Bu | Me | S | Me | 4-OC₂H₄ | OCH₂C≡CH | H | |
| 242 | t-Bu | Cl | O | H | 4-OC₂H₄ | OCH₂C≡CH | H | |
| 243 | t-Bu | Me | O | H | 4-OC(CH₃)₂CH₂ | OCH₂C≡CH | H | |
| 244 | t-Bu | Cl | O | H | 4-OC₂H₄ | OCH₂C≡CH | 3-F | |
| 245 | t-Bu | Cl | S | H | 4-OC₂H₄ | OCH₂C≡CH | H | |
| 246 | t-Bu | Me | O | H | 4-OCH₂CH(CH₃) | OCH₂C≡CH | H | |
| 247 | t-Bu | Me | O | H | 4-OCHCH₂(Et) | OCH₂C≡CH | H | |
| 248 | t-Bu | Cl | O | H | 3-OC₂H₄ | OCH₂C≡CH | H | |
| 249 | t-Bu | Me | S | H | 4-OCHCH₂(CH₃) | OCH₂C≡CH | H | |
| 250 | t-Bu | Me | O | H | 4-OCHCH₂(CH₃) | OCH₂C≡CH | H | |
| 251 | t-Bu | Cl | O | H | 4-OC₂H₄ | OCH₂C≡CCH₃ | H | |
| 252 | t-Bu | Cl | S | H | 4-OC₂H₄ | OCH₂C≡CCH₃ | H | |
| 253 | t-Bu | Br | O | H | 4-OC₂H₄ | OCH₂C≡CCH₃ | H | |

TABLE 1-continued

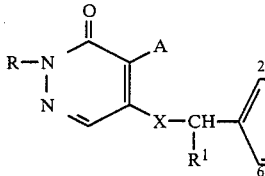

| No. | R | A | X | R¹ | O–C(R⁴)(R⁵)–(C(R⁶)(R⁷))ₘ | ER⁸ | $(Y)_{n-1}$ | M.P. (°C.) |
|---|---|---|---|---|---|---|---|---|
| 254 | t-Bu | Me | O | H | 4-OC₂H₄ | O–△H (cyclopropyl) | H | |
| 255 | t-Bu | Et | O | H | 4-OC₂H₄ | O–△H | H | |
| 256 | t-Bu | Cl | O | H | 4-OC₂H₄ | O–△H | H | |
| 257 | t-Bu | Cl | S | H | 4-OC₂H₄ | O–△H | H | |
| 258 | t-Bu | Br | O | H | 4-OC₂H₄ | O–△H | H | |
| 259 | t-Bu | Me | O | H | 4-OCHCH (Me, Me) | O–△H | H | |
| 260 | t-Bu | Me | O | H | 4-OCHCH₂ (Me) | O–△H | H | |
| 261 | t-Bu | Me | O | H | 4-OC₂H₄ | O–⬠H (cyclopentyl) | H | |
| 262 | t-Bu | Cl | O | H | 4-OC₂H₄ | O–⬠H | H | |
| 263 | t-Bu | Br | O | H | 4-OC₂H₄ | O–⬠H | H | |
| 264 | t-Bu | Me | O | H | 4-OCHCH₂ (Me) | O–⬠H | H | |
| 265 | t-Bu | Cl | S | H | 4-OC₂H₄ | O–⬠H | H | |
| 266 | t-Bu | Me | S | H | 4-OCHCH₂ (Et) | O–⬠H | H | |
| 267 | t-Bu | Me | S | H | 4-OC₂H₄ | O–⬠H | H | |
| 268 | t-Bu | Me | O | H | 4-OC₂H₄ | O–⬡H (cyclohexyl) | H | |
| 269 | t-Bu | Me | S | H | 4-OC₂H₄ | O–⬡H | H | |

TABLE 1-continued

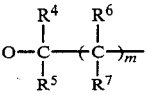

| No. | R | A | X | R¹ | O−C(R⁴)(R⁵)−(C(R⁶)(R⁷))ₘ | ER⁸ | (Y)ₙ₋₁ | M.P. (°C.) |
|---|---|---|---|---|---|---|---|---|
| 270 | t-Bu | Cl | O | H | 4-OC₂H₄ | O-cyclohexyl, H | H | |
| 271 | t-Bu | Cl | S | H | 4-OC₂H₄ | O-cyclohexyl, H | H | |
| 272 | t-Bu | Br | O | H | 4-OC₂H₄ | O-cyclohexyl, H | H | |
| 273 | t-Bu | Et | O | H | 4-OC₂H₄ | O-cyclohexyl, H | H | |
| 274 | t-Bu | Me | O | H | 4-OCH₂CH(Me) | O-cyclohexyl, H | H | |
| 275 | t-Bu | Me | S | Me | 4-OCH(Me)CH₂ | O-cyclohexyl, H | H | |
| 276 | t-Bu | Me | O | H | 4-OCH(Me)CH₂ | O-cyclohexyl, H | H | |
| 277 | t-Bu | Me | O | H | 4-OCH(Et)CH₂ | O-cyclohexyl, H | H | |
| 278 | t-Bu | Cl | S | H | 4-OCH₂CH(Me) | SMe | H | |
| 279 | t-Bu | Me | O | H | 4-OC₂H₄ | SMe | H | |
| 280 | t-Bu | Cl | O | H | 4-OC₂H₄ | SMe | 3-Cl | |
| 281 | t-Bu | Cl | O | H | 4-OC₂H₄ | SMe | H | 77.0~79.0 |
| 282 | t-Bu | Cl | S | H | 4-OC₂H₄ | SMe | H | |
| 283 | t-Bu | Cl | O | H | 4-OCH(Me)CH(Me) | SMe | H | |
| 284 | Pen | Cl | O | H | 4-OC₂H₄ | SMe | H | |
| 285 | t-Bu | Me | S | H | 4-OC₂H₄ | SMe | H | |
| 286 | t-Bu | Cl | O | H | 4-OC(CH₃)₂CH₂ | SMe | H | |
| 287 | t-Bu | Me | S | H | 4-OCH(Et)CH₂ | SMe | H | |
| 288 | t-Bu | Me | O | H | 4-OCH(Me)CH₂ | SMe | H | |
| 289 | Pro | Cl | O | H | 4-OC₂H₄ | SEt | H | |
| 290 | t-Bu | Me | O | H | 4-OC₂H₄ | SEt | H | |
| 291 | t-Bu | Cl | O | H | 4-OC₂H₄ | SEt | H | 60.0~62.0 |
| 292 | t-Bu | Cl | S | H | 4-OC₂H₄ | SEt | H | |
| 293 | t-Bu | Cl | O | H | 4-OCH(Me)CH(Me) | SEt | H | |
| 294 | t-Bu | Me | S | H | 4-OC₂H₄ | SEt | H | |
| 295 | t-Bu | Cl | O | H | 4-OC₂H₄ | SEt | 3-Et | |

TABLE 1-continued

Structure:
R—N(N)—C(=O)—C(A)=C(X—CHR¹—)  pyridazinone, with phenyl bearing positions 2,3,4,5,6, (Y)ₙ₋₁, and O—C(R⁴)(R⁵)—(C(R⁶)(R⁷))ₘ—E—R⁸

| No. | R | A | X | R¹ | O—C(R⁴)(R⁵)—(C(R⁶)(R⁷))ₘ | ER⁸ | (Y)ₙ₋₁ | M.P. (°C.) |
|---|---|---|---|---|---|---|---|---|
| 296 | t-Bu | Cl | S | Me | 4-OC₂H₄ | SEt | H | |
| 297 | t-Bu | Me | O | H | 4-OCHCH₂ \| Me | SEt | H | |
| 298 | t-Bu | Me | S | H | 4-OCHCH₂ \| Me | SEt | H | |
| 299 | t-Bu | Cl | S | H | 4-OCHCH₂ \| Et | SEt | H | |
| 300 | Et | Cl | S | H | 4-OC₂H₄ | SPro | H | |
| 301 | t-Bu | Me | O | H | 4-OC₂H₄ | SPro | H | |
| 302 | t-Bu | Cl | O | H | 4-OC₂H₄ | SPro | H | 66.5~67.9 |
| 303 | t-Bu | Cl | S | H | 4-OC₂H₄ | SPro | H | |
| 304 | t-Bu | Br | O | H | 4-OC₂H₄ | SPro | H | |
| 305 | t-Bu | Me | O | H | 4-OCHCH₂ \| Me | SPro | H | |
| 306 | t-Bu | Me | S | H | 4-OC(CH₃)₂CH₂ | SPro | H | |
| 307 | t-Bu | Cl | O | H | 4-OCH₂CH \| Me | SPro | H | |
| 308 | t-Bu | Me | O | H | 4-OC₂H₄ | SPro—i | H | |
| 309 | t-Bu | Et | O | H | 4-OC₂H₄ | SPro—i | H | |
| 310 | t-Bu | Cl | O | H | 4-OC₂H₄ | SPro—i | H | 82.0~84.5 |
| 311 | t-Bu | Cl | O | H | 4-OC₂H₄ | SPro—i | 3-Me | |
| 312 | t-Bu | Cl | S | H | 4-OC₂H₄ | SPro—i | H | |
| 313 | t-Bu | Cl | S | H | 4-OC₂H₄ | SPro—i | 3-F | |
| 314 | t-Bu | Cl | O | H | 4-OC(CH₃)₂CH₂ | SPro—i | H | |
| 315 | t-Bu | Me | O | H | 4-OCHCH₂ \| Me | SPro—i | H | |
| 316 | t-Bu | Me | S | H | 4-OCHCH₂ \| Me | SPro—i | H | |
| 317 | t-Bu | Me | O | H | 4-OCHCH₂ \| Et | SPro—i | H | |
| 318 | t-Bu | Cl | S | H | 3-OC₂H₄ | SPro—i | H | |
| 319 | t-Bu | Me | O | H | 4-OC₂H₄ | SBu | H | |
| 320 | t-Bu | Pro | S | H | 4-OC₂H₄ | SBu | H | |
| 321 | t-Bu | Cl | O | H | 4-OC₂H₄ | SBu | H | 57.0~58.0 |
| 322 | t-Bu | Cl | S | H | 4-OC₂H₄ | SBu | H | |
| 323 | t-Bu | Cl | O | H | 4-OCHCH₂ \| Et | SBu | H | |
| 324 | t-Bu | Me | O | H | 4-OCHCH₂ \| Me | SBu | H | |
| 325 | t-Bu | Me | S | H | 4-OC(CH₃)₂CH₂ | SBu | H | |
| 326 | t-Bu | Me | O | H | 4-OCHCH₂ \| Et | SBu | H | |
| 327 | t-Bu | Me | S | H | 4-OC₂H₄ | SPen | H | |
| 328 | t-Bu | Me | O | H | 4-OCHCH₂ \| Me | SPen | H | |
| 329 | t-Bu | Cl | O | H | 4-OC₂H₄ | SPen | H | |
| 330 | t-Bu | Cl | S | H | 4-OC₂H₄ | SPen | H | |
| 331 | t-Bu | Br | S | H | 4-OC₂H₄ | SPen | H | |
| 332 | t-Bu | Me | S | H | 4-OCH₂CH \| Me | SPen | H | |
| 333 | t-Bu | Et | O | H | 4-OC₂H₄ | SPen | H | |
| 334 | t-Bu | Me | O | H | 4-OC₂H₄ | SOMe | H | |
| 335 | t-Bu | Me | O | H | 4-OC₂H₄ | SO₂Me | H | |
| 336 | t-Bu | Cl | O | H | 4-OC₂H₄ | SOMe | H | |
| 337 | t-Bu | Cl | O | H | 4-OC₂H₄ | SO₂Me | H | |
| 338 | t-Bu | Cl | S | H | 4-OC₂H₄ | SOMe | H | |

TABLE 1-continued

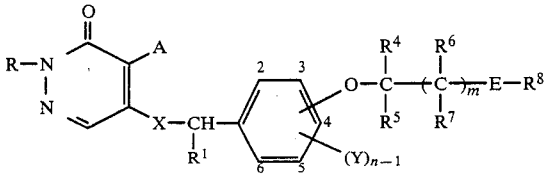

| No. | R | A | X | R¹ | $\begin{array}{c}R^4\ R^6\\ O-C-(-C-)_m\\ R^5\ R^7\end{array}$ | ER⁸ | (Y)$_{n-1}$ | M.P. (°C.) |
|---|---|---|---|---|---|---|---|---|
| 339 | t-Bu | Me | O | H | Me<br>\|<br>4-OCHCH₂ | SO₂Me | H | |
| 340 | t-Bu | Cl | O | H | Me<br>\|<br>4-OCHCH₂ | SOMe | H | |
| 341 | t-Bu | Cl | O | H | Me<br>\|<br>4-OCHCH₂ | SO₂Me | H | |
| 342 | t-Bu | Me | O | H | 4-OC₂H₄ | SOEt | H | |
| 343 | t-Bu | Cl | S | H | 4-OC₂H₄ | SO₂Et | H | |
| 344 | t-Bu | Cl | S | H | 4-OC₂H₄ | SOEt | H | |
| 345 | t-Bu | Cl | S | H | 4-OC₂H₄ | SO₂Et | H | |
| 346 | t-Bu | Et | O | H | 4-OC₂H₄ | SOEt | H | |
| 347 | t-Bu | Cl | O | H | 4-OC₂H₄ | SO₂Et | H | |
| 348 | t-Bu | Cl | O | H | Me<br>\|<br>4-OCHCH₂ | SOEt | H | |
| 349 | t-Bu | Me | O | H | Me<br>\|<br>4-OCHCH₂ | SO₂Et | H | |
| 350 | t-Bu | Cl | O | H | 4-OC₂H₄ | SOPro | H | |
| 351 | t-Bu | Cl | O | H | 4-OC₂H₄ | SO₂Pro | H | |
| 352 | t-Bu | Cl | S | H | 4-OC₂H₄ | SOPro | H | |
| 353 | t-Bu | Cl | S | H | 4-OC₂H₄ | SO₂Pro | H | |
| 354 | t-Bu | Cl | O | H | Me<br>\|<br>4-OCHCH₂ | SOPro | H | |
| 355 | t-Bu | Cl | O | H | Me<br>\|<br>4-OCHCH₂ | SO₂Pro | H | |
| 356 | t-Bu | Cl | O | H | 4-OC₂H₄ | SOPro—i | H | |
| 357 | t-Bu | Cl | O | H | 4-OC₂H₄ | SO₂Pro—i | H | |
| 358 | t-Bu | Cl | O | H | Me<br>\|<br>4-OCHCH₂ | SOPro—i | H | |
| 359 | t-Bu | Cl | O | H | Me<br>\|<br>4-OCHCH₂ | SO₂Pro—i | H | |
| 360 | t-Bu | Cl | S | H | 4-OC₂H₄ | SOPro—i | H | |
| 361 | t-Bu | Cl | S | H | 4-OC₂H₄ | SO₂Pro—i | H | |
| 362 | t-Bu | Cl | O | H | 4-OC₂H₄ | SOBu | H | |
| 363 | t-Bu | Cl | O | H | 4-OC₂H₄ | SO₂Bu | H | |
| 364 | t-Bu | Me | O | H | 4-OC₂H₄ | SOPen | H | |
| 365 | t-Bu | Me | O | H | 4-OC₂H₄ | SO₂Pen | H | |
| 366 | i-Pro | Cl | S | H | 4-OC₂H₄ | OCMe<br>\|\|<br>O | H | |
| 367 | t-Bu | Cl | O | H | 4-OC₂H₄ | OCMe<br>\|\|<br>O | H | 99.0~100.8 |
| 368 | t-Bu | Br | O | H | 4-OC₂H₄ | OCMe<br>\|\|<br>O | H | |
| 369 | t-Bu | Cl | S | H | 4-OC₂H₄ | OCMe<br>\|\|<br>O | H | 89.0~90.4 |
| 370 | t-Bu | Cl | S | H | Me<br>\|<br>4-OCHCH₂ | OCMe<br>\|\|<br>O | H | |
| 371 | t-Bu | Me | S | H | 4-OC₂H₄ | OCMe<br>\|\|<br>O | H | |
| 372 | t-Bu | Me | O | H | 4-OC₂H₄ | OCMe<br>\|\|<br>O | H | |
| 373 | t-Bu | Cl | O | H | Et<br>\|<br>4-OCHCH₂ | OCEt<br>\|\|<br>O | H | |

TABLE 1-continued

Structure:

R—N(—N=)—C(=O) ring with A and X—CHR¹ substituents, connected to a phenyl ring (positions 2,3,4,5,6) with (Y)_{n-1} and O—C(R⁴)(R⁵)—(C(R⁶)(R⁷))_m—E—R⁸

| No. | R | A | X | R¹ | O-C(R⁴)(R⁵)(C(R⁶)(R⁷))_m | ER⁸ | (Y)_{n-1} | M.P. (°C.) |
|---|---|---|---|---|---|---|---|---|
| 374 | t-Bu | Br | O | H | 4-OC₂H₄ | OC(=O)Et | H | |
| 375 | t-Bu | Cl | S | H | 4-OC₂H₄ | OC(=O)Et | H | |
| 376 | t-Bu | Cl | O | H | 4-OC₂H₄ | OC(=O)Et | H | |
| 377 | t-Bu | Me | O | H | 4-OC₂H₄ | OC(=O)Et | H | |
| 378 | t-Bu | Cl | O | H | 4-OC(CH₃)₂CH₂ | OC(=O)Pro | H | |
| 379 | t-Bu | Cl | O | H | 4-OC₂H₄ | OC(=O)Pro | H | |
| 380 | t-Bu | Me | S | H | 4-OC₂H₄ | OC(=O)Pro | H | |
| 381 | t-Bu | Cl | S | H | 4-OC₂H₄ | OC(=O)Pro | H | |
| 382 | t-Bu | Pro | S | H | 3-OC₂H₄ | OC(=O)Pro | H | |
| 383 | t-Bu | Cl | O | H | 4-OCH₂CH(Me) | OC(=O)Pro—i | H | |
| 384 | t-Bu | Cl | O | H | 4-OC₂H₄ | OC(=O)Pro—i | H | |
| 385 | t-Bu | Cl | S | H | 4-OC₂H₄ | OC(=O)Pro—i | H | |
| 386 | t-Bu | Cl | O | H | 4-OCH(Me)CH₂ | OC(=O)Pro—i | H | |
| 387 | t-Bu | Cl | S | H | 4-OCH(Me)CH₂ | OC(=O)Pro—i | H | |
| 389 | t-Bu | Me | O | H | 4-OC₂H₄ | OC(=O)Pro—i | H | |
| 390 | Et | Cl | O | H | 4-OC₂H₄ | OC(=O)Bu | H | |
| 391 | t-Bu | Cl | O | H | 4-OC₂H₄ | OC(=O)Bu | H | Oil |
| 392 | t-Bu | Cl | S | H | 4-OC₂H₄ | OC(=O)Bu | H | Oil |
| 393 | t-Bu | Br | O | H | 4-OC₂H₄ | OC(=O)Bu | H | |
| 394 | t-Bu | Cl | O | H | 4-OC₂H₄ | OC(=O)Bu—t | H | |
| 395 | t-Bu | Cl | S | H | 4-OC₂H₄ | OC(=O)Bu—t | H | |
| 396 | t-Bu | Cl | O | H | 4-OCH(Me)CH₂ | OC(=O)Bu—t | H | |
| 397 | t-Bu | Cl | S | H | 4-OC₂H₄ | OC(=O)Pen | H | |

TABLE 1-continued

| No. | R | A | X | $R^1$ | $O-\underset{R^5}{\overset{R^4}{C}}-(\underset{R^7}{\overset{R^6}{C}})_m$ | $ER^8$ | $(Y)_{n-1}$ | M.P. (°C.) |
|---|---|---|---|---|---|---|---|---|
| 398 | t-Bu | Me | O | H | Et \| 4-OCHCH$_2$ | OCPen ‖ O | H | |
| 399 | Et | Cl | S | H | 4-OCH$_2$CH$_2$CH$_2$ | OMe | H | |
| 400 | Pro | Br | S | Et | 4-OCH$_2$CH$_2$CH$_2$ | OMe | Me | |
| 401 | t-Bu | Cl | O | H | 4-OCH$_2$CH$_2$CH$_2$ | OMe | 3-F | |
| 402 | t-Bu | Cl | O | H | 4-OCH$_2$CH$_2$CH$_2$ | OMe | H | 94.0~96.0 |
| 403 | t-Bu | Cl | S | H | 4-OCH$_2$CH$_2$CH$_2$ | OMe | H | 102.0~104.0 |
| 404 | t-Bu | Et | O | H | 4-OCH$_2$CH$_2$CH$_2$ | OMe | H | |
| 405 | t-Bu | Cl | S | Me | 4-OCH$_2$CH$_2$CH$_2$ | OMe | H | |
| 406 | t-Bu | Me | S | H | 4-OCH$_2$CH$_2$CH$_2$ | OMe | H | |
| 407 | t-Bu | Cl | O | H | 3-OCH$_2$CH$_2$CH$_2$ | OMe | H | |
| 408 | t-Bu | Me | O | H | 4-OCH$_2$CH$_2$CH$_2$ | OMe | H | |
| 409 | t-Bu | Cl | S | H | 3-OCH$_2$CH$_2$CH$_2$ | OMe | H | |
| 410 | Et | Cl | S | H | 4-OCH$_2$CH$_2$CH$_2$ | OEt | H | |
| 411 | Pro | Cl | O | H | 4-OCH$_2$CH$_2$CH$_2$ | OEt | 3-Me | |
| 412 | t-Bu | Cl | O | H | 4-OCH$_2$CH$_2$CH$_2$ | OEt | 3-F | |
| 413 | t-Bu | Cl | O | H | 4-OCH$_2$CH$_2$CH$_2$ | OEt | H | 77.0~78.0 |
| 414 | t-Bu | Br | S | H | 4-OCH$_2$CH$_2$CH$_2$ | OEt | H | |
| 415 | t-Bu | Cl | S | H | 4-OCH$_2$CH$_2$CH$_2$ | OEt | H | 111.0~112.0 |
| 416 | t-Bu | Cl | S | H | 3-OCH$_2$CH$_2$CH$_2$ | OEt | H | |
| 417 | t-Bu | Cl | O | H | 3-OCH$_2$CH$_2$CH$_2$ | OEt | H | |
| 418 | t-Bu | Me | S | H | 4-OCH$_2$CH$_2$CH$_2$ | OEt | H | |
| 419 | t-Bu | Me | O | H | 4-OCH$_2$CH$_2$CH$_2$ | OEt | H | |
| 420 | Et | Cl | O | H | 4-OCH$_2$CH$_2$CH$_2$ | OPro | H | |
| 421 | t-Bu | Cl | O | H | 4-OCH$_2$CH$_2$CH$_2$ | OPro | H | Oil |
| 422 | t-Bu | Br | O | H | 4-OCH$_2$CH$_2$CH$_2$ | OPro | H | Oil |
| 423 | t-Bu | Cl | O | H | 4-OCH$_2$CH$_2$CH$_2$ | OPro | 3-F | |
| 424 | t-Bu | Cl | S | H | 4-OCH$_2$CH$_2$CH$_2$ | OPro | H | 78.5~80.0 |
| 425 | t-Bu | Cl | S | Me | 4-OCH$_2$CH$_2$CH$_2$ | OPro | H | |
| 426 | t-Bu | Cl | O | H | 3-OCH$_2$CH$_2$CH$_2$ | OPro | H | |
| 427 | t-Bu | Me | O | H | 4-OCH$_2$CH$_2$CH$_2$ | OPro | H | |
| 428 | t-Bu | Cl | S | H | 3-OCH$_2$CH$_2$CH$_2$ | OPro | H | |
| 429 | Bu | i-Bu | O | H | 4-OCH$_2$CH$_2$CH$_2$ | OPro—i | H | |
| 430 | t-Bu | Cl | S | H | 4-OCH$_2$CH$_2$CH$_2$ | OPro—i | H | |
| 431 | t-Bu | Cl | O | H | 4-OCH$_2$CH$_2$CH$_2$ | OPro—i | H | |
| 432 | t-Bu | Br | O | H | 4-OCH$_2$CH$_2$CH$_2$ | OPro—i | H | |
| 433 | t-Bu | Me | O | H | 3-OCH$_2$CH$_2$CH$_2$ | OPro—i | H | |
| 434 | t-Bu | Cl | S | H | 3-OCH$_2$CH$_2$CH$_2$ | OPro—i | H | |
| 435 | t-Bu | Me | S | H | 4-OCH$_2$CH$_2$CH$_2$ | OPro—i | H | |
| 436 | t-Bu | Me | O | H | 4-OCH$_2$CH$_2$CH$_2$ | OPro—i | H | |
| 437 | Pro | Cl | O | H | 4-OCH$_2$CH$_2$CH$_2$ | OBu | H | |
| 438 | t-Bu | Me | S | H | 4-OCH$_2$CH$_2$CH$_2$ | OBu | H | |
| 439 | t-Bu | Cl | S | H | 4-OCH$_2$CH$_2$CH$_2$ | OBu | H | |
| 440 | t-Bu | Cl | S | Me | 4-OCH$_2$CH$_2$CH$_2$ | OBu | H | |
| 441 | t-Bu | Pen | O | H | 3-OCH$_2$CH$_2$CH$_2$ | OBu | H | |
| 442 | t-Bu | Cl | S | H | 3-OCH$_2$CH$_2$CH$_2$ | OBu | H | |
| 443 | t-Bu | Cl | O | H | 4-OCH$_2$CH$_2$CH$_2$ | OBu—i | H | |
| 444 | t-Bu | Cl | S | H | 4-OCH$_2$CH$_2$CH$_2$ | OBu—i | H | |
| 445 | t-Bu | Me | O | H | 4-OCH$_2$CH$_2$CH$_2$ | OBu—i | H | |
| 446 | t-Bu | Cl | O | H | 3-OCH$_2$CH$_2$CH$_2$ | OBu—i | H | |
| 447 | t-Bu | Cl | S | H | 3-OCH$_2$CH$_2$CH$_2$ | OBu—i | H | |
| 448 | t-Bu | Cl | O | H | 4-OCH$_2$CH$_2$CH$_2$ | OBu—s | H | |
| 449 | t-Bu | Cl | S | H | 4-OCH$_2$CH$_2$CH$_2$ | OBu—s | H | |
| 450 | t-Bu | Cl | S | H | 3-OCH$_2$CH$_2$CH$_2$ | OBu—s | H | |
| 451 | t-Bu | Cl | O | H | 3-OCH$_2$CH$_2$CH$_2$ | OBu—s | H | |
| 452 | Et | Cl | O | H | 4-OCH$_2$CH$_2$CH$_2$ | OPen | 3-Me | |
| 453 | t-Bu | Cl | O | H | 4-OCH$_2$CH$_2$CH$_2$ | OPen | H | |
| 454 | t-Bu | Cl | O | H | 3-OCH$_2$CH$_2$CH$_2$ | OPen | H | |
| 455 | t-Bu | Cl | O | H | 4-OCH$_2$CH$_2$CH$_2$ | OCH(Me)(Pro) | H | |

TABLE 1-continued

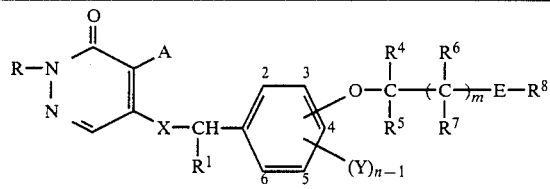

| No. | R | A | X | R¹ | O-C(R⁴)(R⁵)-(C(R⁶)(R⁷))ₘ | ER⁸ | (Y)ₙ₋₁ | M.P. (°C.) |
|---|---|---|---|---|---|---|---|---|
| 456 | t-Bu | Cl | O | H | 4-OCH₂CH₂CH₂ | OCH(Et)(Et) | H | |
| 457 | t-Bu | Br | S | H | 3-OCH₂CH₂CH₂ | OHex | H | |
| 458 | t-Bu | Cl | O | H | 4-OCH₂CH₂CH₂ | OCH₂CH=CH₂ | H | |
| 459 | t-Bu | Cl | S | H | 4-OCH₂CH₂CH₂ | OCH₂CH=CH₂ | H | |
| 460 | t-Bu | Me | O | H | 4-OCH₂CH₂CH₂ | OCH₂CH=CH₂ | H | |
| 461 | t-Bu | Cl | O | H | 3-OCH₂CH₂CH₂ | OCH₂CH=CH₂ | H | |
| 462 | t-Bu | Me | O | H | 4-OCH₂CH₂CH₂ | OCH₂CH=CHCH₃ | H | |
| 463 | t-Bu | Cl | O | H | 4-OCH₂CH₂CH₂ | OCH₂CH=CHCH₃ | H | |
| 464 | t-Bu | Cl | S | H | 4-OCH₂CH₂CH₂ | OCH₂CH=CHCH₃ | H | |
| 465 | t-Bu | Cl | O | H | 3-OCH₂CH₂CH₂ | OCH₂CH=CHCH₃ | H | |
| 466 | Pro | Cl | O | H | 4-OCH₂CH₂CH₂ | OCH₂C≡CH | H | |
| 467 | t-Bu | Cl | O | H | 4-OCH₂CH₂CH₂ | OCH₂C≡CH | H | |
| 468 | t-Bu | Cl | S | H | 4-OCH₂CH₂CH₂ | OCH₂C≡CH | H | |
| 469 | t-Bu | Br | O | H | 4-OCH₂CH₂CH₂ | OCH₂C≡CH | H | |
| 470 | t-Bu | Cl | O | H | 4-OCH₂CH₂CH₂ | OCH₂C≡CCH₃ | H | |
| 471 | t-Bu | Cl | S | H | 4-OCH₂CH₂CH₂ | OCH₂C≡CCH₃ | H | |
| 472 | t-Bu | Cl | O | H | 4-OCH₂CH₂CH₂ | O-cyclopropyl | H | |
| 473 | t-Bu | Cl | S | H | 4-OCH₂CH₂CH₂ | O-cyclopropyl | H | |
| 474 | t-Bu | Br | O | H | 4-OCH₂CH₂CH₂ | O-cyclopropyl | H | |
| 475 | t-Bu | Et | O | H | 3-OCH₂CH₂CH₂ | O-cyclopropyl | H | |
| 476 | t-Bu | Cl | O | H | 4-OCH₂CH₂CH₂ | O-cyclopentyl | H | |
| 477 | t-Bu | Cl | S | H | 4-OCH₂CH₂CH₂ | O-cyclopentyl | H | |
| 478 | t-Bu | Cl | O | H | 4-OCH₂CH₂CH₂ | O-cyclohexyl | H | |
| 479 | t-Bu | Cl | S | H | 4-OCH₂CH₂CH₂ | O-cyclohexyl | H | |
| 480 | t-Bu | Me | O | H | 4-OCH₂CH₂CH₂CH₂ | OMe | H | |
| 481 | t-Bu | Cl | O | H | 4-OCH₂CH₂CH₂CH₂ | OMe | H | |
| 482 | t-Bu | Cl | S | H | 4-OCH₂CH₂CH₂CH₂ | OMe | H | |
| 483 | t-Bu | Cl | O | H | 3-OCH₂CH₂CH₂CH₂ | OMe | H | |
| 484 | t-Bu | Cl | O | H | 4-OCH₂CH₂CH₂CH₂ | OEt | H | |
| 485 | t-Bu | Cl | S | H | 4-OCH₂CH₂CH₂CH₂ | OEt | H | |
| 486 | t-Bu | Br | O | H | 4-OCH₂CH₂CH₂CH₂ | OEt | H | |
| 487 | t-Bu | Cl | O | H | 4-OCH₂CH₂CH₂CH₂ | OPro | H | |
| 488 | t-Bu | Br | O | H | 4-OCH₂CH₂CH₂CH₂ | OPro | H | |
| 489 | t-Bu | Cl | S | H | 4-OCH₂CH₂CH₂CH₂ | OPro | H | |
| 490 | t-Bu | Cl | O | H | 3-OCH₂CH₂CH₂CH₂ | OPro | H | |
| 491 | t-Bu | Cl | O | H | 4-OCH₂CH₂CH₂CH₂ | OPro—i | H | |
| 492 | t-Bu | Cl | S | H | 4-OCH₂CH₂CH₂CH₂ | OPro—i | H | |
| 493 | t-Bu | Cl | O | H | 4-OCH₂CH₂CH₂CH₂ | OBu | H | |
| 494 | t-Bu | Cl | S | H | 4-OCH₂CH₂CH₂CH₂ | OBu | H | |
| 495 | t-Bu | Cl | O | H | 4-OCH₂CH₂CH₂CH₂ | OBu—i | H | |

TABLE 1-continued

[Structure: R-N-N=... pyridazinone with A, X-CHR¹, phenyl with (Y)$_{n-1}$ and O-C(R⁴)(R⁵)-(C(R⁶)(R⁷))$_m$-E-R⁸]

| No. | R | A | X | R¹ | O-C(R⁴)(R⁵)-(C(R⁶)(R⁷))$_m$ | ER⁸ | (Y)$_{n-1}$ | M.P. (°C.) |
|---|---|---|---|---|---|---|---|---|
| 496 | t-Bu | Cl | S | H | 3-OCH₂CH₂CH₂CH₂ | OBu—i | H | |
| 497 | t-Bu | Cl | O | H | 4-OCH₂CH₂CH₂CH₂ | OBu—s | H | |
| 498 | t-Bu | Cl | S | H | 3-OCH₂CH₂CH₂CH₂ | OBu—s | H | |
| 499 | t-Bu | Br | O | H | 3-OCH₂CH₂CH₂ | OHex | H | |
| 500 | Et | Cl | O | H | 4-OCH(Me)CH₂ | OMe | H | 51.0~53.0 |
| 501 | i-Pro | Cl | O | H | 4-OCH(Me)CH₂ | OMe | H | 115.2~116.1 |
| 502 | t-Bu | Cl | O | H | 4-OCH(Me)CH₂ | OMe | H | 68.4~70.0 |
| 503 | t-Bu | Br | O | H | 4-OCH(Me)CH₂ | OMe | H | |
| 504 | t-Bu | Cl | S | H | 4-OCH(Me)CH₂ | OMe | H | 51.0~52.0 |
| 505 | t-Bu | Br | S | H | 4-OCH(Me)CH₂ | OMe | H | |
| 506 | t-Bu | Cl | O | H | 3-OCH(Me)CH₂ | OMe | H | |
| 507 | Et | Cl | O | H | 4-OCH(Me)CH₂ | OEt | H | |
| 508 | t-Bu | Cl | O | H | 4-OCH(Me)CH₂ | OEt | 3-Me | Oil |
| 509 | t-Bu | Cl | S | H | 4-OCH(Me)CH₂ | OEt | 3-Me | Oil |
| 510 | t-Bu | Cl | S | Me | 4-OCH(Me)CH₂ | OEt | H | |
| 511 | t-Bu | Cl | O | H | 4-OCH(Me)CH₂ | OEt | H | 72.3~73.1 |
| 512 | t-Bu | Br | O | H | 4-OCH(Me)CH₂ | OEt | H | |
| 513 | t-Bu | Cl | S | H | 4-OCH(Me)CH₂ | OEt | H | 89.2~90.2 |
| 514 | t-Bu | Cl | O | H | 3-OCH(Me)CH₂ | OEt | H | |
| 515 | t-Bu | Cl | S | H | 2-OCH(Me)CH₂ | OEt | H | Oil |
| 516 | t-Bu | Cl | O | H | 2-OCH(Me)CH₂ | OEt | H | Oil |
| 517 | t-Bu | Cl | O | H | 4-OCH(Me)CH₂ | OPro | H | Oil |
| 518 | t-Bu | Cl | O | H | 4-OCH(Me)CH₂ | OPro | 3-Me | |
| 519 | t-Bu | Br | O | H | 4-OCH(Me)CH₂ | OPro | H | |
| 520 | t-Bu | Br | S | H | 4-OCH(Me)CH₂ | OPro | H | |

TABLE 1-continued

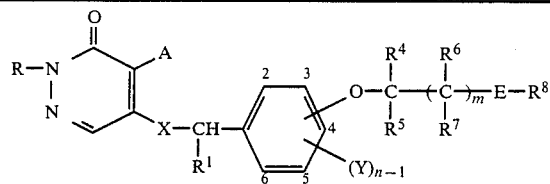

| No. | R | A | X | R¹ | O-C(R⁴)(R⁵)-(C(R⁶)(R⁷))ₘ | ER⁸ | (Y)ₙ₋₁ | M.P. (°C.) |
|---|---|---|---|---|---|---|---|---|
| 521 | t-Bu | Cl | S | H | Me / 4-OCHCH₂ | OPro | H | Oil |
| 522 | t-Bu | Cl | S | H | Me / 3-OCHCH₂ | OPro | H | Oil |
| 523 | t-Bu | Cl | O | H | Me / 3-OCHCH₂ | OPro | H | Oil |
| 524 | t-Bu | Cl | O | H | Me / 4-OCHCH₂ | OPro—i | H | 60.0~62.0 |
| 525 | t-Bu | Br | O | H | Me / 4-OCHCH₂ | OPro—i | H | |
| 526 | t-Bu | Br | S | H | Me / 4-OCHCH₂ | OPro—i | H | |
| 527 | t-Bu | Cl | S | H | Me / 4-OCHCH₂ | OPro—i | H | 83.0~84.5 |
| 528 | t-Bu | Cl | S | Me | Me / 4-OCHCH₂ | OPro—i | H | |
| 529 | t-Bu | Cl | O | H | Me / 3-OCHCH₂ | OPro—i | H | |
| 530 | Pro | Cl | O | H | Me / 4-OCHCH₂ | OBu | H | |
| 531 | t-Bu | Cl | O | H | Me / 4-OCHCH₂ | OBu | H | Oil |
| 532 | t-Bu | Br | O | H | Me / 4-OCHCH₂ | OBu | H | |
| 533 | t-Bu | Cl | S | H | Me / 4-OCHCH₂ | OBu | H | Oil |
| 534 | t-Bu | Cl | O | H | Me / 3-OCHCH₂ | OBu | H | |
| 535 | t-Bu | Cl | O | H | Me / 4-OCHCH₂ | OBu—i | H | Oil |
| 536 | t-Bu | Br | O | H | Me / 4-OCHCH₂ | OBu—i | H | |
| 537 | t-Bu | Br | S | H | Me / 4-OCHCH₂ | OBu—i | H | |
| 538 | t-Bu | Cl | S | H | Me / 4-OCHCH₂ | OBu—i | H | Oil |
| 539 | t-Bu | Cl | O | H | Me / 4-OCHCH₂ | OBu—s | H | |
| 540 | t-Bu | Br | O | H | Me / 4-OCHCH₂ | OBu—s | H | |
| 541 | t-Bu | Cl | S | H | Me / 4-OCHCH₂ | OBu—s | H | |
| 542 | t-Bu | Me | O | H | Me / 4-OCHCH₂ | OBu—s | H | |
| 543 | t-Bu | Cl | O | H | Me / 4-OCHCH₂ | OPen | H | |

TABLE 1-continued

[Structure diagram showing pyridazinone compound with substituents R, A, X, R¹, R⁴-R⁸, Y, and numbered positions]

| No. | R | A | X | R¹ | O—C(R⁴)(R⁵)—(C(R⁶)(R⁷))ₘ | ER⁸ | (Y)ₙ₋₁ | M.P. (°C.) |
|-----|---|---|---|----|--------------------------|-----|--------|------------|
| 544 | t-Bu | Br | O | H | Me / 4-OCHCH₂ | OPen | H | |
| 545 | t-Bu | Et | O | H | Me / 4-OCHCH₂ | OCH(Me)(Pro) | H | |
| 546 | t-Bu | Cl | O | H | Me / 4-OCHCH₂ | OCH(Me)(Pro) | H | |
| 547 | t-Bu | Cl | S | H | Me / 4-OCHCH₂ | OCH(Me)(Pro) | H | |
| 548 | t-Bu | Cl | S | H | Me / 4-OCHCH₂ | OCH(Et)(Et) | H | |
| 549 | t-Bu | Cl | O | H | Me / 4-OCHCH₂ | OCH(Et)(Et) | H | |
| 550 | t-Bu | Me | O | H | Me / 4-OCHCH₂ | OCH(Et)(Et) | H | |
| 551 | t-Bu | Br | O | H | Me / 4-OCHCH₂ | OHex | H | Oil |
| 552 | t-Bu | Cl | O | H | Me / 4-OCHCH₂ | OHex | H | Oil |
| 553 | t-Bu | Cl | S | H | Me / 4-OCHCH₂ | OHex | H | Oil |
| 554 | t-Bu | Cl | O | H | Me / 4-OCHCH₂ | OCH₂CH=CH₂ | H | Oil |
| 555 | t-Bu | Cl | S | H | Me / 4-OCHCH₂ | OCH₂CH=CH₂ | H | Oil |
| 556 | t-Bu | Br | O | H | Me / 4-OCHCH₂ | OCH₂CH=CH₂ | H | |
| 557 | Pro | Cl | O | H | Me / 4-OCHCH₂ | OCH₂CH=CHCH₃ | H | |
| 558 | t-Bu | Cl | O | H | Me / 4-OCHCH₂ | OCH₂CH=CHCH₃ | H | |
| 559 | t-Bu | Cl | S | H | Me / 4-OCHCH₂ | OCH₂CH=CHCH₃ | H | |
| 560 | t-Bu | Cl | O | H | Me / 3-OCHCH₂ | OCH₂CH=CHCH₃ | H | |
| 561 | t-Bu | Cl | O | H | Me / 4-OCHCH₂ | OCH₂C≡CH | H | |
| 562 | t-Bu | Cl | S | H | Me / 4-OCHCH₂ | OCH₂C≡CH | H | |

TABLE 1-continued

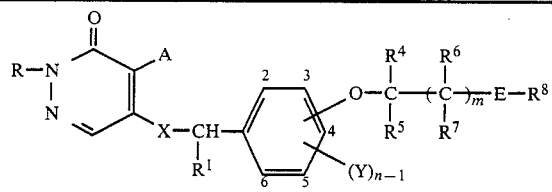

| No. | R | A | X | R¹ | O-C(R⁴)(R⁵)-(C(R⁶)(R⁷))ₘ | ER⁸ | (Y)ₙ₋₁ | M.P. (°C.) |
|---|---|---|---|---|---|---|---|---|
| 563 | t-Bu | Cl | O | H | 4-OCHCH₂ \| Me | OCH₂C≡CCH₃ | H | |
| 564 | t-Bu | Cl | O | H | 4-OCHCH₂ \| Me | O-cyclopropyl(H) | H | |
| 565 | t-Bu | Cl | S | H | 4-OCHCH₂ \| Me | O-cyclopropyl(H) | H | |
| 566 | t-Bu | Br | O | H | 4-OCHCH₂ \| Me | O-cyclopropyl(H) | H | |
| 567 | t-Bu | Br | O | H | 4-OCHCH₂ \| Me | O-cyclopentyl(H) | H | |
| 568 | t-Bu | Cl | O | H | 4-OCHCH₂ \| Me | O-cyclopentyl(H) | H | |
| 569 | t-Bu | Cl | S | H | 4-OCHCH₂ \| Me | O-cyclopentyl(H) | H | |
| 570 | t-Bu | Cl | S | H | 4-OCHCH₂ \| Me | O-cyclohexyl(H) | H | |
| 571 | t-Bu | Cl | O | H | 4-OCHCH₂ \| Me | O-cyclohexyl(H) | H | |
| 572 | t-Bu | Br | S | H | 3-OCHCH₂ \| Me | O-cyclohexyl(H) | H | |
| 573 | t-Bu | Me | O | H | 4-OCH₂CH \| Me | OMe | H | |
| 574 | t-Bu | Me | S | H | 4-OCH₂CH \| Me | OMe | H | |
| 575 | t-Bu | Cl | S | H | 4-OCH₂CH \| Me | OMe | H | |
| 576 | t-Bu | Cl | O | H | 4-OCH₂CH \| Me | OMe | H | |
| 577 | Pro | Br | S | Me | 4-OCH₂CH \| Me | OEt | H | |
| 578 | t-Bu | Et | O | E | 4-OCH₂CH \| Me | OEt | H | |
| 579 | t-Bu | Cl | O | H | 4-OCH₂CH \| Me | OEt | H | Oil |
| 580 | t-Bu | Cl | S | H | 4-OCH₂CH \| Me | OEt | H | |
| 581 | t-Bu | Cl | O | H | 4-OCH₂CH \| Me | OPro | H | Oil |

TABLE 1-continued

| No. | R | A | X | R¹ | O–C(R⁴)(R⁵)–(C(R⁶)(R⁷))ₘ | ER⁸ | (Y)ₙ₋₁ | M.P. (°C.) |
|-----|---|---|---|-----|--------------------------|-----|--------|-----------|
| 582 | t-Bu | Cl | S | H | 4-OCH₂CH(Me) | OPro | H | Oil |
| 583 | t-Bu | Br | O | H | 4-OCH₂CH(Me) | OPro | H | |
| 584 | t-Bu | Cl | O | H | 4-OCH₂CH(Me) | OPro | 3-Me | |
| 585 | t-Bu | Me | S | H | 4-OCH₂CH(Me) | OPro | H | |
| 586 | t-Bu | Me | O | H | 4-OCH₂CH(Me) | OPro | H | |
| 587 | t-Bu | Br | O | H | 4-OCH₂CH(Me) | OBu | H | |
| 588 | t-Bu | Cl | O | H | 4-OCH₂CH(Me) | OBu | H | |
| 589 | t-Bu | Cl | O | H | 4-OCH₂CH(Me) | OBu–i | H | |
| 590 | t-Bu | Cl | S | Me | 4-OCH₂CH(Me) | OBu–i | H | |
| 591 | t-Bu | Cl | O | H | 4-OCH₂CH(Me) | OPen | H | |
| 592 | t-Bu | Cl | O | H | 4-OCH₂CH(Me) | OPen | H | |
| 593 | t-Bu | Cl | O | H | 4-OCH₂CH(Me) | OPen-i | H | |
| 594 | t-Bu | Cl | O | H | 4-OCH₂CH(Me) | OHex | H | |
| 595 | t-Bu | Cl | O | H | 4-OCH₂CH(Me) | OCH₂CH=CH₂ | H | |
| 596 | t-Bu | Cl | S | H | 4-OCH₂CH(Me) | OCH₂CH=CH₂ | H | |
| 597 | t-Bu | Me | O | H | 4-OCH₂CH(Me) | OCH₂CH=CH₂ | H | |
| 598 | t-Bu | Br | O | H | 4-OCH₂CH(Me) | OCH₂CH=CHCH₃ | H | |
| 599 | t-Bu | Cl | O | H | 4-OCH₂CH(Me) | OCH₂CH=CHCH₃ | H | |
| 600 | t-Bu | Cl | O | H | 4-OCH₂CH(Me) | OCH₂C≡CH | H | |
| 601 | t-Bu | Cl | S | H | 4-OCH₂CH(Me) | OCH₂C≡CH | H | |
| 602 | t-Bu | Br | O | H | 4-OCH₂CH(Me) | OCH₂C≡CH | H | |
| 603 | t-Bu | Cl | O | H | 4-OCH₂CH(Me) | OCH₂C≡CCH₃ | H | |
| 604 | t-Bu | Cl | S | H | 4-OCH₂CH(Me) | OCH₂C≡CCH₃ | H | |
| 605 | t-Bu | Cl | S | H | 4-OCH₂CH(Me) | OCH(CH₃)CH=CH₂ | H | |

TABLE 1-continued

| No. | R | A | X | R¹ | O—C(R⁴)(R⁵)—(C(R⁶)(R⁷))ₘ | ER⁸ | $(Y)_{n-1}$ | M.P. (°C.) |
|---|---|---|---|---|---|---|---|---|
| 606 | t-Bu | Cl | O | H | 4-OCH₂CH(Me) | CH₃ \| OCHCH=CH₂ | H | |
| 607 | t-Bu | Cl | O | H | 4-OCH₂CH(Me) | OCH₂CH=C(CH₃)(CH₃) | H | |
| 608 | t-Bu | Cl | O | H | 4-OC(CH₃)₂CH₂ | OMe | H | |
| 609 | t-Bu | Cl | S | H | 4-OC(CH₃)₂CH₂ | OMe | H | |
| 610 | Pro | Cl | O | H | 4-OC(CH₃)₂CH₂ | OEt | H | |
| 611 | t-Bu | Cl | O | H | 4-OC(CH₃)₂CH₂ | OEt | H | Oil |
| 612 | t-Bu | Cl | S | H | 4-OC(CH₃)₂CH₂ | OEt | H | Oil |
| 613 | t-Bu | Me | O | H | 4-OC(CH₃)₂CH₂ | OEt | H | |
| 614 | t-Bu | Br | O | H | 4-OC(CH₃)₂CH₂ | OPro | H | |
| 615 | t-Bu | Cl | O | H | 4-OC(CH₃)₂CH₂ | OPro | H | Oil |
| 616 | t-Bu | Cl | S | H | 4-OC(CH₃)₂CH₂ | OPro | H | Oil |
| 617 | Pen | Cl | O | H | 4-OC(CH₃)₂CH₂ | OPro | H | |
| 618 | t-Bu | Cl | O | H | 4-OC(CH₃)₂CH₂ | OPro—i | H | |
| 619 | t-Bu | Cl | S | H | 4-OC(CH₃)₂CH₂ | OPro—i | H | |
| 620 | t-Bu | Cl | S | H | 4-OC(CH₃)₂CH₂ | OBu | H | |
| 621 | t-Bu | Cl | O | H | 4-OC(CH₃)₂CH₂ | OBu | H | |
| 622 | t-Bu | Cl | O | H | 4-OC(CH₃)₂CH₂ | OBu—i | H | |
| 623 | t-Bu | Cl | S | H | 4-OC(CH₃)₂CH₂ | OBu—i | H | |
| 624 | t-Bu | Me | O | H | 4-OC(CH₃)₂CH₂ | OPro—i | H | |
| 625 | t-Bu | Me | S | H | 4-OC(CH₃)₂CH₂ | OPro—i | H | |
| 626 | t-Bu | Cl | O | H | 4-OC(CH₃)₂CH₂ | OCH₂C=CH₂ | H | |
| 627 | t-Bu | Cl | S | H | 4-OC(CH₃)₂CH₂ | OCH₂C=CH₂ | H | |
| 628 | t-Bu | Cl | O | H | 4-OC(CH₃)₂CH₂ | OCH₂CH=CHCH₃ | H | |
| 629 | t-Bu | Cl | O | H | 4-OC(CH₃)₂CH₂ | OCH₂C≡CH | H | |
| 630 | t-Bu | Cl | S | H | 4-OC(CH₃)₂CH₂ | OCH₂C≡CH | H | |
| 631 | t-Bu | Cl | S | H | 4-OC(CH₃)₂CH₂ | O—cyclopropyl(H) | H | |
| 632 | t-Bu | Cl | O | H | 4-OC(CH₃)₂CH₂ | O—cyclopropyl(H) | H | |
| 633 | t-Bu | Cl | O | H | 4-OC(CH₃)₂CH₂ | O—cyclopentyl(H) | H | |
| 634 | t-Bu | Cl | S | Me | 4-OC(CH₃)₂CH₂ | O—cyclopentyl(H) | H | |
| 635 | t-Bu | Cl | O | H | 4-OC(CH₃)₂CH₂ | OMe | H | |
| 636 | t-Bu | Cl | S | H | 4-OCHCH(Me)(Me) | OMe | H | |
| 637 | t-Bu | Cl | O | H | 4-OCHCH(Me)(Me) | OMe | H | 78.4~80.1 |
| 638 | t-Bu | Me | O | H | 4-OCHCH(Me)(Me) | OMe | H | |
| 639 | t-Bu | Cl | S | H | 4-OCHCH(Me)(Me) | OMe | H | Oil |
| 640 | t-Bu | Cl | O | H | 4-OCHCH(Me)(Me) | OEt | H | |
| 641 | t-Bu | Cl | S | H | 4-OCHCH(Me)(Me) | OEt | H | |
| 642 | t-Bu | Me | O | H | 4-OCHCH(Me)(Me) | OEt | H | |

TABLE 1-continued

Structure:

$$\text{R-N-N=... (pyridazinone core with substituents A, X-CHR}^1\text{-phenyl-O-C(R}^4\text{)(R}^5\text{)-(C(R}^6\text{)(R}^7\text{))}_m\text{-E-R}^8\text{, (Y)}_{n-1})$$

| No. | R | A | X | R¹ | O—C(R⁴)(R⁵)—(C(R⁶)(R⁷))ₘ | ER⁸ | (Y)ₙ₋₁ | M.P. (°C.) |
|-----|---|---|---|----|--------------------------|-----|--------|------------|
| 643 | t-Bu | Me | S | H | Me Me / 4-OCHCH | OEt | H | |
| 644 | t-Bu | Cl | O | H | Me Me / 4-OCHCH | OPro | H | |
| 645 | t-Bu | Cl | S | H | Me Me / 4-OCHCH | OPro | H | |
| 646 | t-Bu | Me | S | H | Me Me / 4-OCHCH | OPro | H | |
| 647 | t-Bu | Cl | S | H | Me Me / 4-OCHCH | OBu | H | |
| 648 | t-Bu | Br | O | H | Me Me / 4-OCHCH | OBu—i | H | |
| 649 | t-Bu | Cl | S | H | Me Me / 4-OCHCH | OBu—i | H | |
| 650 | t-Bu | Cl | O | H | Me Me / 4-OCHCH | OCH₂CH=CH₂ | H | |
| 651 | t-Bu | Cl | S | H | Me Me / 4-OCHCH | OCH₂CH=CH₂ | H | |
| 652 | t-Bu | Me | S | H | Me Me / 4-OCHCH | OCH₂CH=CH₂ | H | |
| 653 | t-Bu | Cl | O | H | Me Me / 4-OCHCH | OCH₂C≡CH | H | |
| 654 | t-Bu | Cl | S | H | Me Me / 4-OCHCH | OCH₂C≡CH | H | |
| 655 | t-Bu | Me | S | H | Me Me / 4-OCHCH | OCH₂C≡CH | H | |
| 656 | t-Bu | Cl | O | H | Me Me / 4-OCHCH | OCH₂CH=C(CH₃)(CH₃) | H | |
| 657 | t-Bu | Cl | O | H | Me Me / 4-OCHCH | OCH₂C≡CCH₃ | H | |
| 658 | i-Pro | Cl | O | H | Et / 4-OCHCH₂ | OMe | H | 128.5~129.6 |
| 659 | t-Bu | Cl | O | H | Et / 4-OCHCH₂ | OMe | H | Oil |
| 660 | t-Bu | Br | O | H | Et / 4-OCHCH₂ | OMe | H | |
| 661 | t-Bu | Cl | S | H | Et / 4-OCHCH₂ | OMe | H | Oil |
| 662 | t-Bu | Me | O | H | Et / 4-OCHCH₂ | OMe | H | |
| 663 | Pro | Cl | O | H | Et / 4-OCHCH₂ | OEt | H | 72.0~74.0 |
| 664 | t-Bu | Cl | O | H | Et / 4-OCHCH₂ | OEt | H | Oil |
| 665 | t-Bu | Me | O | H | Et / 4-OCHCH₂ | OEt | H | |

TABLE 1-continued

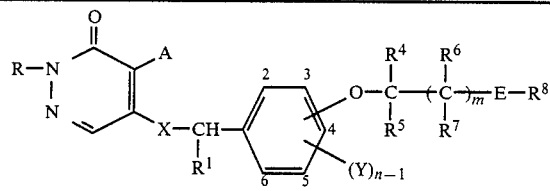

| No. | R | A | X | R¹ | O-C(R⁴)(R⁵)-(C(R⁶)(R⁷))ₘ | ER⁸ | (Y)ₙ₋₁ | M.P. (°C.) |
|---|---|---|---|---|---|---|---|---|
| 666 | t-Bu | Me | S | H | 4-OCHCH₂ / Et | OEt | H | |
| 667 | t-Bu | Cl | S | H | 4-OCHCH₂ / Et | OEt | H | 46.0~53.0 |
| 668 | t-Bu | Cl | O | H | 4-OCHCH₂ / Et | OPro | H | Oil |
| 669 | t-Bu | Br | O | H | 4-OCHCH₂ / Et | OPro | H | |
| 670 | t-Bu | Br | S | H | 4-OCHCH₂ / Et | OPro | H | |
| 671 | t-Bu | Cl | S | H | 4-OCHCH₂ / Et | OPro | H | Oil |
| 672 | Et | Cl | O | H | 4-OCHCH₂ / Et | OBu | H | |
| 673 | t-Bu | Cl | O | H | 4-OCHCH₂ / Et | OBu | H | Oil |
| 674 | t-Bu | Br | O | H | 4-OCHCH₂ / Et | OBu | H | |
| 675 | t-Bu | Cl | S | H | 4-OCHCH₂ / Et | OBu | H | 43.0~46.0 |
| 676 | t-Bu | Cl | S | H | 4-OCHCH₂ / Et | OBu—i | H | |
| 677 | t-Bu | Cl | O | H | 4-OCHCH₂ / Et | OBu—i | H | |
| 678 | t-Bu | Cl | O | H | 4-OCHCH₂ / Et | OBu—s | H | |
| 679 | t-Bu | Cl | S | H | 4-OCHCH₂ / Et | OBu—s | H | |
| 680 | t-Bu | Cl | O | H | 4-OCHCH₂ / Et | OPen | H | |
| 681 | t-Bu | Cl | O | H | 4-OCHCH₂ / Et | OCH₂CH=CH₂ | H | |
| 682 | t-Bu | Cl | S | H | 4-OCHCH₂ / Et | OCH₂CH=CH₂ | H | |
| 683 | t-Bu | Cl | O | H | 4-OCHCH₂ / Et | OCH₂CH=CHCH₃ | H | |
| 684 | t-Bu | Cl | S | H | 4-OCHCH₂ / Et | OCH₂CH=CHCH₃ | H | |
| 685 | t-Bu | Cl | S | H | 4-OCHCH₂ / Et | OCH₂C≡CH | H | |
| 686 | t-Bu | Cl | O | H | 4-OCHCH₂ / Et | OCH₂C≡CH | H | |
| 687 | t-Bu | Br | O | H | 4-OCHCH₂ / Et | OCH₂C≡CH | H | |
| 688 | t-Bu | Cl | O | H | 4-OCHCH₂ / Et | O—▷H (cyclopropyl) | H | |

TABLE 1-continued

| No. | R | A | X | R¹ | O–C(R⁴)(R⁵)–(C(R⁶)(R⁷))ₘ | ER⁸ | (Y)ₙ₋₁ | M.P. (°C.) |
|---|---|---|---|---|---|---|---|---|
| 689 | t-Bu | Cl | S | H | Et / 4-OCHCH₂ | O–cyclopropyl–H | H | |
| 690 | t-Bu | Cl | S | H | Et / 4-OCHCH₂ | O–cyclopentyl–H | H | |
| 691 | t-Bu | Cl | O | H | Et / 4-OCHCH₂ | O–cyclopentyl–H | H | |
| 692 | t-Bu | Cl | O | H | Et / 4-OCHCH₂ | O–cyclohexyl–H | H | |
| 693 | t-Bu | Me | S | H | Pro / 4-OCHCH₂ | OMe | H | |
| 694 | t-Bu | Cl | S | H | Pro / 4-OCHCH₂ | OMe | H | |
| 695 | t-Bu | Cl | O | H | Pro / 4-OCHCH₂ | OMe | H | |
| 696 | t-Bu | Br | O | H | Pro / 4-OCHCH₂ | OMe | H | |
| 697 | t-Bu | Cl | O | H | Pro / 4-OCHCH₂ | OEt | H | |
| 698 | t-Bu | Cl | S | H | Pro / 4-OCHCH₂ | OEt | H | |
| 699 | t-Bu | Cl | S | H | Pro / 4-OCHCH₂ | OPro | H | |
| 700 | t-Bu | Cl | O | H | Pro / 4-OCHCH₂ | OPro | H | |
| 701 | Bu | Cl | O | H | Pro / 4-OCHCH₂ | OBu | 3-Me | |
| 702 | t-Bu | Cl | O | H | Pro / 4-OCHCH₂ | OBu—i | H | |
| 703 | t-Bu | Cl | S | H | Pro / 4-OCHCH₂ | OBu—i | H | |
| 704 | t-Bu | Cl | S | H | Pro / 4-OCHCH₂ | OBu—s | H | |
| 705 | t-Bu | Cl | S | H | Pro / 4-OCHCH₂ | O–cyclopropyl–H | H | |
| 706 | t-Bu | Cl | O | H | Pro / 4-OCHCH₂ | O–cyclopropyl–H | H | |
| 707 | t-Bu | Cl | O | H | Pro / 4-OCHCH₂ | O–cyclopentyl–H | H | |

TABLE 1-continued

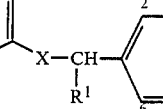

| No. | R | A | X | R¹ | O—C(R⁴)(R⁵)—(C(R⁶)(R⁷))ₘ | ER⁸ | (Y)ₙ₋₁ | M.P. (°C.) |
|---|---|---|---|---|---|---|---|---|
| 708 | t-Bu | Cl | S | H | Pro<br>4-OCHCH₂ | 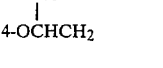 | H | |
| 709 | t-Bu | Cl | O | H | Pro<br>4-OCHCH₂ | 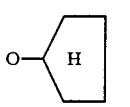 | H | |
| 710 | Bu | Cl | O | H | Pro<br>4-OCHCH₂ | OCH₂CH=CH₂ | H | |
| 711 | t-Bu | Cl | S | H | Pro<br>4-OCHCH₂ | OCH₂CH=CH₂ | H | |
| 712 | t-Bu | Cl | O | H | Pro<br>4-OCHCH₂ | OCH₂CH=CHCH₃ | H | |
| 713 | t-Bu | Br | O | H | Pro<br>4-OCHCH₂ | OCH₂CH=CHCH₃ | H | |
| 714 | t-Bu | Cl | O | H | Pro<br>4-OCHCH₂ | OCH₂C≡CH | H | |
| 715 | t-Bu | Cl | S | H | Pro<br>4-OCHCH₂ | OCH₂C≡CH | H | |
| 716 | t-Bu | Cl | S | H | CH₃<br>4-OCHCH₂ | OCH₂C≡CCH₃ | H | |
| 717 | t-Bu | Cl | O | H | CH₃<br>4-OCHCH₂ | SOEt | H | |
| 718 | t-Bu | Cl | O | H | CH₃<br>4-OCHCH₂ | SO₂Et | H | |
| 719 | t-Bu | Cl | S | H | CH₃<br>4-OCHCH₂ | OCH₂C≡CCH₃ | H | |
| 720 | t-Bu | Pro | S | H | Bu<br>4-OCHCH₂ | OMe | H | |
| 721 | t-Bu | Cl | O | H | Bu<br>4-OCHCH₂ | OMe | H | |
| 722 | t-Bu | Cl | S | H | Bu<br>4-OCHCH₂ | OMe | H | |
| 723 | t-Bu | Cl | O | H | Bu<br>4-OCHCH₂ | OEt | H | |
| 724 | t-Bu | Cl | S | H | Bu<br>4-OCHCH₂ | OEt | H | |
| 725 | t-Bu | Cl | O | H | Bu<br>4-OCHCH₂ | OPro | H | |
| 726 | t-Bu | Cl | S | H | Bu<br>4-OCHCH₂ | OPro | H | |
| 727 | t-Bu | Cl | O | H | Bu<br>4-OCHCH₂ | OPro—i | H | |
| 728 | t-Bu | Cl | S | H | Bu<br>4-OCHCH₂ | OPro—i | H | |

TABLE 1-continued

Structure:

R-N(N=)-C(=O)-C(A)=C(X-CH(R¹)-C₆H₃(Y)ₙ₋₁-O-C(R⁴)(R⁵)-(C(R⁶)(R⁷))ₘ-E-R⁸

| No. | R | A | X | R¹ | O-C(R⁴)(R⁵)-(C(R⁶)(R⁷))ₘ | ER⁸ | (Y)ₙ₋₁ | M.P. (°C.) |
|---|---|---|---|---|---|---|---|---|
| 729 | t-Bu | Cl | O | H | Bu / 4-OCHCH₂ | O-cyclopropyl(H) | H | |
| 730 | t-Bu | Cl | O | H | Bu / 4-OCHCH₂ | O-cyclopentyl(H) | H | |
| 731 | t-Bu | Cl | O | H | Bu / 4-OCHCH₂ | OCH₂CH=CH₂ | H | |
| 732 | t-Bu | Cl | O | H | Et / 4-OCHCH₂ | SMe | H | |
| 733 | t-Bu | Cl | O | H | Et / 4-OCHCH₂ | SEt | H | |
| 734 | t-Bu | Cl | S | H | Et / 4-OCHCH₂ | OPro—i | H | |
| 735 | t-Bu | Cl | S | H | Et / 4-OCHCH₂ | OPro—i | 3-F | |
| 736 | t-Bu | Cl | O | H | Et / 4-OCHCH₂ | OPro—i | H | |
| 737 | Et | Cl | S | H | Me / 4-OCHCH₂ | SMe | H | |
| 738 | t-Bu | Cl | O | H | Me / 4-OCHCH₂ | SMe | H | |
| 739 | t-Bu | Cl | S | H | Me / 4-OCHCH₂ | SMe | H | |
| 740 | t-Bu | Cl | O | H | Me / 4-OCHCH₂ | SEt | H | |
| 741 | t-Bu | Cl | S | H | Me / 4-OCHCH₂ | SEt | H | |
| 742 | t-Bu | Cl | O | H | Me / 4-OCHCH₂ | SEt | H | |
| 743 | t-Bu | Cl | O | H | Me / 4-OCHCH₂ | SPro | H | |
| 744 | t-Bu | Cl | S | H | Me / 4-OCHCH₂ | SPro | H | |
| 745 | t-Bu | Cl | O | H | Me / 4-OCHCH₂ | SPro—i | H | |
| 746 | t-Bu | Cl | S | H | Me / 4-OCHCH₂ | SPro—i | H | |
| 747 | t-Bu | Br | O | H | 4-OC(CH₃)₂CH₂ | SPro—i | H | |
| 748 | t-Bu | Cl | S | H | Et / 3-OCHCH₂ | SPro—i | H | |
| 749 | Pro | Cl | O | H | Me / 4-OCHCH₂ | SBu | H | |
| 750 | t-Bu | Cl | O | H | Me / 4-OCHCH₂ | SBu | H | |
| 751 | t-Bu | Cl | S | H | Me / 4-OCHCH₂ | SBu | H | |

TABLE 1-continued

Structure with substituents: R-N-N=... pyridazinone ring with A, X-CH(R¹)-phenyl(Y)ₙ₋₁-O-C(R⁴)(R⁵)-(C(R⁶)(R⁷))ₘ-E-R⁸

The R¹ column shows -O-C(R⁴)(R⁵)-(C(R⁶)(R⁷))ₘ- group attached to phenyl.

| No. | R | A | X | R¹ | (R¹ attachment) | ER⁸ | (Y)ₙ₋₁ | M.P. (°C.) |
|-----|---|---|---|----|-----|------|--------|-----------|
| 752 | t-Bu | Cl | S | H | 3-OCH(Me)CH₂ | SBu | H | |
| 753 | t-Bu | Me | O | H | 4-OCH₂CH₂CH₂ | SMe | H | |
| 754 | t-Bu | Cl | S | H | 4-OCH₂CH₂CH₂ | SMe | H | |
| 755 | t-Bu | Cl | O | H | 4-OCH₂CH₂CH₂ | SOMe | H | |
| 756 | t-Bu | Cl | O | H | 4-OCH₂CH₂CH₂ | SO₂Me | H | |
| 757 | t-Bu | Cl | S | H | 4-OCH₂CH₂CH₂ | SOMe | H | |
| 758 | t-Bu | Cl | S | H | 4-OCH₂CH₂CH₂ | SO₂Me | H | |
| 759 | t-Bu | Cl | O | H | 4-OCH₂CH₂CH₂ | SEt | H | |
| 760 | t-Bu | Cl | O | H | 4-OCH₂CH₂CH₂ | SOEt | H | |
| 761 | t-Bu | Cl | O | H | 4-OCH₂CH₂CH₂ | SO₂Et | H | |
| 762 | t-Bu | Cl | S | H | 4-OCH₂CH₂CH₂ | SEt | H | |
| 763 | t-Bu | Cl | O | H | 4-OCH₂CH₂CH₂ | SPro | H | |
| 764 | t-Bu | Cl | S | H | 4-OCH₂CH₂CH₂ | SPro | H | |
| 765 | t-Bu | Cl | O | H | 4-OCH₂CH₂CH₂ | SPro—i | H | |
| 766 | t-Bu | Cl | O | H | 4-OCH₂CH₂CH₂ | SOPro—i | H | |
| 767 | t-Bu | Cl | O | H | 4-OCH₂CH₂CH₂ | SO₂Pro—i | H | |
| 768 | t-Bu | Pro | S | H | 4-OCH₂CH₂CH₂ | SBu | H | |
| 769 | t-Bu | Cl | O | H | 4-OC₂H₄ | NMe₂ | H | |
| 770 | t-Bu | Me | O | H | 4-OC₂H₄ | NMe₂ | H | |
| 771 | t-Bu | Cl | S | H | 4-OC₂H₄ | NMe₂ | H | |
| 772 | t-Bu | Cl | S | H | 4-OCH(Me)CH₂ | NMe₂ | H | |
| 773 | t-Bu | Cl | O | H | 4-OCH(Me)CH₂ | NMe₂ | H | |
| 774 | t-Bu | Me | S | H | 4-OCH(Me)CH₂ | NMe₂ | H | |
| 775 | t-Bu | Cl | S | H | 3-OCH(Me)CH₂ | NMe₂ | H | |
| 776 | t-Bu | Me | O | H | 4-OCH₂CH(Me) | NMe₂ | H | |
| 777 | t-Bu | Me | S | H | 4-OCH₂CH(Me) | NMe₂ | H | |
| 778 | t-Bu | Cl | O | H | 4-OCH₂CH(Me) | NMe₂ | H | |
| 779 | t-Bu | Cl | S | H | 4-OCH₂CH(Me) | NMe₂ | H | |
| 780 | t-Bu | Cl | O | H | 4-OCH₂C(CH₃)₂ | NMe₂ | H | |
| 781 | t-Bu | Cl | S | H | 4-OCH₂C(CH₃)₂ | NMe₂ | H | |
| 782 | t-Bu | Cl | O | H | 4-OCH₂CH₂CH₂ | NMe₂ | H | |
| 783 | t-Bu | Me | S | H | 4-OCH₂CH₂CH₂ | NMe₂ | H | |
| 784 | t-Bu | Cl | S | H | 4-OCH₂CH₂CH₂ | NMe₂ | H | |
| 785 | t-Bu | Et | O | H | 4-OCH₂CH₂CH₂ | NMe₂ | H | |
| 786 | t-Bu | Cl | O | H | 4-OC₂H₄ | NEt₂ | H | 55.0~56.0 |
| 787 | t-Bu | Cl | S | H | 4-OC₂H₄ | NEt₂ | H | Oil |
| 788 | t-Bu | Br | O | H | 4-OC₂H₄ | NEt₂ | H | |
| 789 | t-Bu | Cl | O | Me | 4-OC₂H₄ | NEt₂ | H | Oil |
| 790 | t-Bu | Cl | O | H | 3-OCH₂CH₂CH₂ | NEt₂ | H | |
| 791 | t-Bu | Cl | O | H | 4-OCH₂CH₂CH₂ | NEt₂ | H | |
| 792 | t-Bu | Cl | S | H | 4-OCH₂CH₂CH₂ | NEt₂ | H | |
| 793 | t-Bu | Cl | O | H | 4-OCH(Me)CH₂ | NEt₂ | H | |
| 794 | t-Bu | Cl | S | H | 4-OCH(Me)CH₂ | NEt₂ | H | |
| 795 | t-Bu | Me | O | H | 4-OCH₂CH(Me) | NEt₂ | H | |

TABLE 1-continued

| No. | R | A | X | R¹ | $\underset{R^5}{\overset{R^4}{\underset{|}{O-C}}}\underset{R^7}{\overset{R^6}{(\underset{|}{C})_m}}$ | ER⁸ | $(Y)_{n-1}$ | M.P. (°C.) |
|---|---|---|---|---|---|---|---|---|
| 796 | t-Bu | Cl | O | H | 4-OCH₂CH(Me) | NEt₂ | H | |
| 797 | t-Bu | Cl | S | H | 4-OCH₂CH(Me) | NEt₂ | H | |
| 798 | t-Bu | Cl | O | H | 4-OCH₂C(CH₃)₂ | NEt₂ | H | |
| 799 | t-Bu | Cl | S | H | 4-OCH₂C(CH₃)₂ | NEt₂ | H | |
| 800 | t-Bu | Cl | O | H | 4-OC₂H₄ | NPro₂ | H | |
| 801 | t-Bu | Cl | S | H | 4-OC₂H₄ | NPro₂ | H | |
| 802 | t-Bu | Me | S | H | 4-OCH₂CH₂CH₂ | NPro₂ | H | |
| 803 | t-Bu | Cl | O | H | 4-OCH₂CH₂CH₂ | NPro₂ | H | |
| 804 | t-Bu | Et | S | H | 4-OCH₂CH₂CH₂ | NPro₂ | H | |
| 805 | t-Bu | Cl | O | H | 4-OCHCH₂(Me) | NPro₂ | H | |
| 806 | t-Bu | Cl | S | H | 4-OCHCH₂(Me) | NPro₂ | H | |
| 807 | t-Bu | Cl | O | H | 4-OCH₂CH(Me) | NPro₂ | H | |
| 808 | t-Bu | Cl | S | H | 4-OCH₂CH(Me) | NPro₂ | H | |
| 809 | t-Bu | Br | S | H | 4-OC₂H₄ | NPro₂ | H | |
| 810 | t-Bu | Br | O | H | 4-OC₂H₄ | NPro₂ | H | |
| 811 | t-Bu | Cl | O | H | 4-OC₂H₄ | N(Pro—i)₂ | H | |
| 812 | t-Bu | Cl | O | H | 4-OCH₂CH₂CH₂ | N(Pro—i)₂ | H | |
| 813 | t-Bu | Cl | O | H | 4-OCHCH₂(Me) | N(Pro—i)₂ | H | |
| 814 | t-Bu | Me | S | H | 4-OCHCH₂(Me) | N(Pro—i)₂ | H | |
| 815 | t-Bu | Cl | O | H | 4-OCH₂CH(Me) | N(Pro—i)₂ | H | |
| 816 | t-Bu | Me | O | H | 4-OC₂H₄ | NBu₂ | H | |
| 817 | t-Bu | Cl | O | H | 4-OC₂H₄ | NBu₂ | H | |
| 818 | t-Bu | Cl | S | H | 4-OC₂H₄ | NBu₂ | H | |
| 819 | t-Bu | Cl | O | H | 4-OCH₂CH₂CH₂ | NBu₂ | H | |
| 820 | t-Bu | Cl | O | H | 4-OCHCH₂(Me) | NBu₂ | H | |
| 821 | t-Bu | Cl | S | H | 4-OCHCH₂(Me) | NBu₂ | H | |
| 822 | t-Bu | Cl | O | H | 4-OCH₂CH(Me) | NBu₂ | H | |
| 823 | t-Bu | Cl | O | H | 4-OC₂H₄ | N(Bu—i)₂ | H | |
| 824 | t-Bu | Cl | S | H | 4-OC₂H₄ | N(Bu—i)₂ | H | |
| 825 | t-Bu | Cl | O | H | 4-OCHCH₂(Me) | N(Bu—i)₂ | H | |
| 826 | t-Bu | Cl | S | H | 4-OCHCH₂(Me) | N(Bu—i)₂ | H | |
| 827 | t-Bu | Me | O | H | 4-OC₂H₄ | pyrrolidin-1-yl | H | |
| 828 | t-Bu | Cl | O | H | 4-OC₂H₄ | pyrrolidin-1-yl | H | |

TABLE 1-continued

Structure:

R−N(−N=)−C(=O)−C(A)=C(X−CHR¹−[phenyl(2,3,4,5,6) with (Y)ₙ₋₁]−O−C(R⁴)(R⁵)−[C(R⁶)(R⁷)]ₘ−E−R⁸)

Sub-column header: O−C(R⁴)(R⁵)−[C(R⁶)(R⁷)]ₘ−

| No. | R | A | X | R¹ | (O−C(R⁴)(R⁵)−[C(R⁶)(R⁷)]ₘ−) | ER⁸ | (Y)ₙ₋₁ | M.P. (°C.) |
|---|---|---|---|---|---|---|---|---|
| 829 | t-Bu | Cl | S | H | 4-OC₂H₄ | N-pyrrolidinyl | H | |
| 830 | t-Bu | Cl | O | H | 4-OCH₂CH₂CH₂ | N-pyrrolidinyl | H | |
| 831 | t-Bu | Cl | O | H | 4-OCHCH₂ (Me) | N-pyrrolidinyl | H | |
| 832 | t-Bu | Cl | S | H | 4-OCHCH₂ (Me) | N-pyrrolidinyl | H | |
| 833 | t-Bu | Cl | O | H | 4-OC₂H₄ | N-piperidinyl | H | |
| 834 | t-Bu | Pro | S | H | 4-OC₂H₄ | N-piperidinyl | H | |
| 835 | t-Bu | Cl | S | H | 4-OCHCH₂ (Me) | N-piperidinyl | H | |
| 836 | t-Bu | Cl | O | H | 4-OCHCH₂ (Me) | N-piperidinyl | H | |
| 837 | Pro | Cl | O | H | 4-OCH₂CH(OMe) | OMe | H | |
| 838 | t-Bu | Cl | O | H | 4-OCH₂CH(OMe) | OMe | H | 98.0∼101.0 |
| 839 | t-Bu | Cl | S | H | 4-OCH₂CH(OMe) | OMe | H | |
| 840 | t-Bu | Me | O | H | 4-OCH₂CH(OMe) | OMe | H | |
| 841 | t-Bu | Me | S | H | 4-OCH₂CH(OMe) | OMe | H | |
| 842 | Et | Cl | O | H | 4-OCH₂CH(OEt) | OEt | H | 84.8∼86.3 |
| 843 | t-Bu | Cl | O | H | 4-OCH₂CH(OEt) | OEt | H | 57.9∼63.0 |
| 844 | t-Bu | Cl | S | H | 4-OCH₂CH(OEt) | OEt | H | Oil |
| 845 | t-Bu | Br | O | H | 4-OCH₂CH(OEt) | OEt | H | |
| 846 | t-Bu | Me | O | H | 4-OCH₂CH(OEt) | OEt | H | |

TABLE 1-continued

| No. | R | A | X | R¹ | O-C(R⁴)(R⁵)-(C(R⁶)(R⁷))ₘ | ER⁸ | (Y)ₙ₋₁ | M.P. (°C.) |
|---|---|---|---|---|---|---|---|---|
| 847 | t-Bu | Cl | O | H | Pro, 4-OCH₂CH | OPro | H | |
| 848 | t-Bu | Cl | S | H | Pro, 4-OCH₂CH | OPro | H | |
| 849 | t-Bu | Me | O | H | Pro, 4-OCH₂CH | OPro | H | |
| 850 | t-Bu | Cl | O | H | Pro, 4-OCH₂CH | OPro | H | |

TABLE 2

| No. | R | A | X | R¹ | R² | B (Y)ₙ | m.p. (°C.) |
|---|---|---|---|---|---|---|---|
| 851 | Et | Cl | O | H | H | thiophene | 105.0~106.0 |
| 852 | t-Bu | Cl | O | H | H | thiophene | 102.0~103.5 |
| 853 | t-Bu | Cl | O | H | H | thiophene-F | |
| 854 | t-Bu | Br | O | H | H | thiophene-F | |
| 855 | t-Bu | Me | O | H | H | thiophene-F | |
| 856 | t-Bu | Cl | S | H | H | thiophene-F | |
| 857 | t-Bu | Cl | S | H | H | thiophene-Cl | oil |

TABLE 2-continued
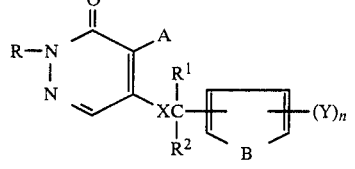
| No. | R | A | X | R¹ | R² | B | (°C.) |
|---|---|---|---|---|---|---|---|
| 858 | t-Bu | Cl | S | Me | H | 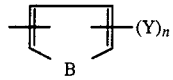 | oil |
| 859 | t-Bu | Me | S | H | H | 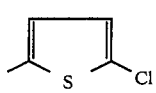 | |
| 860 | t-Bu | Cl | S | H | H | 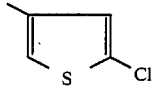 | oil |
| 861 | Et | Cl | S | H | H | 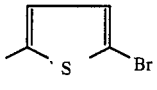 | oil |
| 862 | i-Pro | Br | O | H | H | 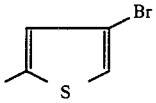 | |
| 863 | t-Bu | Cl | O | H | H | 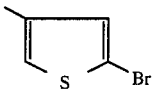 | |
| 864 | t-Bu | Et | S | H | H | 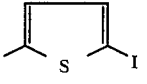 | |
| 865 | Et | Et | O | H | H | 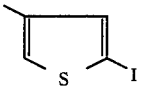 | |
| 866 | t-Bu | Cl | S | H | H | 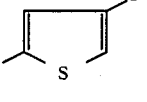 | |
| 867 | t-Bu | Me | S | H | H | 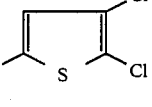 | |
| 868 | t-Bu | Pro | O | H | H | 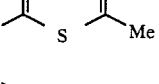 | |
| 869 | t-Bu | Cl | S | H | H | 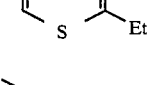 | |

TABLE 2-continued
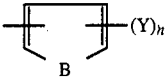
| No. | R | A | X | R¹ | R² | B(Y)n | (°C.) |
|---|---|---|---|---|---|---|---|
| 870 | t-Bu | Cl | S | H | H | 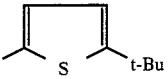 | oil |
| 871 | t-Bu | Cl | O | H | H | 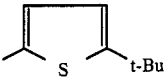 | |
| 872 | t-Bu | Me | S | H | H | 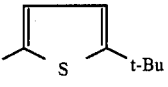 | oil |
| 873 | t-Bu | Me | S | Me | H | 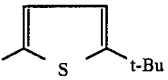 | m.p. |
| 874 | t-Bu | Cl | S | Me | H | 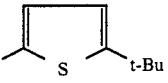 | |
| 875 | t-Bu | Cl | S | H | H | 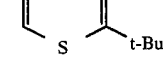 | |
| 876 | t-Bu | Cl | S | H | H | 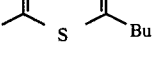 | oil |
| 877 | t-Bu | Me | O | H | H | 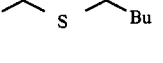 | |
| 878 | t-Bu | Cl | S | H | H | 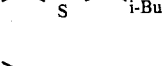 | |
| 879 | t-Bu | Cl | S | H | H | 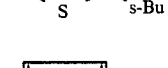 | |
| 880 | t-Bu | Cl | S | H | H |  | |
| 881 | t-Bu | Cl | S | H | H |  | |

TABLE 2-continued
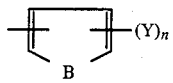
| No. | R | A | X | R¹ | R² | B-(Y)n | (°C.) |
|---|---|---|---|---|---|---|---|
| 882 | t-Bu | Me | S | H | H | thiophene with Br, t-Bu | |
| 883 | t-Bu | Cl | S | H | H | thiophene-cyclohexene (H) | oil |
| 884 | t-Bu | Me | O | H | H | thiophene-cyclohexene (H) | |
| 885 | t-Bu | Cl | S | H | H | thiophene-phenyl-Cl | oil |
| 886 | t-Bu | Me | S | H | H | thiophene-phenyl-Cl | |
| 887 | t-Bu | Cl | S | H | H | thiophene-phenyl | |
| 888 | t-Bu | Cl | O | H | H | thiophene-phenyl-F | |
| 889 | t-Bu | Me | O | H | H | thiophene-phenyl-F | |
| 890 | t-Bu | Cl | S | H | H | thiophene-CH₂-(2,4-diCl-phenyl) | oil |
| 891 | t-Bu | Me | S | H | H | thiophene-CH₂-phenyl | |

TABLE 2-continued
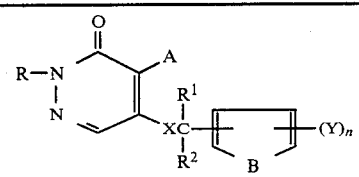
| No. | R | A | X | R¹ | R² | B-(Y)n | (°C.) |
|-----|---|---|---|----|----|--------|-------|
| 892 | t-Bu | Cl | S | H | H | 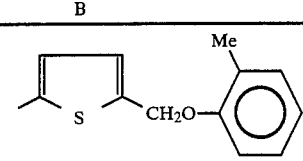 | |
| 893 | t-Bu | Me | S | H | H | 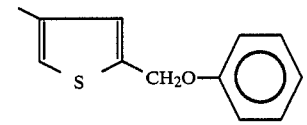 | |
| 894 | t-Bu | Cl | O | H | H | 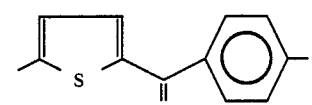 | |
| 895 | Et | Cl | O | H | H | 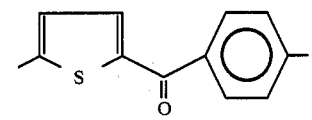 | 168.0~168.5 |
| 896 | Et | Br | O | H | H | 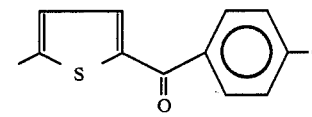 | |
| 897 | Pro | Cl | O | H | H | 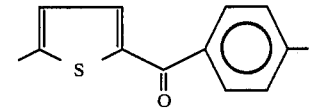 | |
| 898 | t-Bu | Cl | S | H | H | 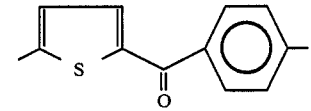 | 191.5~193.0 |
| 899 | Et | Cl | O | H | H | 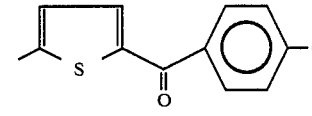 | |
| 900 | t-Bu | Me | S | H | H | 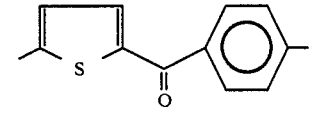 | |
| 901 | Et | Cl | O | H | H | 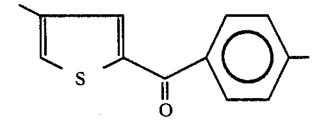 | |

TABLE 2-continued
| No. | R | A | X | R¹ | R² | B | (°C.) |
|---|---|---|---|---|---|---|---|
| 902 | t-Bu | Me | S | H | H | 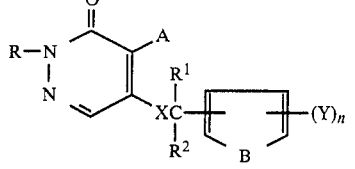 | |
| 903 | t-Bu | Cl | S | H | H | 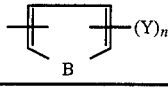 | |
| 904 | t-Bu | Cl | S | H | H | 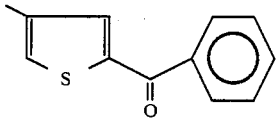 | |
| 905 | t-Bu | Cl | O | H | H | 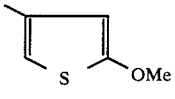 | |
| 906 | t-Bu | Cl | S | H | H | 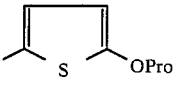 | |
| 907 | t-Bu | Cl | O | H | H | 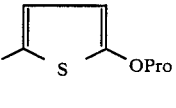 | |
| 908 | t-Bu | Cl | S | H | H | 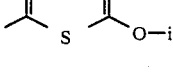 | |
| 909 | t-Bu | Cl | O | H | H | 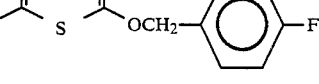 | |
| 910 | t-Bu | Cl | S | H | H | 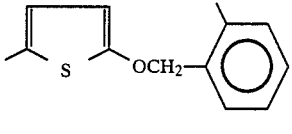 | |
| 911 | t-Bu | Cl | S | H | H | 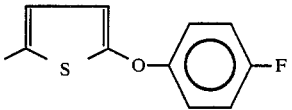 | |

TABLE 2-continued
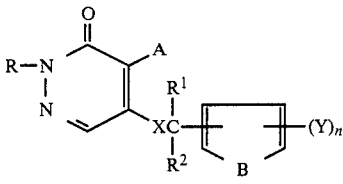
| No. | R | A | X | R¹ | R² | B | (°C.) |
|---|---|---|---|---|---|---|---|
| 912 | t-Bu | Cl | S | H | H | 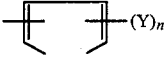 | |
| 913 | t-Bu | Cl | S | H | H | 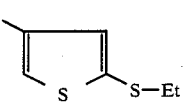 | |
| 914 | t-Bu | Cl | S | H | H |  | |
| 915 | t-Bu | Cl | O | H | H | 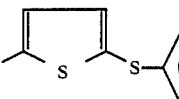 | |
| 916 | t-Bu | Cl | S | H | H |  | |
| 917 | t-Bu | Cl | S | H | H | 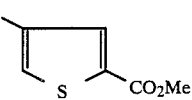 | |
| 918 | t-Bu | Cl | S | H | H |  | |
| 919 | t-Bu | Cl | S | H | H | 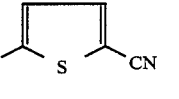 | |
| 920 | Et | Cl | O | H | H |  | 82.0~82.5 |
| 921 | t-Bu | Cl | O | H | H | 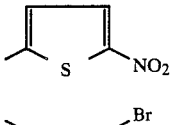 | 123.5~124.0 |
| 922 | Pro | Me | O | H | H |  | |
| 923 | Et | Br | O | H | H | 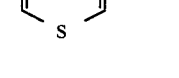 | |

TABLE 2-continued

| No. | R | A | X | R¹ | R² | B-(Y)n | (°C.) |
|---|---|---|---|---|---|---|---|
| 924 | t-Bu | Br | O | Me | H | furan-Me | |
| 925 | t-Bu | Cl | O | H | H | furan-Bu | |
| 926 | t-Bu | Et | O | H | H | furan-i-Bu | |
| 927 | t-Bu | Me | O | H | H | furan-t-Bu | |
| 928 | t-Bu | Cl | O | H | H | furan-$CF_3$ | |
| 929 | Et | Cl | O | H | H | furan-CH$_2$-Ph | 96.0~97.0 |
| 930 | t-Bu | Cl | O | H | H | furan-CH$_2$-Ph | oil |
| 931 | t-Bu | Me | S | H | H | furan-(4-Cl-Ph) | |
| 932 | Et | Cl | O | H | H | furan-C(O)-(4-$CF_3$-Ph) | |
| 933 | $C_6H_{13}$ | Cl | O | Me | H | MeO-furan | |
| 934 | t-Bu | Cl | O | H | H | furan-O-(2-Cl-4-$CF_3$-Ph) | |

TABLE 2-continued

Structure:

R–N(–N=)–C(=O)– ring with A substituent, connected via C(R¹)(R²)–X– to ring B with (Y)n substituents.

| No. | R | A | X | R¹ | R² | B ring with (Y)n | (°C.) |
|-----|---|---|---|----|----|------------------|-------|
| 935 | i-Bu | Cl | S | H | H | 5-nitro-furan-2-yl | |
| 936 | t-Bu | Me | S | H | H | 4-t-Bu-furan-2-yl | |
| 937 | Pro | Cl | S | H | H | 3-t-Bu-furan-2-yl | |
| 938 | Et | Cl | S | H | H | 1-Me-pyrrol-2-yl | |
| 939 | Bu | Cl | O | H | H | 1-Me-pyrrol-2-yl | |
| 940 | Et | Cl | O | H | H | 1,2-diMe-pyrrol-... (3-Me, 2-Me on N-Me pyrrole) | |
| 941 | t-Bu | Me | O | H | H | 4-Me-5-(phenylthio)-1H-pyrrol-2-yl | |
| 942 | t-C₅H₁₁ | Cl | O | H | H | 5-chloro-1-Me-pyrrol-2-yl | |
| 943 | t-Bu | Pro | O | Me | H | 1-Me-pyrrol-2-yl | |
| 944 | t-Bu | Cl | S | H | H | 5-fluoro-pyridin-2-yl | |

TABLE 2-continued

| No. | R | A | X | R¹ | R² | B | (°C.) |
|---|---|---|---|---|---|---|---|
| 945 | t-Bu | Cl | O | H | H | 5-F-pyridin-2-yl | |
| 946 | t-Bu | Me | O | H | H | 5-F-pyridin-2-yl | |
| 947 | t-Bu | Cl | O | Me | H | 5-F-pyridin-2-yl | |
| 948 | t-Bu | Me | S | H | H | 5-Cl-pyridin-2-yl | |
| 949 | t-Bu | Cl | S | H | H | 6-Cl-pyridin-3-yl | |
| 950 | t-Bu | Cl | O | Me | H | 5-Cl-pyridin-2-yl | |
| 951 | t-Bu | Cl | S | H | H | 6-Br-pyridin-3-yl | 115.5~117.5 |
| 952 | i-Pro | Cl | O | H | H | 6-I-pyridin-3-yl | |
| 953 | Et | Et | S | H | H | 5-I-pyridin-2-yl | |
| 954 | t-Bu | Me | S | H | H | 2-Cl-pyridin-4-yl | |

TABLE 2-continued
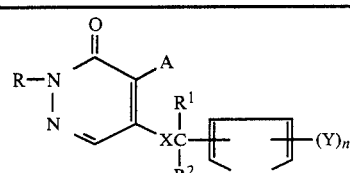
| No. | R | A | X | R¹ | R² | B —(Y)ₙ | (°C.) |
|---|---|---|---|---|---|---|---|
| 955 | Pro | Cl | S | H | H | 4-Me, 2-Cl, 6-Me pyridine | |
| 956 | Et | Cl | O | H | H | 2,6-diMe pyridine | |
| 957 | t-Bu | Cl | S | H | H | 5-Me, 2-Me pyridine | |
| 958 | t-Bu | Me | O | H | H | 5-Me, 2-Et pyridine | |
| 959 | t-Bu | Cl | S | H | H | 5-Me, 2-Pro pyridine | |
| 960 | t-Bu | Me | S | H | H | 5-i-Pro, 2-Me pyridine | |
| 961 | t-Bu | Me | S | H | H | 5-Me, 2-Bu pyridine | |
| 962 | t-Bu | Cl | O | Me | H | 5-Me, 2-Bu pyridine | |
| 963 | t-Bu | Cl | S | H | H | 5-Bu, 2-Me pyridine | oil |
| 964 | t-Bu | Cl | O | H | H | 5-Bu, 2-Me pyridine | 108.0~109.0 |
| 965 | t-Bu | Cl | S | H | H | 5-Me, 2-i-Bu pyridine | |

TABLE 2-continued
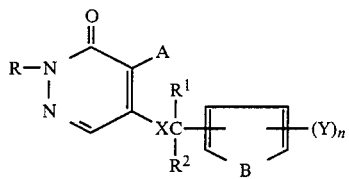
| No. | R | A | X | R¹ | R² | B | (°C.) |
|---|---|---|---|---|---|---|---|
| 966 | t-Bu | Me | O | H | H | 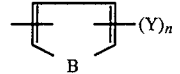 | |
| 967 | t-Bu | Me | S | H | H | 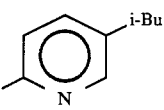 | |
| 968 | t-Bu | Cl | O | H | H | 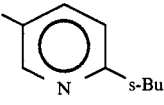 | |
| 969 | t-Bu | Cl | S | H | H | 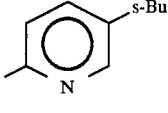 | |
| 970 | t-Bu | Me | S | H | H | 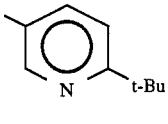 | |
| 971 | t-Bu | Cl | S | Me | H | 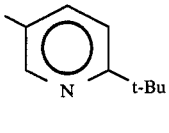 | |
| 972 | t-Bu | Me | O | H | H | 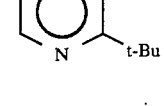 | |
| 973 | t-Bu | Cl | S | H | H | 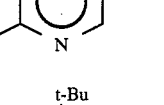 | |
| 974 | t-Bu | Cl | S | H | H | 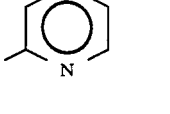 | |
| 975 | t-Bu | Me | O | H | H | 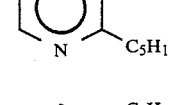 | |

TABLE 2-continued

| No. | R | A | X | R¹ | R² | B-(Y)n | (°C.) |
|---|---|---|---|---|---|---|---|
| 976 | t-Bu | Cl | S | H | H | 5-cyclopropyl-pyridin-2-yl | |
| 977 | t-Bu | Cl | S | H | H | 5-methyl-2-(cyclohexyl)pyridin-... | |
| 978 | t-Bu | Me | S | H | H | 6-methyl-3-cyclohexyl-pyridinyl | |
| 979 | t-Bu | Cl | S | H | H | 6-methyl-3-(CF₃)-pyridin-2-yl | |
| 980 | t-Bu | Cl | O | H | H | 5-methyl-2-(CF₃)-pyridinyl | |
| 981 | t-Bu | Cl | S | H | H | 5-methyl-2-(4-chlorophenyl)pyridinyl | |
| 982 | t-Bu | Cl | O | H | H | 5-methyl-2-(4-fluorophenyl)pyridinyl | |
| 983 | t-Bu | Me | O | H | H | 5-methyl-2-(4-fluorophenyl)pyridinyl | |

TABLE 2-continued
| No. | R | A | X | R¹ | R² | B | (°C.) |
|---|---|---|---|---|---|---|---|
| 984 | t-Bu | Cl | O | Me | H | 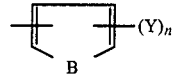 | |
| 985 | t-Bu | Me | S | H | H | 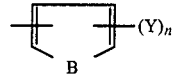 | |
| 986 | t-Bu | Br | O | H | H | 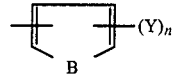 | |
| 987 | t-Bu | Cl | S | H | H | 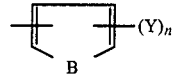 | |
| 988 | Et | Br | S | H | H | 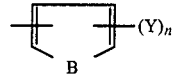 | |
| 989 | i-Pro | Br | O | H | H | 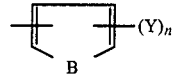 | |
| 990 | Et | Cl | O | H | H | 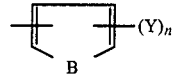 | |
| 991 | t-Bu | Cl | S | H | H | 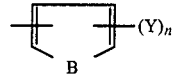 | |

TABLE 2-continued
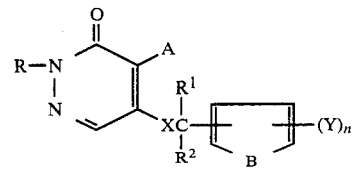
| No. | R | A | X | R¹ | R² | B-(Y)n | (°C.) |
|---|---|---|---|---|---|---|---|
| 992 | t-Bu | Me | S | H | H | 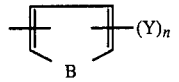 | |
| 993 | Et | Cl | O | H | H | 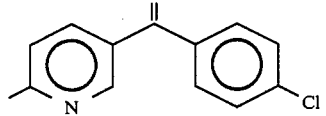 | |
| 994 | Pro | Cl | O | H | H | 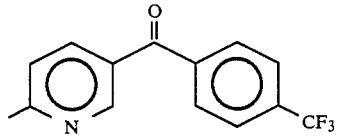 | |
| 995 | i-Pro | Cl | O | H | H | 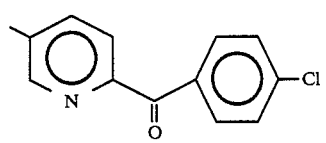 | |
| 996 | Bu | Cl | S | H | H | 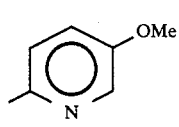 | |
| 997 | t-Bu | Cl | S | H | H | 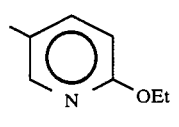 | 92.0~93.5 |
| 998 | t-Bu | Me | S | H | H | 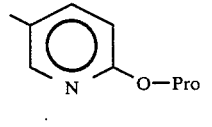 | oil |
| 999 | t-Bu | Cl | O | H | H | 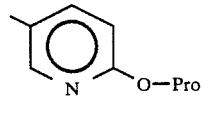 | oil |
| 1000 | t-Bu | Cl | O | Me | H | 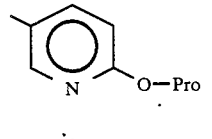 | |
| 1001 | t-Bu | Cl | O | H | H | 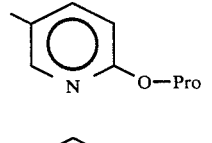 | 104.4~106.3 |

TABLE 2-continued

[Structure shown with R-N, N=N ring bearing A, R¹, R², XC, and B-(Y)n group]

| No. | R | A | X | R¹ | R² | B–(Y)n | (°C.) |
|-----|------|----|----|----|----|--------|--------|
| 1002 | t-Bu | Cl | S | H | H | 4-Me-pyridin-2-yl–O–Pro | |
| 1003 | t-Bu | Cl | S | H | H | 5-Me-pyridin-2-yl–O–Bu | 57.0~58.0 |
| 1004 | t-Bu | Me | O | H | H | 5-Me-pyridin-2-yl–O–Bu | oil |
| 1005 | t-Bu | Me | S | H | H | 5-Me-pyridin-2-yl–O–i-Bu | |
| 1006 | t-Bu | Cl | O | H | H | 5-Me-pyridin-2-yl–O–s-Bu | |
| 1007 | t-Bu | Cl | S | H | H | 5-Me-pyridin-2-yl–O–C₅H₁₁ | 78.0~82.0 |
| 1008 | i-Pro | Cl | O | H | H | 5-Me-pyridin-2-yl–O–C₆H₁₃ | |
| 1009 | t-Bu | Cl | S | H | H | 5-Me-pyridin-2-yl–OCH₂–(2-Me-phenyl) | oil |
| 1010 | t-Bu | Me | O | H | H | 5-Me-pyridin-2-yl–OCH₂–(4-F-phenyl) | oil |
| 1011 | t-Bu | Cl | O | H | H | 5-Me-pyridin-2-yl–OCH₂–(4-F-phenyl) | 121.0~124.0 |

TABLE 2-continued

| No. | R | A | X | R¹ | R² | B-(Y)n | m.p. (°C.) |
|-----|---|---|---|----|----|--------|------------|
| 1012 | t-Bu | Me | O | H | H | 6-Me-pyridin-3-yl-OCH₂-(4-F-C₆H₄) | |
| 1013 | t-Bu | Cl | S | H | H | 5-Me-pyridin-2-yl-O-(4-CF₃-C₆H₄) | |
| 1014 | t-Bu | Me | S | H | H | 5-Me-pyridin-2-yl-O-(2-Cl-4-CF₃-C₆H₃) | |
| 1015 | t-Bu | Cl | S | H | H | 6-Me-pyridin-3-yl-O-(2,4-Cl₂-C₆H₃) | |
| 1016 | t-Bu | Cl | S | H | H | 4-Me-pyridin-2-yl-O-(2-Cl-4-CF₃-C₆H₃) | |
| 1017 | t-Bu | Me | S | H | H | 5-Me-pyridin-2-yl-OCH₂CF₃ | m.p. |
| 1018 | t-Bu | Cl | O | H | H | 6-Me-pyridin-3-yl-OCH₂CH₂CH₂CF₃ | |
| 1019 | t-Bu | Cl | S | H | H | 5-Me-pyridin-2-yl-OCH₂C(Me)=CH₂ | |
| 1020 | t-Bu | Me | O | H | H | 6-Me-pyridin-3-yl-OCH₂C(Me)=CH₂ | |

TABLE 2-continued
| No. | R | A | X | R¹ | R² | B—(Y)ₙ | (°C.) |
|---|---|---|---|---|---|---|---|
| 1021 | Et | Me | S | H | H | 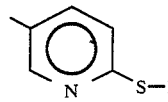 | |
| 1022 | t-Bu | Cl | S | H | H | 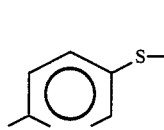 | |
| 1023 | t-Bu | Cl | O | H | H | 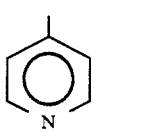 | 540.~56.0 |
| 1024 | t-Bu | Cl | S | H | H | 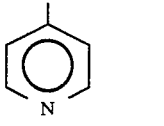 | 82.0~84.0 |
| 1025 | t-Bu | Cl | S | H | H | 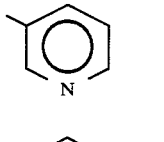 | 124.5~126.5 |
| 1026 | t-Bu | Cl | S | H | H | 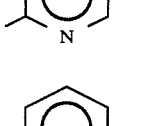 | 106.0~106.5 |
| 1027 | t-Bu | Cl | S | H | H | 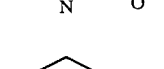 | oil |
| 1028 | t-Bu | Me | S | H | H | 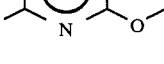 | Oil |
| 1029 | t-Bu | Cl | S | H | H | 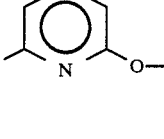 | oil |
| 1030 | t-Bu | Cl | O | Me | H | 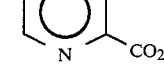 | |

TABLE 2-continued
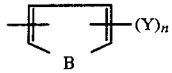
| No. | R | A | X | R¹ | R² | B | (°C.) |
|---|---|---|---|---|---|---|---|
| 1031 | t-Bu | Cl | S | H | H | 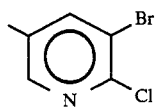 | |
| 1032 | t-Bu | Me | O | H | H | 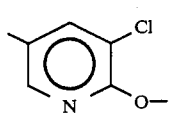 | |
| 1033 | t-Bu | Cl | S | H | H | 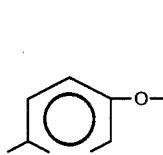 | |
| 1034 | t-Bu | Me | S | H | H | 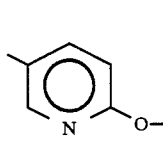 | |
| 1035 | t-Bu | Cl | S | H | H | 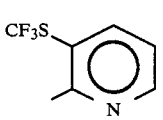 | |
| 1036 | t-Bu | Cl | S | Et | H | 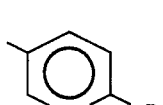 | |
| 1037 | t-Bu | Me | O | Pro | H | 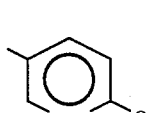 | |
| 1038 | t-C₅H₁₁ | Cl | O | H | H | 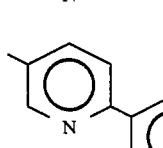 | |
| 1039 | C₆H₁₃ | Cl | S | H | H | 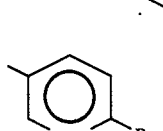 | |
| 1040 | t-Bu | Cl | O | H | H | 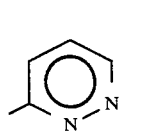 | |

TABLE 2-continued

Structure:
R-N(N=)-C(=O)-C(A)=C(-C(R¹)(R²)-X... with (Y)n-B ring)

| No. | R | A | X | R¹ | R² | B ring with (Y)n | (°C.) |
|---|---|---|---|---|---|---|---|
| 1041 | t-Bu | Cl | O | H | H | 5-methylpyridin-2-yl-O-C₆H₄-Cl | 150.0~154.5 |
| 1042 | t-Bu | Cl | S | H | H | 5-methylpyridin-2-yl-O-C₆H₄-Cl | 113.0~114.0 |
| 1043 | t-Bu | Me | S | H | H | 5-methylpyridin-2-yl-O-cyclohexyl | |
| 1044 | t-Bu | Cl | O | H | H | 5-methylpyridin-2-yl-O-cyclohexyl | |
| 1045 | t-Bu | Cl | S | H | H | 5-methylthiophen-2-yl-O-cyclohexyl | |
| 1046 | t-Bu | Me | O | Me | H | 5-methylthiophen-2-yl-O-cyclohexyl | |
| 1047 | t-Bu | Cl | O | H | H | 6-methyl-4-(N-methyl,N-methylamino)pyridin-2-yl | |
| 1048 | t-Bu | Me | O | H | H | 6-methyl-4-(N-methyl,N-methylamino)pyridin-2-yl | |

TABLE 2-continued
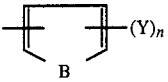
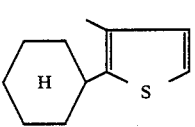
| No. | R | A | X | R¹ | R² | B | (°C.) |
|---|---|---|---|---|---|---|---|
| 1049 | t-Bu | Cl | S | H | H | 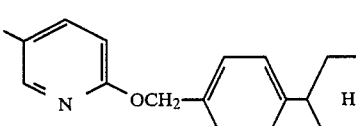 | 124.0~127.5 |
| 1050 | t-Bu | Cl | O | H | H | 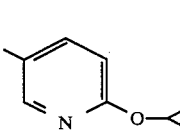 | |
| 1051 | t-Bu | Cl | O | H | H | 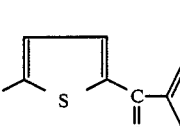 | |
| 1052 | Et | Cl | O | H | H | 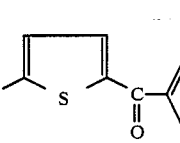 | |
| 1053 | t-Bu | Cl | O | H | H | 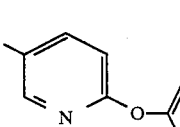 | |
| 1054 | t-Bu | Cl | S | H | H | 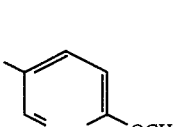 | |
| 1055 | t-Bu | Cl | S | H | H | 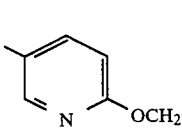 | 109.0~110.0 |
| 1056 | t-Bu | Cl | O | H | H | 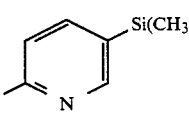 | 102.0~103.0 |
| 1057 | t-Bu | Cl | O | H | H | 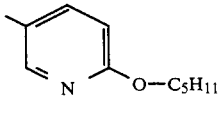 | |
| 1058 | t-Bu | Cl | O | H | H |  | 91.3~93.3 |

TABLE 2-continued

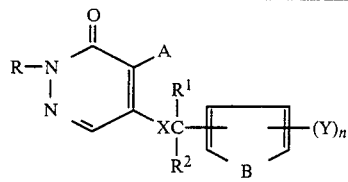

| No. | R | A | X | R¹ | R² | B-(Y)n | (°C.) |
|---|---|---|---|---|---|---|---|
| 1059 | Et | Cl | O | H | H | 5-methyl-2-(O—Pro)pyridine | 139.8~140.9 |
| 1060 | Et | Cl | S | H | H | 5-methyl-2-(O—Pro)pyridine | 116.7~121.1 |
| 1061 | t-Bu | Me | S | H | H | 5-methyl-2-(OCH$_2$CF$_2$CF$_2$H)pyridine | |
| 1062 | t-Bu | Cl | O | H | H | 5-methyl-2-(OCH$_2$CF$_2$CF$_2$H)pyridine | 112.0~118.0 |
| 1063 | t-Bu | Cl | S | H | H | 5-methyl-2-(OCH$_2$CF$_2$CF$_2$H)pyridine | 113.0~114.0 |
| 1064 | t-Bu | Cl | S | H | H | 5-methyl-2-(OCH(CF$_3$)$_2$)pyridine | |
| 1065 | t-Bu | Me | S | H | H | 5-methyl-2-(OCH(CF$_3$)$_2$)pyridine | |
| 1066 | t-Bu | Cl | O | H | H | 5-methyl-2-(OCH(CF$_3$)$_2$)pyridine | |
| 1067 | t-Bu | Cl | O | H | H | 5-methyl-2-(O—Bu)pyridine | 94.1~96.3 |
| 1068 | Et | Me | S | H | H | 5-methyl-2-(OCH$_2$CH$_2$OCH$_3$)pyridine | |

TABLE 2-continued

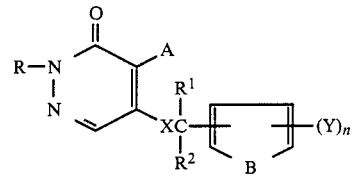

| No. | R | A | X | R¹ | R² | B-(Y)n | (°C.) |
|---|---|---|---|---|---|---|---|
| 1069 | i-Pro | Me | S | H | H | 5-methyl-2-(OCH₂CH₂OCH₃)pyridine | |
| 1070 | i-Pro | Cl | S | H | H | 5-methyl-2-(OCH₂CH₂OCH₃)pyridine | |
| 1071 | i-Pro | Cl | O | H | H | 5-methyl-2-(OCH₂CH₂OCH₃)pyridine | |
| 1072 | t-Bu | Cl | S | H | H | 5-methyl-2-(OCH₂CH₂OCH₃)pyridine | 90.1~91.4 |
| 1073 | t-Bu | Cl | O | H | H | 5-methyl-2-(OCH₂CH₂OCH₃)pyridine | 87.2~89.6 |
| 1074 | t-Bu | Cl | S | H | H | 5-methyl-2-(OCH(CH₃)CH₂OEt)pyridine | |
| 1075 | t-Bu | Cl | O | H | H | 5-methyl-2-(OCH(CH₃)CH₂OEt)pyridine | |
| 1076 | t-Bu | Cl | S | H | H | 5-methyl-2-(OCH₂CH₂OEt)pyridine | |
| 1077 | t-Bu | Cl | S | H | H | 5-methyl-2-(OCH(CH₃)CH₂OCH₃)pyridine | |
| 1078 | t-Bu | Cl | S | H | H | 5-methyl-2-(OCH(CH₃)CH₂OPro)pyridine | |
| 1079 | t-Bu | Cl | O | H | H | 5-methyl-2-(OCH(CH₃)CH₂OPro)pyridine | |

TABLE 2-continued

Structure:

R—N—N=... pyridazinone with substituents A, R¹, R², X, and B(Y)n

| No. | R | A | X | R¹ | R² | B(Y)n | (°C.) |
|---|---|---|---|---|---|---|---|
| 1080 | t-Bu | Cl | S | H | H | 5-methyl-2-(OCH(CH₃)CH₂Oi-Pro)pyridine | |
| 1081 | t-Bu | Cl | S | H | H | 5-methyl-2-(O—i-Pro)pyridine | 111.2~113.3 |
| 1082 | Et | Cl | O | H | H | 5-methyl-2-(O—i-Pro)pyridine | 136.1~137.3 |
| 1083 | t-Bu | Cl | S | H | H | 5-methyl-2-OEt-pyridine | 100.0~101.5 |
| 1084 | t-Bu | Cl | S | H | H | 5-methyl-3-OPro-thiophene | |
| 1085 | t-Bu | Cl | O | H | H | 5-methyl-3-OPro-thiophene | |
| 1086 | t-Bu | Me | O | H | H | 5-methyl-3-OPro-thiophene | |
| 1087 | t-Bu | Me | S | H | H | 5-methyl-3-OPro-thiophene | |
| 1088 | t-Bu | Cl | O | H | H | 4-methyl-2-OPro-thiophene | 100.9~102.3 |
| 1089 | t-Bu | Br | O | H | H | 2-OPro-thiophene | |
| 1090 | t-Bu | Me | O | H | H | 4-methyl-2-OPro-thiophene | |

TABLE 2-continued

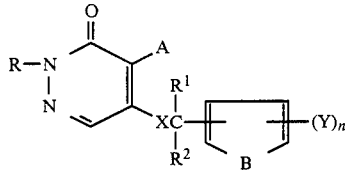

| No. | R | A | X | R¹ | R² | B—(Y)ₙ | (°C.) |
|-----|---|---|---|----|----|--------|-------|
| 1091 | t-Bu | Me | S | H | H | (thiophene)-OPro | |
| 1092 | t-Bu | Cl | S | H | H | (thiophene)-OPro | |
| 1093 | t-Bu | Cl | S | H | H | (pyridine)-OCH₂-(phenyl)-F | 93.0~97.0 |
| 1094 | t-Bu | Cl | O | H | H | (thiophene)-Br | oil |
| 1095 | t-Bu | Cl | S | H | H | (thiophene)-Br | 82.2~85.7 |
| 1096 | t-Bu | Cl | O | H | H | Br-(thiophene) | 111.2~113.3 |
| 1097 | t-Bu | Cl | S | H | H | Br-(thiophene) | oil |

The compounds of the present invention may be produced according to the following reaction formulae:

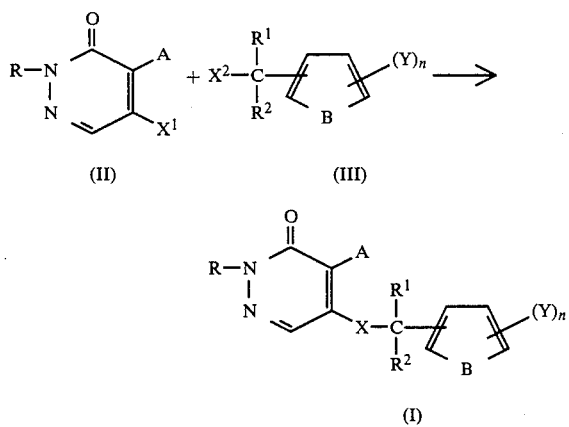

wherein R, R¹, R², A, B, X, Y and n have the same meanings as given above, $X^1$ represents a halogen atom, —OH or —SH, and $X^2$ represents a halogen atom, —OH or —SH, with the proviso that when $X^1$ represents a halogen atom, $X^2$ represents —OH or —SH and when $X^1$ represents —OH or —SH, $X^2$ represents a halogen atom.

Namely, the invention compound (I) may be produced by reacting one of the raw materials, i.e. a (2H)-pyridazinone derivative of the formula (II) with another raw material, i.e. a compound of the formula (III) in an inert solvent in the presence of a hydrogen halide absorbing agent. Solvents to be used in the present invention are, for example, lower alcohols such as methanol and ethanol; ketones such as acetone and methyl ethyl ketone; hydrocarbons such as benzene and toluene; ethers such as isopropyl ether, tetrahydrofurane and 1,4-dioxane; amides such as N,N-dimethylformamide and hexamethylphosphoric triamide; and halogenated hydrocarbons such as dichloromethane and dichloroethane. If desired, mixed solvents consisting of these solvents with water may be used.

As the hydrogen halide absorbing agent, inorganic bases such as sodium hydride, sodium hydroxide, potassium hydroxide, sodium carbonate, potassium carbonate and sodium hydrogen carbonate, and organic bases such as sodium methoxide, sodium ethoxide, triethylamine and pyridine may be used. If necessary, a tetraammonium salt, for example, tetra-n-butylammonium bromide, triethylbenzylammonium chloride and the like may be added as a catalyst into the reaction system. The reaction temperature may be within a range from room temperature to the boiling point of the solvent used in the reaction. There is no limitation in the proportions between the raw materials, but equimolar ratio or approximately equimolar ratio may be advantageous.

In the following, the process for producing the compounds of the present invention will be concretely explained by working examples and reference examples, but the present invention is not limited to these examples.

REFERENCE EXAMPLE 1

Synthesis of 2-t-butyl-5-chloro-4-methyl-3(2H)-pyridazinone starting material

To a solution of 6.0 g (0.25 mol) of magnesium in 50 ml of dry tetrahydrofuran was added dropwise under stream of nitrogen 35.5 g (0.25 mol) of methyl iodide to prepare a Grignard reagent. After dropwise addition of the methyl iodide, 1000 ml of dry toluene was added thereto. The resulting solution was heated at 60° to 70° C. and additional methyl iodide was added thereto until the magnesium completely disappeared. The Grignard reagent was cooled to room temperature and then added dropwise over 20 minutes with a solution of 22.1 g (0.1 mol) of 2-t-butyl-4,5-dichloro-3(2H)-pyridazinone in 200 ml of dry toluene. After dropwise addition, the resulting mixture was subjected to reaction at room temperature for 1.5 hours. The reaction liquid was poured into a solution of 100 ml of concentrated hydrochloric acid in 900 ml of ice water to effect extraction. The resulting organic layer was washed with 500 ml of a 10% sodium hydroxide solution and then with 500 ml of water, and then dried over anhydrous sodium sulfate. Solvent was distilled off therefrom under reduced pressure to give 17.2 g of a crude product. The crude product was subjected to distillation (boiling point: 60° to 62° C./0.22 mmHg) and then to column chromatography [on silica gel; eluting with hexane-acetone (15:1)] for separation and purification to obtain 4.5 g of 2-t-butyl-5-chloro-4-methyl-3(2H)-pyridazinone.

$N_D^{10} = 1.5238$.

NMR (CDCl$_3$, δ, TMS): 1.63 (9H, s), 2.23 (3H, s), 7.66 (1H, s).

REFERENCE EXAMPLE 2

Synthesis of 2-t-butyl-5-mercapto-4-methyl-3(2H)-pyridazinone starting material

To 75 ml of ethanol were added 17.0 g (0.085 mol) of 2-t-butyl-5-chloro-4-methyl-3(2H)-pyridazinone and 8.5 g (0.106 mol) of 70% sodium hydrosulfide and the mixture was stirred under reflux for 4 hours. After cooling, the mixture was poured into 300 ml of ice water and extracted with 200 ml of ethyl ether. The ether layer was washed with 100 ml of water, dried over anhydrous sodium sulfate and then freed of solvent by distillation to obtain 16.3 g of a crude product.

NMR (CDCl$_3$, δ, TMS): 1.61 (9H, s), 2.23 (3H, s), 7.46 (1H, s).

M/Z: 198 (M+), 143 (100%).

The compound was used without subjecting to purification as a starting material in the Preparation Examples given below.

REFERENCE EXAMPLE 3

Synthesis of 2-t-butyl-5-hydroxy-4-methyl-3(2H)-pyridazinone starting material

To 30 ml of ethylene glycol were added 20 g (0.01 mol) of 2-t-butyl-5-chloro-4-methyl-3(2H)-pyridazinone and 2.8 g (0.05 mol) of potassium hydroxide and the mixture was stirred at 130° C. for 4 hours. After allowing to cool, the mixture was poured into 200 ml of water and added with 20 ml of 6N hydrochloric acid. The precipitated crystals were gathered by filtration. After drying, the crystals were washed with 30 ml of hot isopropyl ether to obtain 1.7 g of 2-t-butyl-5-hydroxy-4-methyl-3(2H)-pyridazinone, m.p. 236.0°~239.0° C.

NMR (CDCl$_3$, δ, TMS): 1.62 (9H, s), 1.97 (3H, s), 4.63 (1H, s), 7.60 (1H, s).

M/Z: 182 (M+), 127 (100%).

PREPARATION EXAMPLE 1

Preparation of 2-t-butyl-4-chloro-5-[4-(2-isopropylthioethoxy)-benzyloxy]-3(2H)-pyridazinone (Compound No. 310)

In 15 ml of N,N-dimethylformamide were dissolved 1.2 g of 2-t-butyl-4,5-dichloro-3(2H)-pyridazinone and 1.2 g of p-(2-isopropylthioethoxy)benzyl alcohol, and then 0.31 g of powdery potassium hydroxide was added thereto. The resulting mixture was stirred overnight at room temperature, poured into water, extracted with diethyl ether, washed with water, dried over anhydrous sodium sulfate and then freed of the diethyl ether by distillation under reduced pressure. The resulting solid was recrystallized from n-hexane to obtain 1.2 g of the aimed compound, m.p. 82.0°~84.5° C.

$^1$H-NMR (CDCl$_3$, δ, TMS): 1.28 (3H, d, J=6.5 Hz), 1.62 (9H, s), 2.90 (2H, t, J=7.0 Hz), 2.90 (1H, dq, J=6.5 Hz), 4.12 (2H, t, J=7.0 Hz), 5.21 (2H, s), 6.85 (2H, d, J=8.4 Hz), 7.29 (2H, d, J=8.4 Hz), 7.69 (1H, s).

PREPARATION EXAMPLE 2

Preparation of 2-t-butyl-4-chloro-5-[4-(2-ethoxyethoxy)benzyloxy]-3(2H)-pyridazinone (Compound No. 71)

In 10 ml of N,N-dimethylformamide were dissolved 1.0 g of 2-t-butyl-4-chloro-5-hydroxy-3(2H)-pyridazinone and 1.3 g of 4-(2-ethoxyethoxy)-benzyl bromide, and then 1.0 g of anhydrous potassium carbonate was added thereto. The mixture was heated with stirring on an oil bath at 90° to 100° C. for 3 hours, poured into water, extracted with benzene, washed with water and dried over anhydrous sodium sulfate. Benzene was distilled off under reduced pressure and the resulting oil was purified by means of column chromatography (on silica gel, eluting with benzene/ethyl acetate=18/1) and recrystallization (from n-hexane-benzene) to obtain 1.1 g of the aimed compound, m.p. 82.0°~83.0° C.

$^1$H-NMR (CDCl$_3$, δ, TMS): 1.23 (3H, t, J=7 Hz), 1.61 (9H, s), 3.57 (2H, q, J=7 Hz), 3.50~3.88 (2H, m), 3.98~4.36 (2H, m), 5.19 (2H, s), 6.88 (2H, d, J=9 Hz), 7.29 (2H, d, J=9 Hz), 7.68 (1H, s).

PREPARATION EXAMPLE 3

Preparation of 2-t-butyl-4-chloro-5-[4-(2-methoxyethoxy)-benzylthio]-3(2H)-pyridazinone (Compound No. 45)

In 30 ml of 95% ethanol were dissolved 1.5 g of 2-t-butyl-4-chloro-5-mercapto-3(2H)-pyridazinone and 1.85 g of 4-(2-methoxyethoxy)benzyl bromide, and then 0.48 g of anhydrous sodium carbonate was added thereto. The resulting mixture was stirred overnight at room temperature, poured into water, extracted with benzene, washed with water and dried over anhydrous sodium sulfate. Benzene was distilled off under reduced pressure and the resulting solid was recrystallized from n-hexane-benzene to obtain 1.64 g of the aimed compound, m.p. 105.6°~107.3° C.

$^1$H-NMR (CDCl$_3$, δ, TMS): 1.60 (9H, s), 3.39 (3H, s), 3.58~3.82 (2H, m), 3.96~4.20 (2H, m), 4.16 (2H, s), 6.84 (2H, d, J=9 Hz), 7.26 (2H, d, J=9 Hz), 7.56 (1H, s).

PREPARATION EXAMPLE 4

Preparation of 4-bromo-2-ethyl-5-(4-methoxymethoxybenzyloxy)-3(2H)-pyridazinone (Compound No. 2)

In 30 ml of N,N-dimethylformamide were dissolved 1.2 g of 4,5-dibromo-2-ethyl-3(2H)-pyridazinone and 0.88 g of 4-methoxymethoxybenzyl alcohol, and 0.34 g of powdery potassium hydroxide was added thereto. The reaction mixture was stirred overnight at room temperature, poured into water and extracted with benzene. The benzene layer was washed with water, dried over anhydrous sodium sulfate and freed of the benzene by distillation under reduced pressure. The resulting oil was purified by means of TLC [eluting with benzene/ethyl acetate (12/1)] and recrystallization (from benzene/n-hexane) to obtain 450 mg of the aimed compound, m.p. 104°~106.0° C.

$^1$H-NMR (CDCl$_3$, δ, TMS): 1.33 (3H, t, J=7 Hz), 3.44 (3H, s), 4.20 (2H, q, J=7 Hz), 5.13 (2H, s), 5.21 (2H, s), 6.99 (2H, d, J=8 Hz), 7.30 (2H, d, J=8 Hz), 7.63 (1H, s).

PREPARATION EXAMPLE 5

Preparation of 4-bromo-2-t-butyl-5-[4-(3-propoxypropoxy)-benzyloxy]-3(2H)-pyridazinone (Compound No. 422)

In 20 ml of N,N-dimethylformamide were dissolved 1.7 g of 4-bromo-2-t-butyl-5-hydroxy-3(2H)-pyridazinone and 2.0 g of 4-(3-propoxypropoxy)-benzyl bromide, and 1.3 g of anhydrous potassium carbonate was added thereto. The resulting mixture was heated under stirring on an oil bath at 80° to 90° C. for 3 hours. Then, procedures similar to those in Preparation Example 2 were carried out to obtain 1.3 g of the aimed compound as an oil.

$^1$H-NMR (CDCl$_3$, δ, TMS): 0.91 (3H, t, J=6.4 Hz), 1.61 (9H, s), 1.29~2.27 (4H, m), 3.37 (2H, t, J=6.4 Hz), 3.56 (2H, t, J=6.4 Hz), 4.05 (2H, t, J=6.4 Hz), 5.20 (2H, s), 6.95 (2H, d, J=8 Hz), 7.30 (2H, d, J=8 Hz), 7.59 (1H, s).

PREPARATION EXAMPLE 6

Preparation of 2-t-butyl-4-chloro-5-(4-methoxymethoxybenzylthio)-3(2H)-pyridazinone (Compound No. 7)

In 10 ml of N,N-dimethylformamide were dissolved 0.94 g of 2-t-butyl-4-chloro-5-mercapto-3(2H)-pyridazinone and 0.8 g of 4-methoxymethoxybenzyl chloride, and then 0.55 g of anhydrous sodium carbonate was added thereto. The mixture was stirred overnight at room temperature. Then, procedures similar to those in Preparation Example 3 were carried out to obtain 520 mg of the aimed compound, m.p. 50.0°~54.0° C.

$^1$H-NMR (CDCl$_3$, δ, TMS): 1.60 (9H, s), 3.42 (3H, s), 4.17 (2H, s), 5.10 (2H, s), 6.94 (2H, d, J=8.4 Hz), 7.26 (2H, d, J=8.4 Hz), 7.56 (1H, s).

PREPARATION EXAMPLE 7

Preparation of 2-t-butyl-4-chloro-5-[4-(2-propoxyethoxy)-benzyloxy]-3(2H)-pyridazinone (Compound No. 87)

In 30 ml of N,N-dimethylformamide were dissolved 2.0 g of 2-t-butyl-4-chloro-5-hydroxy-3(2H)-pyridazinone and 3.0 g of 4-(2-propoxyethoxy)-benzyl bromide, and then 2.0 g of anhydrous potassium carbonate was added thereto. The mixture was heated under stirring on an oil bath at 80° to 90° C. for 3 hours. Then, procedures similar to those in Preparation Example 2 were carried out to obtain 1.4 g of the aimed product as an oil.

$^1$H-NMR (CDCl$_3$, δ, TMS): 0.93 (3H, t, J=6.8 Hz), 1.61 (9H, s), 1.38~1.89 (2H, m), 3.48 (2H, t, J=6.4 Hz), 3.65~3.91 (2H, m), 3.99~4.27 (2H, m), 5.21 (2H, s), 6.91 (2H, d, J=9 Hz), 7.32 (2H, d, J=9 Hz), 7.70 (1H, s).

PREPARATION EXAMPLE 8

Preparation of 2-t-butyl-4-chloro-5-[4-(2-ethoxy-1-methylethoxy)-benzyloxy]-3(2H)-pyridazinone (Compound No. 511)

In 30 ml of N,N-dimethylformamide were dissolved 2.0 g of 2-t-butyl-4-chloro-5-hydroxy-3(2H)-pyridazinone and 3.0 g of 4-(2-ethoxy-1-methylethoxy)-benzyl bromide, and then 1.9 g of anhydrous potassium carbonate was added thereto. The mixture was heated under stirring on an oil bath at 80° to 90° C. for 3 hours. Then, procedures similar to those in Preparation Example 2 were carried out to obtain 1.5 g of the aimed product, m.p. 72.3°~73.1° C.

$^1$H-NMR (CDCl$_3$, δ, TMS): 1.18 (3H, t, J=7 Hz), 1.31 (3H, d, J=6 Hz), 1.61 (9H, s), 3.30~3.79 (4H, m), 4.38~4.72 (1H, m), 5.20 (2H, s), 6.93 (2H, d, J=8.8 Hz), 7.30 (2H, d, J=8.8 Hz), 7.71 (1H, s).

PREPARATION EXAMPLE 9

Preparation of 2-t-butyl-4-chloro-5-[4-(1-methyl-2-propoxyethoxy)-benzyloxy]-3(2H)-pyridazinone (Compound No. 517)

Procedures similar to those in Preparation Example 8 were carried out by using 2.0 g of 2-t-butyl-4-chloro-5-hydroxy-3(2H)-pyridazinone and 3.1 g of 4-(1-methyl-2-propoxyethoxy)-benzyl bromide to obtain 1.43 g of the aimed compound as an oil.

$^1$H-NMR (CDCl$_3$, δ, TMS): 0.89 (3H, t, J=6.8 Hz), 1.31 (3H, d, J=6 Hz), 1.60 (9H, s), 1.25~1.68 (2H, m), 3.27~3.68 (4H, m), 4.35~4.69 (1H, m), 5.20 (2H, s), 6.91 (2H, d, J=8.4 Hz), 7.29 (2H, d, J=8.4 Hz), 7.71 (1H, s).

PREPARATION EXAMPLE 10

Preparation of 2-t-butyl-4-chloro-5-[4-(2-ethoxy-1-ethylethoxy)-benzyloxy]-3(2H)-pyridazinone (Compound No. 664)

Procedures similar to those in Preparation Example 8 were carried out by using 2.0 g of 2-t-butyl-4-chloro-5-hydroxy-3(2H)-pyridazinone and 3.1 g of 4-(2-ethoxy-1-ethylethoxy)-benzyl bromide to obtain 1.0 g of the aimed compound as an oil.

$^1$H-NMR (CDCl$_3$, δ, TMS): 0.99 (3H, t, J=7 Hz), 1.17 (3H, t, J=7 Hz), 1.60 (9H, s), 1.39~1.88 (2H, m), 3.28~3.73 (4H, m), 4.08~4.51 (1H, m), 5.19 (2H, s), 6.91 (2H, d, J=8.6 Hz), 7.27 (2H, d, J=8.6 Hz), 7.68 (1H, s).

PREPARATION EXAMPLE 11

Preparation of 2-t-butyl-4-chloro-5-[4-(1-methyl-2-isopropoxyethoxy)-benzyloxy]-3(2H)-pyridazinone (Compound No. 524)

In 15 ml of N,N-dimethylformamide were dissolved 1.0 g of 2-t-butyl-4-chloro-5-hydroxy-3(2H)-pyridazinone and 1.6 g of 4-(1-methyl-2-isopropoxyethoxy)-benzyl bromide, and thereto was added 1.0 g of anhydrous potassium carbonate. The mixture was heated under stirring on an oil bath at 100° to 120° C. for 2 hours. Then, procedures similar to those in Preparation Example 2 were conducted to give 1.2 g of the aimed compound, m.p. 60.0°~62.0° C.

$^1$H-NMR (CDCl$_3$, δ, TMS): 1.15 (3H, d, J=6 Hz), 1.27 (3H, t, J=6.4 Hz, 1.63 (9H, s), 3.32~3.86 (4H, m), 4.21~4.70 (2H, m), 5.20 (2H, s), 6.92 (2H, d, J=8.4 Hz), 7.32 (2H, d, J=8.4 Hz), 7.73 (1H, s).

PREPARATION EXAMPLE 12

Preparation of 2-t-butyl-4-chloro-5-[4-(2-hexyloxy-1-methylethoxy)-benzylthio]-3(2H)-pyridazinone (Compound No. 553)

In 20 ml of N,N-dimethylformamide were dissolved 1.7 g of 2-t-butyl-4-chloro-5-mercapto-3(2H)-pyridazinone and 2.8 g of 4-(2-hexyloxy-1-methylethoxy)-benzyl bromide, and the resulting solution was stirred overnight at room temperature. The crude product which had been obtained similarly to the procedures in Preparation Example 3 was isolated through column chromatography [eluting with benzene/ethyl acetate (18/1)] to give 3.4 g of the aimed product as an oil.

$^1$H-NMR (CDCl$_3$, δ, TMS): 1.31 (3H, d, J=6 Hz), 0.20~1.93 (11H, m), 1.64 (9H, s), 3.28~3.70 (4H, m), 4.18 (2H, s), 4.29~4.78 (1H, m), 6.87 (2H, d, J=8.6 Hz), 7.27 (2H, d, J=8.4 Hz), 7.59 (1H, s).

PREPARATION EXAMPLE 13

Preparation of 2-t-butyl-4-chloro-5-[4-(2-ethoxypropoxy)benzyloxy]-3(2H)-pyridazinone (Compound No. 579)

In 15 ml of N,N-dimethylformamide were dissolved 1.5 g of 2-t-butyl-4-chloro-5-hydroxy-3(2H)-pyridazinone and 2.2 g of 4-(2-ethoxypropoxy)-benzyl bromide, and the resulting solution was heated under stirring on an oil bath at 80° to 90° C. for 3 hours. Then, similarly to the procedures in Preparation Example 2, 1.1 g of the aimed product was obtained as an oil.

$^1$H-NMR (CDCl$_3$, δ, TMS): 1.05 1.44 (6H, m), 1.61 (9H, s), 3.62 (2H, t, J=6.4 Hz), 3.83~4.12 (3H, m), 5.20 (2H, s), 6.90 (2H, d, J=9 Hz), 7.30 (2H, d, J=9 Hz), 7.69 (1H, s).

PREPARATION EXAMPLE 14

Preparation of 2-t-butyl-4-chloro-5-[4-(1,1-dimethyl-2-propoxyethoxy)-benzyloxy]-3(2H)-pyridazinone (Compound No. 615)

By using 2.0 g of 2-t-butyl-4-chloro-5-hydroxy-3(2H)-pyridazinone and 3.0 g of 4-(1,1-dimethyl-2-propoxyethoxy)benzyl bromide and similarly to the procedures in Preparation Example 13, 2.1 g of the aimed product was obtained as an oil.

$^1$H-NMR (CDCl$_3$, δ, TMS): 0.94 (3H, t, J=7 Hz), 1.30 (6H, s), 1.62 (9H, s), 1.42~1.96 (2H, m), 3.39 (2H, s), 3.44 (2H, t, J=7 Hz), 5.24 (2H, s), 7.02 (2H, d, J=9 Hz), 7.30 (2H, d, J=9 Hz), 7.63 (1H, s).

PREPARATION EXAMPLE 15

Preparation of 2-t-butyl-4-chloro-5-[4-(2-diethylaminoethoxy)-α-methylbenzyloxy]-3(2H)-pyridazinone (Compound No. 789)

By using 1.0 g of 2-t-butyl-4,5-dichloro-3(2H)-pyridazinone and 1.1 g of 4-(2-diethylaminoethoxy)-α-methylbenzyl alcohol and similarly to the procedures in Preparation Example 1, a crude product was obtained. The crude product was then purified through column chromatography (eluting with chloroform/methanol=200/5) to obtain 710 mg of the aimed product as an oil.

$^1$H-NMR (CDCl$_3$, δ, TMS): 1.05 (6H, t, J=7.4 Hz), 1.57 (9H, s), 1.68 (3H, d, J=6 Hz), 2.62 (4H, q, J=7.4 Hz), 2.84 (2H, t, J=6 Hz), 4.01 (2H, t, J=6 Hz), 5.44 (1H, q, J=6 Hz), 6.85 (2H, d, J=9.2 Hz), 7.26 (2H, d, J=9.2 Hz), 7.51 (1H, s).

PREPARATION EXAMPLE 16

Preparation of 2-t-butyl-5-(4-ethoxymethoxybenzyloxy)-4-methyl-3(2H)-pyridazinone (Compound No. 14)

By using 1.0 g of 2-t-butyl-5-hydroxy-4-methyl-3(2H)-pyridazinone, 1.1 g of 4-ethoxymethoxybenzyl chloride and 1.0 g of anhydrous potassium carbonate and similarly to the procedures in Preparation Example 2, 1.1 g of the aimed product was obtained as an oil.

$^1$H-NMR (CDCl$_3$, δ, TMS): 1.22 (3H, t, J=7 Hz), 1.61 (9H, s), 2.03 (3H, s), 3.73 (2H, q, J=7 Hz), 5.10 (2H, s), 5.21 (2H, s), 7.02 (2H, d, J=9 Hz), 7.29 (2H, d, J=9 Hz), 7.70 (1H, s).

PREPARATION EXAMPLE 17

Preparation of 2-t-butyl-5-{(5-t-butyl-2-thienyl)-methylthio}-4-methyl-3(2H)-pyridazinone (Compound No. 872)

In 20 ml of N,N-dimethylformamide were dissolved 2.0 g of 2-t-butyl-5-mercapto-4-methyl-3(2H)-pyridazinone and 1.9 g of 2-t-butyl-5-chloromethylthiophene, and thereto was added under stirring 1.5 g of potassium carbonate at room temperature. After additional stirring for 8 hours at room temperature, the mixture was poured into 50 ml of water and then extracted twice with 50 ml of benzene. The organic layer was washed with water, dried over anhydrous sodium sulfate and then freed of solvent by distillation under reduced pressure to obtain 3.5 g of a crude product. The crude product was separated and purified through thin layer chromatography (on silica gel; benzene) to give 2.2 g of 2-t-butyl-5-{(5-t-butyl-2-thienyl)-methylthio}-4-methyl-3(2H)-pyridazinone as an oil.

NMR (CDCl$_3$, δ, TMS): 1.32 (9H, s), 1.61 (9H, s), 2.14 (3H, s), 4.28 (2H, s), 6.58 (1H, d, J=3 Hz), 6.74 (1H, d, J=3 Hz), 7.64 (1H, s).

PREPARATION EXAMPLE 18

Preparation of 2-t-butyl-4-chloro-5-{(6-propyloxy-3-pyridyl)-methylthio}-3(2H)-pyridazinone (Compound No. 997)

To a solution of 2.2 g of 2-t-butyl-4-chloro-5-mercapto-3(2H)-pyridazinone and 1.9 g of 5-chloromethyl-2-propyloxypyridine in 20 ml of N,N-dimethylformamide was added under stirring 1.5 g of potassium carbonate at room temperature. After additional stirring for 8 hours at room temperature, the mixture was poured into 50 ml of water and then extracted twice with 50 ml of benzene. The organic layer was washed with water, dried over anhydrous sodium sulfate and then freed of solvent by distillation under reduced pressure to obtain 3.7 g of a crude product. The crude product was added with isopropyl ether and recrystallized therefrom to give 3.0 g of 2-t-butyl-4-chloro-5{-(6-propyloxy-3-pyridyl)-methylthio}-3(2H)-pyridazinone, m.p. 92.0°~93.5° C.

$^1$H-NMR (CDCl$_3$, δ, TMS): 1.01 (3H, t, J=7 Hz), 1.50~2.00 (2H, m), 1.61 (9H, s), 4.21 (2H, s), 4.24 (2H, t, J=7 Hz), 6.84 (1H, d, J=9 Hz), 7.53~7.73 (1H, m), 7.66 (1H, s), 8.18 (1H, d, J=2 Hz).

PREPARATION EXAMPLE 19

Preparation of 2-t-butyl-4-chloro-5-{(5-chloro-2-thienyl)-α-methylmethylthio}-3(2H)-pyridazinone (Compound No. 858)

To a solution of 2.2 g of 2-t-butyl-4-chloro-5-mercapto-3(2H)-pyridazinone and 2.0 g of 2-chloro-5-(1-chloroethyl)thiophene in 20 ml of N,N-dimethylformamide was added under stirring 1.5 g of potassium carbonate at room temperature. After additional stirring for 8 hours at room temperature, the mixture was poured into 50 ml of water and then extracted twice with 50 ml of benzene. The organic layer was washed with water, dried over anhydrous sodium sulfate and then freed of solvent by distillation under reduced pressure to obtain 3.7 g of a crude product. The crude product was separated and purified through column chromatography (on silica gel: benzene) to obtain 2.5 g of 2-t-butyl-4-chloro-5{(5-chloro-2-thienyl)-α-methylmethylthio}-3(2H)-pyridazinone as an oil.

NMR (CDCl$_3$, δ, TMS): 1.61 (9H, s), 1.75 (3H, d, J=7 Hz), 4.87 (1H, q, J=7 Hz) 6.70 (1H, d, J=3 Hz), 6.85 (1H, d, J=3 Hz), 7.61 (1H, s).

PREPARATION EXAMPLE 20

Preparation of 2-t-butyl-4-chloro-5-[{6-(4-chlorophenoxy)-3-pyridyl}-methyloxy]-3(2H)-pyridazinone (Compound No. 1041)

To 20 ml of N,N-dimethylformamide were added 2.1 g of 2-t-butyl-4-chloro-5-hydroxy-3(2H)-pyridazinone, 2.5 g of 5-chloromethyl-2-(4-chlorophenoxy)-pyridine and 1.5 g of potassium carbonate, and the mixture was stirred at 80° to 90° C. for 2 hours. After cooling, the reaction mixture was poured into 50 ml of water and extracted twice with 50 ml of benzene. The organic layer was washed with water, dried over anhydrous sodium sulfate and then freed of solvent by distillation under reduced pressure to obtain 3.9 g of a crude product. The crude product was added with a mixed solvent of isopropyl ether and 2-propanol and recrystallized therefrom to give 3.3 g of 2-t-butyl-4-chloro-5-[{6-(4-chlorophenoxy)-3-pyridyl}methyloxy]-3(2H)-pyridazinone, m.p. 150.0°~154.5° C.

NMR (CDCl$_3$, δ, TMS): 1.61 (9H, s), 5.21 (2H, s), 6.85~7.40 (5H, m), 7.65~7.85 (1H, m), 7.72 (1H, s), 8.15 (1H, d, J=2 Hz).

PREPARATION EXAMPLE 21

Preparation of 4-chloro-5[{5-(4-chlorobenzoyl)-2-thienyl}methyloxy]-2-ethyl-3(2H)-pyridazinone (Compound No. 895)

To 20 ml of N,N-dimethylformamide were added 1.9 g of 4-chloro-2-ethyl-5-hydroxy-3(2H)-pyridazinone, 3.2 g of 2-bromomethyl-5-(4-chlorobenzoyl)-thiophene and 1.5 g of potassium carbonate, and the mixture was stirred at 50° to 60° C. for 2 hours. After cooling, the reaction mixture was poured into 50 ml of water and extracted twice with 50 ml of benzene. The organic layer was washed with water, dried over anhydrous sodium sulfate and then freed of solvent by distillation under reduced pressure to obtain 4.0 g of a crude product. The crude product was recrystallized from 2-propanol to obtain 3.1 g of 4-chloro-5-[{5-(4-chlorobenzoyl)-2-thienyl}-methyloxy]-2-ethyl-3(2H)-pyridazinone, m.p. 168.0°~168.5° C.

NMR (CDCl$_3$, δ, TMS): 1.35 (3H, t, J=7 Hz), 4.21 (2H, q, J=7 Hz), 5.67 (2H, s), 7.25~7.95 (6H, m), 8.12 (1H, s).

PREPARATION EXAMPLE 22

Preparation of 2-t-butyl-5[{6-(4-fluorobenzyloxy)-3-pyridyl}-methyloxy]-4-methyl-3(2H)-pyridazinone (Compound No. 1010)

To a solution of 2.3 g of 6-(4-fluorobenzyloxy)-3-pyridine methanol in 20 ml of N,N-dimethylformamide was added under stirring at 0° C. 0.5 g of 55% sodium hydride (in mineral oil). After stirring for 30 minutes at room temperature, thereto was added dropwise a solution of 2.0 g of 2-t-butyl-5-chloro-4-methyl-3(2H)-pyridazinone in 5 ml of N,N-dimethylformamide. The reaction mixture was stirred at room temperature for additional 8 hours, poured into 50 ml of ice water and extracted twice with 50 ml of benzene. The organic layer was washed with water, dried over anhydrous sodium sulfate and then freed of solvent by distillation under reduced pressure to give 3.8 g of a crude product. The crude product was separated and purified through thin layer chromatography (on silica gel; benzene) to obtain 2.5 g of 2-t-butyl-5-[{6-(4-fluorobenzyloxy)-3-pyridyl}-methyloxy]-4-methyl-3(2H)-pyridazinone as an oil.

NMR (CDCl$_3$, δ, TMS): 1.63 (9H, s), 2.02 (3H, s), 5.09 (2H, s), 5.34 (2H, s), 6.75~7.80 (6H, m), 7.78 (1H, s), 8.21 (1H, d, J=2 Hz).

PREPARATION EXAMPLE 23

Preparation of 2-t-butyl-4-chloro-5[{6-(4-fluorobenzyloxy)-3-pyridyl}-methyloxy]-3(2H)-pyridazinone (Compound No. 1011)

To a solution of 2.3 g of 6-(4-fluorobenzyloxy)-3-pyridine methanol in 20 ml of N,N-dimethylformamide was added under stirring at 0° C. 0.5 g of 55% sodium hydride (in mineral oil). After stirring for 30 minutes at room temperature, thereto was added 2.2 g of 2-t-butyl-4,5-dichloro-3(2H)-pyridazinone. The reaction mixture was stirred at room temperature for additional 8 hours, poured into 50 ml of ice water and extracted twice with 50 ml of benzene. The organic layer was washed with water, dried over anhydrous sodium sulfate and then freed of solvent by distillation under reduced pressure to give 4.1 g of a crude product. The crude product was added with isopropyl ether and recrystallized therefrom to obtain 3.2 g of 2-t-butyl-4-chloro-5-[{6-(4-fluorobenzyloxy)-3-pyridyl}-methyloxy]-3(2H)-pyridazinone, m.p. 121.0°~124.0° C.

NMR (CDCl$_3$, δ, TMS): 1.62 (9H, s), 5.25 (2H, s), 5.33 (2H, s), 6.75~7.85 (6H, m), 7.89 (1H, s), 8.26 (1H, d, J=2 Hz).

PREPARATION EXAMPLE 24

Preparation of 2-t-butyl-4-chloro-5-[{6-(2,2,3,3-tetrafluoropropyloxy)-3-pyridyl}-methylthio]-3(2H)-pyridazinone (Compound No. 1063)

In 40 ml of acetonitrile were dissolved 2.2 g of 2-t-butyl-4-chloro-5-mercapto-3(2H)-pyridazinone and 2.7 g of 5-chloromethyl-2-(2,2,3,3-tetrafluoropropyloxy)-pyridine, and thereto was added 1.5 g of potassium carbonate. The reaction mixture was stirred overnight at room temperature, poured into water and extracted with benzene. The organic layer was washed with a 5% aqueous solution of sodium hydroxide and then with water, and dried over anhydrous sodium sulfate. Solvent was distilled off under reduced pressure and the resulting crystals were washed with n-hexane to obtain 4.0 g of 2-t-butyl-4-chloro-5-[{6-(2,2,3,3-tetrafluoropropyloxy)-3-pyridyl}-methylthio]-3(2H)-pyridazinone, m.p. 113.0°~114.0° C.

NMR (CDCl$_3$, δ, TMS): 1.60 (9H, s), 4.20 (2H, s), 4.49~4.94 (2H, m), 5.94 (1H, t-t, J=52 Hz, 4 Hz), 6.75 (1H, d, J=9 Hz), 7.53 (1H, s), 7.48~7.77 (1H, m), 8.06 (1H, d, J=2 Hz).

PREPARATION EXAMPLE 25

Preparation of 2-t-butyl-4-chloro-5-[{6-(2,2,3,3-tetrafluoropropyloxy)-3-pyridyl}-methyloxy]-3(2H)-pyridazinone (Compound No. 1062)

In 40 ml of N,N-dimethylformamide were dissolved 2.2 g of 2-t-butyl-4,5-dichloro-3(2H)-pyridazinone and 2.5 g of 6-(2,2,3,3-tetrafluoropropyloxy)-3-pyridine methanol, and thereto was added 0.7 g of powdery potassium hydroxide. The reaction mixture was stirred overnight at room temperature and poured into water. Then, procedures similar to those in Preparation Example 24 were conducted to obtain 3.6 g of 2-t-butyl-4-chloro-5-[{6-(2,2,3,3-tetrafluoropropyloxy)-3-pyridyl}-methyloxy]-3(2H)-pyridazinone, m.p. 112.0°~118.0° C.

NMR (CDCl$_3$, δ, TMS): 1.62 (9H, s), 4.52~4.97 (2H, m), 5.25 (2H, s), 5.99 (1H, t-t, J=52 Hz, 4 Hz), 6.86 (1H, d, J=9 Hz), 7.58~7.88 (1H, m), 7.77 (1H, m), 8.19 (1H, d, J=2 Hz).

PREPARATION EXAMPLE 26

Preparation of 2-t-butyl-4-chloro-5-[{6-(2,2,2-trifluoroethoxy)-3-pyridyl}-methylthio]-3(2H)-pyridazinone (Compound No. 1055)

In 40 ml of methanol were dissolved 2.2 g of 2-t-butyl-4,5-dichloro-3(2H)-pyridazinone and 2.4 g of 5-mercaptomethyl(2,2,2-trifluoro-ethoxy)-pyridine, and thereto was added 1.2 g of sodium carbonate. The reaction mixture was stirred overnight at room temperature and then poured into water. Then, procedures similar to those in Preparation Example 24 were conducted to obtain 3.6 g of 2-t-butyl-4-chloro-5-[{6-(2,2,2-trifluoroethoxy)-3-pyridyl}-methylthio]-3(2H)-pyridazinone, m.p. 109.0°~110.0° C.

NMR (CDCl$_3$, δ, TMS): 1.61 (9H, s), 4.22 (2H, s), 4.73 (2H, q, J=9 Hz), 6.87 (1H, d, J=9 Hz), 7.62 (1H, s), 7.60~7.89 (1H, m), 8.15 (1H, d, J=2 Hz).

PREPARATION EXAMPLE 27

Preparation of 2-t-butyl-4-chloro-5-{4-(2-methoxy-1-methyl-ethoxy)-benzylthio}-3(2H)-pyridazinone (Compound No. 504)

In 30 ml of 95% ethanol were dissolved 1.5 g of 2-t-butyl-4-chloro-5-mercapto-3(2H)-pyridazinone and 1.8 g of 4-(2-methoxy-1-methylethoxy)-benzyl bromide, and thereto was added 0.48 g of powdery potassium hydroxide. The reaction mixture was stirred overnight at room temperature. Then, similarly to the procedures in Preparation Example 3, there was obtained 1.2 g of the aimed product, m.p. 51.0°~52.0° C.

$^1$H-NMR (CDCl$_3$, δ, TMS): 1.27 (3H, d, J=6 Hz), 1.61 (9H, s), 3.35 (3H, s), 3.44 (2H, t, J=5.6 Hz), 4.17 (2H, s), 4.25~4.79 (1H, m), 6.84 (2H, d, J=9 Hz), 7.24 (2H, d, J=9 Hz), 7.59 (1H, s).

PREPARATION EXAMPLE 28

Preparation of 2-t-butyl-4-chloro-5-{4-(2-ethoxy-1-methylethoxy)-benzylthio}-3(2H)-pyridazinone (Compound No. 513)

In 15 ml of N,N-dimethylformamide were dissolved 1.4 g of 2-t-butyl-4-chloro-5-mercapto-3(2H)-pyridazinone and 2.0 g of 4-(2-ethoxy-1-methylethoxy)-benzyl bromide, and thereto was added 1.0 g of anhydrous sodium carbonate. The reaction mixture was stirred overnight at room temperature. Then, similarly to the procedures in Preparation Example 12, there was obtained 2.0 g of the aimed compound, m.p. 89.2°~90.2° C.

$^1$H-NMR (CDCl$_3$, δ, TMS): 1.19 (3H, d, J=6.2 Hz), 1.30 (3H, d, J=6 Hz), 1.60 (9H, s), 3.36~3.78 (4H, m), 4.20 (2H, s), 4.30~4.73 (1H, m), 6.88 (2H, d, J=8.8 Hz), 7.28 (2H, d, J=8.8 Hz), 7.60 (1H, s).

PREPARATION EXAMPLE 29

Preparation of 2-t-butyl-4-chloro-5-{(6-i-propyloxy-3-pyridyl)-methylthio}-3(2H)-pyridazinone (Compound No. 1081)

To a solution of 2.2 g of 2-t-butyl-4-chloro-5-mercapto-3(2H)-pyridazinone and 2.0 g of 5-chloromethyl-2-i-propyloxypyridine in 50 ml of toluene were added 8.8 g of a 5% aqueous solution of sodium hydroxide and 0.2 g of tetra-n-butylammonium bromide, and the mixture was stirred at 40° C. for 5 hours. After termination of the reaction, water was added thereto to remove the aqueous layer. The organic layer was washed with water, dried over anhydrous sodium sulfate and then freed of solvent of distillation under reduced pressure to give 3.7 g of a crude product. The crude product was added with i-propyl ether and recrystallized therefrom to obtain 3.0 g of 2-t-butyl-4-chloro-5-{(6-i-propyloxy-3-pyridyl)-methylthio}-3(2H)-pyridazinone, m.p. 111.2°~113.3° C.

NMR (CDCl$_3$, δ, TMS): 1.34 (6H, d, J=6 Hz), 1.61 (9H, s), 4.17 (2H, s), 5.25 (1H, m), 6.63 (1H, d, J=9 Hz), 7.47~7.67 (1H, m), 7.60 (1H, s), 8.09 (1H, d, J=2 Hz).

With respect to the compounds produced according to any one of the methods in Preparation Examples 1 through 29, the melting points thereof are shown in Tables 1 and 2. Among the compounds, those obtained in the form of an oil are identified with $^1$H-NMR data in Table 3. The Compound numbers correspond to those in Tables 1 and 2.

TABLE 3

| Compound No. | $^1$H—NMR Data CDCl$_3$, δ (ppm) |
|---|---|
| 15 | 1.22(t,3H), 1.63(s,9H), 3.70(q,2H), 4.20(s,2H), 5.20(s,2H), 6.9–7.4(m,4H), 7.61(s,1H), |
| 16 | 1.20(t,3H), 1.60(s,9H), 3.68(q,2H), 5.19(bs,4H), 6.9–7.4(m,4H), 7.62(s,1H) |
| 17 | 1.21(t,3H), 1.62(s,9H), 3.70(q,2H), 5.20(s,4H), 6.9–7.4 (m,4H), 7.70(s,1H) |
| 88 | 0.96(t,3H), 1.5–1.8(m,2H), 1.62(s,9H), 3.51(t,2H), 3.85(t,2H), 4.21(t,2H), 5.19(s,2H), 6.9–7.4(m,3H), 7.69(s,1H) |
| 391 | 0.8–1.0 (m,3H), 1.2–1.8(m,4H), 1.60(s,9H), 2.35(t,2H), 4.1–4.5(m,4H), 5.21(s,2H), 6.8–7.4(m,4H), 7.70(s,1H) |
| 392 | 0.8–1.0(m,3H), 1.2–1.7(m,4H), 1.61(s,9H), 2.35(t,2H), 4.1–4.6(m,4H), 4.23(s,2H), 6.8–7.4(m,4H), 7.62(s,1H) |
| 421 | 0.90(t,3H), 1.4–2.3(m,4H), 1.59(s,9H), 3.2–3.7(m,4H), 4.03(t,2H), 5.20(s,2H), 6.8–7.4(m,4H), 7.70(s,1H) |
| 521 | 0.90(t,3H), 1.30(d,3H), 1.5–1.8(m,2H), 1.60(s,9H), 3.25(d,2H), 3.4–3.6(m,2H), 4.13(s,2H), 4.3–4.6(m,1H), 6.7–7.3(m,4H), 7.50(s,1H) |
| 522 | 0.90(t,3H), 1.30(d,3H), 1.5–1.8(m,2H), 1.62(s,9H), 3.3–3.6(m,4H), 4.2–4.7(m,1H), 4.30(s,2H), 6.7–7.4(m,4H), 7.58(s,1H) |
| 523 | 0.90(t,3H), 1.28(d,3H), 1.5–1.8(m,2H), 1.62(s,9H), 3.3–3.6(m,4H), 4.3–4.7(m,1H), 5.25(s,2H), 6.7–7.5(m,4H), 7.65(s,1H), |
| 531 | 1.0–1.8(m,8H), 1.65(s,9H), 3.4–3.6(m,4H), 4.3–4.8(m,1H), 5.20(s,2H), 6.9–7.4(m,4H), 7.72(s,1H) |
| 533 | 0.9–1.1(m,3H), 1.2–1.7(m,5H), 1.61(s,9H), 3.4–3.6(m,4H), 4.20(s,2H), 4.3–4.7(m,1H), 6.8–7.4(m,4H), 7.60(s,1H) |
| 535 | 0.86(d,6H), 1.32(d,3H), 1.61(s,9H), 1.7–2.0(m,2H), 3.23(d,2H), 3.4–3.8(m,3H), 4.4–4.7(m,1H), 5.21(s,2H), 6.9–7.3(m,4H), 7.72(s,1H) |
| 538 | 0.90(d,6H), 1.35(d,3H), 1.62(s,9H), 1.7–2.0(m,2H), 3.24(d,2H), 3.3–3.8(m,3H), 4.20(s,2H), 4.4–4.7(m,1H), 6.8–7.4(m,4H), 7.61(s,1H) |
| 551 | 0.8–1.7(m,14H), 1.62(s,9H), 3.3–3.6(m,4H), 4.3–4.7(m,1H), 5.21,(s,2H), 6.8–7.4(m,4H), 7.62(s,1H) |
| 552 | 0.9–1.8(m,14H), 1.61(s,9H), 3.4–3.7(m,4H), 4.4–4.8(m,1H), 5.20(s,2H), 6.9–7.4(m,4H), 7.68(s,1H), |
| 554 | 1.35(d,3H), 1.62(s,9H), 3.5–3.7(m,2H), 4.05(d,2H), 4.4–4.8(m,1H), 5.1–5.4(m,2H), 5.6–6.0(m,1H), 6.8–7.4(m,4H), 7.71(s,1H) |
| 555 | 1.35(d,3H), 1.63(s,9H), 3.5–3.7(m,2H), 4.05(d,2H), 4.21(s,2H), 4.4–4.8(m,1H), 5.0–5.4(m,2H), 5.6–5.9(m,1H), 6.8–7.4(m,2H), 7.60(s,1H) |
| 581 | 0.8–1.1(m,3H), 1.2–1.7(m,5H), 1.63(s,9H), 3.4–4.0(m,5H), 5.21(s,2H), 6.8–7.4(m,4H), 7.73(s,1H) |
| 582 | 0.8–1.1(m,3H), 1.2–1.7(m,5H), 1.60(s,9H), 3.4–4.0(m,5H), 4.19(s,2H), 6.8–7.4(m,4H), 7.58(s,1H), |
| 611 | 1.22(t,3H), 1.31(s,6H), 1.62(s,9H), 3.38(s,2H), 3.56(q,2H), 5.22(s,2H), 6.9–7.4(m,4H), 7.70(s,1H) |
| 612 | 1.22(t,3H), 1.29(s,6H), 1.61(s,9H), 3.37(s,2H), 3.54(q,2H), 4.22(s,2H), 6.9–7.3(m,4H), 7.58(s,1H) |
| 616 | 0.8–1.0(t,3H), 1.30(s,6H), 1.2–1.5(m,2H), 1.61(s,9H), 3.3–3.5(m,4H), 4.21(s,2H), 6.9–7.3(m,4H), 7.59(s,1H) |
| 639 | 1.1–1.4(m,6H), 1.61(s,9H), 1.40(s,3H), 3.3–3.7(m,1H), 4.2–4.6(m,1H), 4.22(s,2H), 6.8–7.4(m,4H), 7.65(s,1H) |
| 659 | 0.99(s,3H), 1.5–1.9(m,2H), 1.60(s,9H), 3.37(s,3H), 3.54(d,2H), 4.1–4.5(m,1H), 5.21(s,2H), 6.9–7.4(m,4H), 7.70(s,1H) |
| 661 | 0.97(s,3H), 1.5–1.9(m,2H), 1.61(s,9H), 3.35(s,3H), 3.52(d,2H), 4.1–4.4(m,1H), 4.19(s,2H), 6.8–7.3(m,4H), 7.56(s,1H) |
| 668 | 0.8–1.2(m,6H), 1.4–1.9(m,4H), 1.62(s,9H), 3.3–3.7(m,4H), 4.2–4.5(m,1H), 5.25(s,2H), 6.9–7.4(m,4H), 7.76(s,1H) |
| 671 | 0.8–1.1(m,6H), 1.4–1.9(m,4H), 1.61(s,9H), 3.3–3.6(m,4H), 4.1–4.5(m,1H), 4.20(s,2H), 6.8–7.4(m,4H), 7.62(s,1H) |
| 673 | 0.8–1.2(m,6H), 1.3–1.9(m,6H), 1.61(s,9H), 3.3–3.6(m,4H), 4.1–4.5(m,1H), 5.20(s,2H), 6.8–7.3(m,4H), 7.72(s,1H) |
| 787 | 1.02(t,6H), 1.59(s,9H), 2.4–2.9(m,6H), 3.98(t,2H), 4.18(s,2H), 6.8–7.3(m,4H), 7.58(s,1H) |
| 844 | 1.21(t,6H), 1.60(s,9H), 3.5–3.8(m,4H), 3.95(d,2H), 4.17(s,2H), 4.78(t,1H), 6.7–7.3(m,4H), 7.52(s,1H) |
| 508 | 1.20(t,3H), 1.33(d,3H), 1.62(s,9H), 2.22(s,3H), 3.39–3.78(m,4H), 4.27–4.77(m,1H), 5.18(s,2H), 6.78–7.29(m,3H), 7.71(s,1H) |

TABLE 3-continued

| Compound No. | $^1$H—NMR Data CDCl$_3$, δ (ppm) |
|---|---|
| 509 | 1.19(t,3H), 1.31(d,3H), 1.60(s,9H), 2.19(s,3H), 3.33-3.75(m,4H), 4.15(s,2H), 4.23-4.72(m,1H), 6.72-7.33(m,3H) 7.60(s,1H) |
| 515 | 1.17(t,3H), 1.35(d,3H), 1.61(s,9H), 3.36-3.80(m,4H), 4.25(s,2H), 4.32-4.77(m,1H), 6.73-7.49(m,4H), 7.68(s,1H), |
| 516 | 1.18(t,3H), 1.32(d,3H), 1.61(s,9H), 3.32-3.74(m,4H), 4.34-4.83(m,1H), 5.32(s,2H), 6.79-7.52(m,4H), 7.79(s,1H) |
| 857 | 1.61(s,9H), 4.36(s,2H), 6.70-6.95(m,2H), 7.63(s,1H), |
| 858 | 1.60(s,9H), 1.75(d,J=7 Hz,3H) 4.87(q,J=7 Hz,1H), 6.70(d,J=3 Hz,1H), 6.83(d,J=3 Hz, 1H), 7.62(s,1H) |
| 860 | 1.62(s,9H), 4.39(s,2H), 6.85(bs,2H), 7.62(s,1H) |
| 870 | 1.33(s,9H), 1.60(s,9H), 4.39(s,2H), 6.60(d, J=3 Hz,1H), 6.83(d,J=3 Hz,1H), 7.67(s,1H) |
| 872 | 1.32(s,9H), 1.61(s,9H), 2.14(s,3H),4.28(s,2H), 6.58(d,J=3 Hz, 1H) 6.74(d,J=3 Hz,2H) 7.64(s,1H) |
| 876 | 0.7-1.05(m,3H), 1.15-1.75(m,4H), 1.58(s,9H), 2.70(t,J=7 Hz,2H 4.38(s,2H), 6.53(d,J=3 Hz,1H) 6.81(d,J=3 Hz,1H) 7.66(s,1H) |
| 883 | 1.00-2.00(m,10H), 1.60(s,9H), 2.35-2.95(m,1H), 4.36(s,2H), 6.57 (d,J=3 Hz,1H), 6.81(d, J=3 Hz,1H) 7.62(s,1H) |
| 885 | 1.60(s,9H), 4.40(s,2H), 6.90-7.55(m,6H), 7.68(s,1H) |
| 890 | 1.58(s,9H, 4.09(s,2H), 4.33(s,2H), 6.56(d,J=4 Hz,1H), 6.71(d,J=4 Hz,1H), 7.00-7.35(m,3H), 7.58(s,1H) |
| 930 | 1.62(s,9H), 3.90(s,2H), 5.07(s,2H), 6.04(s,1H), 7.21(s,1H), 7.35(s,1H), 7.69(s,1H) |
| 963 | 0.80-1.10(m,3H), 1.15-1.90(m,4H), 1.59(s,9H), 2.59(t,J=7 Hz,2H), 4.35(s,2H), 7.25-7.50(m,2H), 7.88(s,1H), 8.46(bs,1H) |
| 998 | 1.00(t,J=7 Hz,3H), 1.50-2.05(m,2H), 1.62(s,9H), 2.12(s,3H), 4.11(s,2H), 4.22(t,J=7 Hz,2H), 6.69(d,J=9 Hz, 1H) 7.50-7.80(m,1H), 7.63(s,1H), 8.07(d,J=2 Hz,1H) |
| 999 | 1.00(t,J=7 Hz,3H) 1.50-2.05(m,2H), 1.62(s,9H), 4.24(t,J=7 Hz,2H), 5.26(s,2H), 6.75(d,J=9 Hz,1H), 7.69(d-d,J=9 Hz,2 Hz,1H), 7.90(s,1H), 8.22(d,J=2 Hz,1H) |
| 1010 | 1.63(s,9H), 2.02(s,3H), 5.09(s,2H), 5.34(s,2H), 6.75-7.80(m,6H), 7.78(s,1H), 8.21(d,J=2 Hz,1H), |
| 1027 | 1.62(s,9H), 4.16(s,2H), 6.75-7.70(m,8H), 7.82(s,1H), |
| 1028 | 1.61(s,9H), 2.11(s,3H), 4.10(s,2H), 6.65-7.61(m,8H) 7.66(s,1H) |
| 1029 | 1.61(s,9H), 4.13(s,2H), 6.72-7.66(m,7H), 7.75(s,1H), |
| 1004 | 0.80-2.06(m,7H), 1.61(s,9H), 2.00(s,3H), 4.28(t,J=6 Hz,2H), 5.06(s,2H), 6.71(d,J=9 Hz,1H), 7.58(d-d,J=9 Hz,2 Hz,1H) |
| 1094 | 7.71(S,1H) 8.14(d, J=2 Hz,1H), 1.60(s,9H), 5.35(s,2H), 7.03(s,1H), 7.30(s,1H), 7.66(s,1H) |
| 1097 | 1.62(s,9H), 4.38(s,2H), 6.82(d,J=4 Hz,1H), 6.91(d,J=4 Hz,1H) 7.60(s,1H) |

When the compounds according to the present invention are used for insecticidal, acaricidal, nematicidal and/or fungicidal agents for agricultural and horticultural uses or for expellents of ticks parasitic on animals, they are generally mixed with appropriate carriers, for instance, solid carriers such as clay, talc, bentonite or diatomaceous earth, or liquid carriers such as water, alcohols (e.g. methanol and ethanol), aromatic hydrocarbons (e.g. benzene, toluene and xylene), chlorinated hydrocarbons, ethers, ketones, esters (e.g. ethyl acetate), or acid amides (e.g. dimethylformamide). If desired, to these mixtures may be added emulsifier, dipersing agent, suspension agent, penetrating agent, spreader, stabilizer and the like to put them into practical uses in the form of liquid preparation, emulsifiable concentrate, wettable powder, dust, granule, flowable or the like. Moreover, the mixtures may be incorporated with other herbicides, various insecticides, fungicides, plant-growth regulating agents and/or synergists during preparation or application thereof, as necessary.

The amount of the compounds of the invention to be used as an active ingredient is suitably in the range of approximately 0.005 to 50 kg per hectare although it varies depending upon the place and the season where the compounds are applied, manner of application, diseases and insect pests to be applied, cultivated crops to be protected and the like.

In the following, there are shown formulation examples of fungicidal, insecticidal, acaricidal and/or nematicidal compositions and expellent compositions for ticks parasitic on animals, said compositions containing the compounds of the present invention as an active ingredient. These examples are only illustrative and not to restrict the invention. In the following examples, "part" means "part by weight".

| Formulation Example 1: Emulsifiable concentrates | |
|---|---|
| Active ingredient | 20 parts |
| Xylene | 55 parts |
| N,N—dimethylformamide | 20 parts |
| Solpol 2680 (trade name, a mixture of a non-ionic surface-active agent and an anionic surface-active agent manufactured by Toho Chemicals, Co., Ltd., Japan) | 5 parts |

The above components are mixed intimately together to form an emulsifiable concentrate. Upon use, the emulsifiable concentrate is diluted with water up to one fiftieth to one twenty thousandth in concentration and applied at a rate of 0.005 to 50 kg of the active ingredient per hectare.

| Formulation Example 2: Wettable powders | |
|---|---|
| Active ingredient | 25 parts |

-continued

| Formulation Example 2: Wettable powders | |
|---|---|
| Siegreit PFP (trade name, a mixture of kaolinite and sericite manufactured by Siegreit Mining Industries Co., Ltd.) | 66 parts |
| Solpol 5039 (trade name, an anionic surface-active agent manufactured by Toho Chemical Co., Ltd., Japan) | 4 parts |
| Carplex #80 (trade name, white carbon manufactured by Shionogi Seiyaku K.K., Japan) | 3 parts |
| Calcium lignin sulfonate | 2 parts |

The above components are homogeneously mixed together and ground to form a wettable powder. Upon use, the wettable powder is diluted with water up to one fiftieth to one twenty thousandth and applied at a rate of 0.005 to 50 kg of the active ingredient per hectare.

| Formulation Example 3: Oil solutions | |
|---|---|
| Active ingredient | 10 parts |
| methylcellosolve | 90 parts |

The above components are homogeneously mixed together to form an oil solution. Upon use, the oil solution is applied at a rate of 0.005 to 50 kg of the active ingredient per hectare.

| Formulation Example 4: Dusts | |
|---|---|
| Active ingredient | 3.0 parts |
| Carplex #80 (trade name, white carbon manufactured by Shionogi Seiyaku K.K., Japan) | 0.5 part |
| Clay | 95.0 parts |
| di-isopropyl phosphate | 1.5 parts |

The above components are homogeneously mixed together and ground to form a dust. Upon use, the dust is applied at a rate of 0.005 to 50 kg of the active ingredient per hectare.

| Formulation Example 5: Granules | |
|---|---|
| Active ingredient | 5 parts |
| Bentonite | 54 parts |
| Talc | 40 parts |
| Calcium lignin sulfonate | 1 part |

The above components are mixed intimately together and ground, incorporated with a small amount of water and mixed together with stirring. The resulting mixture is granulated by means of extrusion-granulator and dried to form granules. Upon use, the granule is applied at a rate of 0.005 to 50 kg of the active ingredient per hectare.

| Formulation Example 6: Flowables | |
|---|---|
| Active ingredient | 25 parts |
| Solpol 3353 (trade name, a non ionic surface-active agent manufactured by Toho Chemicals, Co., Ltd., Japan) | 10 parts |
| Runox 1000C (trade name, an anionic surface-active agent manufactured by Toho Chemicals, Co., Ltd., Japan) | 0.5 part |
| 1% aqueous solution of Xanthan gum (natural high-molecular compound) | 20 parts |

| Formulation Example 6: Flowables | |
|---|---|
| Water | 44.5 parts |

The above components except the active ingredient are uniformly mixed together to form a solution, and thereto is added the active ingredient. The resulting mixture is throughly stirred, wet-ground by means of sand mill to form a flowable. Upon use, the flowable is diluted up to one fiftieth to one twenty thousandth with water and applied at a rate of 0.005 to 50 kg of the active ingredient per hectare.

The compounds according to the present invention not only exhibit superior insecticidal action on hemiptera insect such as green rice leafhopper (*Nephotettix cincticeps*), lepidoptera insect such as diamondback moth (*Plutella xylostella*), Coleoptera and sanitary insect pests such as pale house mosquito (*Culex pipiens*), but are also useful for expelling mites parasitic on fruits and vegetables such as two-spotted spider mite (*Tetranychus urticae*), Kanzawa spider mite (*Tetranychus kanzawai*), Carmine mite (*Tetranychus cinnabarinus*), citrus red mite (*Panonychus citri*) and European red mite (*Panonychus ulmi*), as well as ticks parasitic on animals such as southern cattle tick (*Boophilus microplus*), cattle tick (*Boophilus annulatus*), galf coast tick (*Amblyomma maculatum*), brown-ear tick (*Rhipicephalus appendiculatus*) and (*Haemaphysalis longicornis*). The compounds of the present invention are also useful for controlling nematoda such as root-knot nematode (Meloidogyne sp.), root-lesion nematode (Pratylenchus sp.) and cyst nematode. The main features of the compounds of the present invention resides in that the compounds are useful for the prevention or control of blight (or disease) of fruits and vegetables such as powdery mildew, downy mildew, rust, rice blast disease (or rice blight) etc. in addition to having the above mentioned insecticidal, acaricidal and nematicidal actions. Accordingly, the compounds of the present invention are an excellent agricultural drug which enables control of pests and blight (or disease) simultaneously. Moreover, they are excellent as an expellent for ticks parasitic on animals such as domestic animals (e.g. cattle, horse, sheep and pig), domestic fowls, and other animals such as dog, cat, rabbit and the like.

The invention is further explained in detail by way of the following test examples.

TEST EXAMPLE 1

Insecticidal Test on Green Rice Leafhopper
(*Nephotettix cincticeps*)

Stems and leaves of paddy were immersed into a 1000 ppm aqueous emulsion which had been prepared by diluting with water an emulsifiable concentrate containing each compound of the invention for about 10 seconds, and then the stems and leaves were placed into a glass cylinder. After 10 adults of green rice leafhopper which would show resistance to organic phosphorus type insecticides were released, the glass cylinder was covered with a plastic lid having some pores and placed in a thermostatic chamber kept at 25° C. After 96 hours later, the mortality was calculated according to the following equation. Incidentally, the test was repeated twice for each compound. The results are shown in Table 4.

$$\text{Mortality (\%)} = \frac{\text{number of the insect killed}}{\text{number of the insect released}} \times 100$$

TEST EXAMPLE 2

Contact Insecticidal Test on 28-spotted Lady Beetle (*Henosepilachna vigintioctopunctata*)

A leaf of tomato was immersed for about 10 seconds in a 1000 ppm aqueous emulsion which had been prepared by diluting with water an emulsifiable concentrate containing each compound of the invention and then air-dried. The leaf thus treated was placed in a laboratory dish, into which 10 second inster 28-spotted lady beetle larvae were released. The dish was then fitted with a cap provided with pores and then placed in a thermostatic chamber kept at 25° C. The number of the larvae killed was checked after 96 hours and the mortality thereof was calculated according to the equation below. Incidentally, the test was repeated twice for each compound. The test results are shown in Table 4.

$$\text{Mortality (\%)} = \frac{\text{number of the insect killed}}{\text{number of the insect released}} \times 100$$

TEST EXAMPLE 3

Acaricidal Test on Kanzawa Spider Mite (*T. kanzawai*)

A leaf of kidney bean was cut into a round piece of 1.5 cm in diameter by a leaf punch, and then placed on a moistened filter paper on a styrol cup of 7 cm in diameter. Each piece of the leaf was inoculated with 10 Kanzawa Spider Mite nymphs. Half a day after the inoculation, each 2 ml of a 1000 ppm aqueous emulsion which had been prepared by diluting with water an emulsifiable concentrate containing each compound of the invention was applied to each styrol cup by means of a rotary spray tower. After 96 hours, the mortality of the nymph was determined according to the equation below. Incidentally, the test was repeated twice for each compound. The results are shown in Table 4.

$$\text{Mortality (\%)} = \frac{\text{number of the insect killed}}{\text{number of the insect released}} \times 100$$

TABLE 4

| Compound No. of the Present Invention | Green Rice Leafhopper (*Nephotettix cincticeps*) | 28-spotted Lady Beetle (*Henosepilachna vigintioctopunctata*) | Kanzawa Spider Mite (*T. Kanzawai*) |
|---|---|---|---|
| 5 | 100 | 100 | 100 |
| 7 | 100 | 100 | 100 |
| 15 | 100 | 100 | 100 |
| 16 | 100 | 100 | 100 |
| 17 | 100 | 100 | 100 |
| 44 | 100 | 100 | 100 |
| 45 | 100 | 100 | 100 |
| 68 | 100 | 100 | 100 |
| 71 | 100 | 100 | 100 |
| 81 | 100 | 100 | 100 |
| 87 | 100 | 100 | 100 |
| 281 | 100 | 100 | 100 |
| 291 | 100 | 100 | 100 |
| 302 | 100 | 100 | 100 |
| 310 | 100 | 100 | 100 |
| 369 | 100 | 100 | 100 |
| 402 | 100 | 100 | 100 |
| 403 | 100 | 100 | 100 |
| 413 | 100 | 100 | 100 |
| 415 | 100 | 100 | 100 |
| 421 | 100 | 100 | 100 |
| 424 | 100 | 100 | 100 |
| 663 | 100 | 100 | 100 |
| 502 | 100 | 100 | 100 |
| 504 | 100 | 100 | 100 |
| 508 | 100 | 100 | 100 |
| 511 | 100 | 100 | 100 |
| 513 | 100 | 100 | 100 |
| 517 | 100 | 100 | 100 |
| 521 | 100 | 100 | 100 |
| 524 | 100 | 100 | 100 |
| 527 | 100 | 100 | 100 |
| 531 | 100 | 100 | 100 |
| 533 | 100 | 100 | 100 |
| 551 | 100 | 100 | 100 |
| 552 | 100 | 100 | 100 |
| 553 | 100 | 100 | 100 |
| 579 | 100 | 100 | 100 |
| 581 | 100 | 100 | 100 |
| 582 | 100 | 100 | 100 |
| 611 | 100 | 100 | 100 |
| 612 | 100 | 100 | 100 |
| 615 | 100 | 100 | 100 |
| 616 | 100 | 100 | 100 |
| 637 | 100 | 100 | 100 |
| 639 | 100 | 100 | 100 |
| 659 | 100 | 100 | 100 |
| 661 | 100 | 100 | 100 |
| 664 | 100 | 100 | 100 |
| 667 | 100 | 100 | 100 |
| 668 | 100 | 100 | 100 |
| 671 | 100 | 100 | 100 |
| 673 | 100 | 100 | 100 |
| 675 | 100 | 100 | 100 |
| 838 | 100 | 100 | 100 |
| 843 | 100 | 100 | 100 |
| 844 | 100 | 100 | 100 |
| 857 | 100 | 100 | 100 |
| 858 | 100 | 100 | 100 |
| 860 | 100 | 100 | 100 |
| 870 | 100 | 100 | 100 |
| 872 | 100 | 100 | 100 |
| 876 | 100 | 100 | 100 |
| 883 | 100 | 100 | 100 |
| 885 | 100 | 100 | 100 |
| 898 | 100 | 100 | 100 |
| 929 | 100 | 100 | 100 |
| 930 | 100 | 100 | 100 |
| 951 | 100 | 100 | 100 |
| 963 | 100 | 100 | 100 |
| 964 | 100 | 100 | 100 |
| 997 | 100 | 100 | 100 |
| 998 | 100 | 100 | 100 |
| 999 | 100 | 100 | 100 |
| 1001 | 100 | 100 | 100 |
| 1003 | 100 | 100 | 100 |
| 1004 | 100 | 100 | 100 |
| 1007 | 100 | 100 | 100 |
| 1010 | 100 | 100 | 100 |
| 1011 | 100 | 100 | 100 |
| 1027 | 100 | 100 | 100 |
| 1028 | 100 | 100 | 100 |
| 1029 | 100 | 100 | 100 |
| 1041 | 100 | 100 | 100 |
| 1042 | 100 | 100 | 100 |
| 1055 | 100 | 100 | 100 |
| 1056 | 100 | 100 | 100 |
| 1058 | 100 | 100 | 100 |
| 1062 | 100 | 100 | 100 |
| 1063 | 100 | 100 | 100 |
| 1067 | 100 | 100 | 100 |
| 1081 | 100 | 100 | 100 |
| 1083 | 100 | 100 | 100 |
| 82 | 100 | 100 | 100 |
| 88 | 100 | 100 | 100 |
| 509 | 100 | 100 | 100 |
| 535 | 100 | 100 | 100 |

TABLE 4-continued

| Compound No. of the Present Invention | Green Rice Leafhopper (*Nephotettix cincticeps*) | 28-spotted Lady Beetle (*Henosepilachna vigintioctopunctata*) | Kanzawa Spider Mite (*T. Kanzawai*) |
|---|---|---|---|
| 538 | 100 | 100 | 100 |
| 554 | 100 | 100 | 100 |
| 555 | 100 | 100 | 100 |
| 787 | 100 | 100 | 100 |

TEST EXAMPLE 4

Insecticidal Test on Common Cutworm or Cluster Caterpillar (*Spodoptera litura*)

A leaf of cabbage was immersed in a 1000 ppm aqueous emulsion which had been prepared by diluting with water an emulsifiable concentrate containing each compound of the invention for about 10 seconds, and then air-dried. The leaf thus treated was placed in a laboratory dish, into which second instar common cutworm or cluster caterpillar (*Spodoptera litura*) larvae were released. The dish was fitted with a cap provided with some pores and then placed in a thermostatic chamber kept at 25° C. The mortality after 7 days was determined according to the equation below. Incidentally, the test was repeated twice for each compound.

$$\text{Mortality (\%)} = \frac{\text{number of the insect killed}}{\text{number of the insect released}} \times 100$$

As the results, the following compounds showed a mortality of 100%:

Compound Nos. 45, 403, 415, 424, 504, 513, 521, 533, 639, 667, 671, 857, 858, 860, 870, 872, 876, 883, 885, 963, 964, 997, 998, 999, 1001, 1003, 1004, 1007, 1010, 1011, 1041, 1042, 1055, 1056, 1058, 1062, 1063, 1081 and 1083.

TEST EXAMPLE 5

Nematicidal Test on Root-knot Nematode (*Meloidogyne sp.*)

Soil contaminated with root-knot nematode was placed in a styrol cup of 8 cm in diameter. A liquid containing 1000 ppm of an active ingredient was prepared by diluting an emulsifiable concentrate containing a compound of the present invention with water. The soil contaminated with nematode and placed in the styrol cup was drenched with each 50 ml of the resulting liquid. After 48 hours, a tomato seedling as an indicator was transplanted into the soil thus treated. Thirty days after the transplantation, the roots of the tomato were washed with water and the root-knot parasitism was checked by observation. Incidentally, the test was repeated twice for each compound. As a result, no root-knot parasitism was observed in the roots of the tomato treated with the following compounds; it was shown that these compounds exhibit a strong nematicidal activity:

Compound Nos. 895, 964, 999 and 1041.

TEST EXAMPLE 6

Test for Controlling Downy Mildew of Cucumber

Employing cucumbers (*Cucumis sativus* L.: variety Sagamihanjiro) which had been grown for 2 weeks, thereto was sprayed a solution of an emulsifiable concentrate according to the invention which had been adjusted to a predetermined concentration (1000 ppm) at the rate of 20 ml per pot. After each pot was placed for one day in a greenhouse, a suspension of spores of *Pseudoperonospora cubensis* (the concentration of the spores being such that 15 pieces of the spore can be observed by a 150 magnification microscope) was sprayed to the cucumbers for inoculation. The cucumbers to which the spores of *Pseudoperonospora cubensis* had been inoculated were left for 24 hours in a room kept at 25° C. with a relative humidity of 100% and then transported to a greenhouse for observation of disease appearance. Seven days after the inoculation, the percentages of the disease appearance were measured. As the results, no disease appearance was observed at all with respect to the following compounds:

Compound Nos. 5, 81, 87, 281, 392, 415, 421, 424, 511, 513, 517, 521, 524, 527, 531, 533, 552, 553, 581, 582, 616, 637, 639, 659, 661, 663, 664, 667, 668, 671, 843, 885, 951, 964, 997, 998, 999, 1010, 1011 and 1041.

TEST EXAMPLE 7

Test for Controlling Powdery Mildew of Cucumber

Employing cucumbers (*Cucumis sativus* L.: variety Sagamihanjiro) which had been grown in pots for 2 weeks, thereto was sprayed a solution of an emulsifiable concentrate containing a compound of the present invention and which had been adjusted to a predetermined concentration (1000 ppm) at the rate of 20 ml per pot. After each pot was placed for one day in a greenhouse, a suspension of spores of *Sphaerotheca fuliginea* (the concentration of the spores being such that 25 pieces of the spores can be observed by a 150 magnification microscope) was sprayed to the cucumbers for inoculation. The cucumbers were placed in a greenhouse at 25°–30° C. for observation of disease appearance. Ten days after the inoculation, the percentages of the disease appearance were measured and evaluated. As the results, no disease appearance was observed at all with respect to the following compounds:

Compound Nos. 17, 68, 71, 81, 87, 281, 415, 421, 504, 511, 513, 517, 521, 524, 527, 531, 552, 581, 582, 616, 637, 639, 659, 664 843, 844, 872, 885, 898, 951, 963, 964, 997, 998, 999, 1010, 1011, 1041 and 1042.

TEST EXAMPLE 8

Test for Controlling Leaf Rust of Wheat

To wheats (Norin No. 61, third to fourth leaf-stage) which had been grown in pots of 9 cm in diameter was sprayed a solution of an emulsifiable concentrate containing a compound of the invention and which had been adjusted to a concentration of 1000 ppm at the rate of 20 ml per pot by means of a spray gun. The next day, thereto was sprayed a suspension of Uredospore of *Puccinia triticina* (the concentration of the suspension being such that 30 pieces of the spores can be observed by a 150 magnification microscope). Each pot was placed in an inoculation box kept at 25° C. with a relative humidity of not lower than 95% for one day and then allowed to stand at room temperature. Ten days after the inoculation, the disease area thus formed was measured and the protective value of each compound was calculated according to the following equation:

Protective value (%) =

$$\left(1 - \frac{\text{disease area in a treated plot}}{\text{disease area in a non-treated plot}}\right) \times 100$$

As the results, the following compounds showed a protective value of 100%:

Compound Nos. 424, 504, 517, 533, 637, 885, 951, 964, 997, 998, 999, 1010, 1011, 1041 and 1042.

TEST EXAMPLE 9

Test for Controlling Rice Blight

To rice plants (Nihonbare, third to fourth leaf-stage) which had been grown in pots of 9 cm in diameter was sprayed a solution of an emulsifiable concentrate which contains a compound of the present invention in the concentration of 1000 ppm at the rate of 20 ml per pot by means of a spray gun. The next day, a suspension of spores of *Pyricularia oryzae* (concentration of the suspension being such that 40 pieces of the spore can be observed by a 150 magnification microscope) was sprayed to the rice plants. Each pot was placed in an inoculation box kept at 25° with a relative humidity of not lower than 95% for one day and thereafter allowed to stand at room temperature. Seven days after the inoculation, the number of the disease appearance formed was measured and the protective value was calculated according to the following equation:

$$\text{Protective value} = \left(1 - \frac{\text{number of disease appearance in a treated plot}}{\text{number of disease appearance in a non-treated plot}}\right) \times 100$$

As the results, the following compounds showed 100% in protective value:

Compound Nos. 16, 17, 281, 517, 611, 885, 951, 964, 997, 998, 999, 1010, 1011, 1029 and 1041.

TEST EXAMPLE 10

Test for Controlling Downy Mildew of Cucumber (Low Concentration Test)

Test was conducted in accordance with Test Example 6 except that the concentration each of the present compound and a control compound was changed to 500, 100 and 50 ppm. The protective value was calculated according to the following equation:

$$\text{Protective value} = \left(1 - \frac{\text{disease area in a treated plot}}{\text{disease area in a non-treated plot}}\right) \times 100$$

The results are shown in Table 5. From the results, it can be seen that the present compounds exhibit much higher fungicidal activity than the known control compounds.

TEST EXAMPLE 11

Test for Controlling Powdery Mildew of Cucumber (Low Concentration Test)

Test was conducted in accordance with Test Example 7 except that the concentration each of the present compound and a control compound was changed to 500, 100 and 50 ppm. The protective value was calculated according to the following equation:

$$\text{Protective value} = \left(1 - \frac{\text{disease area in a treated plot}}{\text{disease area in a non-treated plot}}\right) \times 100$$

The results are shown in Table 5. From the results, it can be seen that the present compounds exhibit much higher fungicidal activity than the known control compounds.

TEST EXAMPLE 12

Test for Controlling Leaf Rust of Wheat (Low Concentration Test)

Test was conducted in accordance with Test Example 8 except that the concentration each of the present compound and a control compound was changed to 500, 100 and 50 ppm. The protective value was calculated according to the following equation:

$$\text{Protective value} = \left(1 - \frac{\text{number of disease appearance in a treated plot}}{\text{number of disease appearance in a non-treated plot}}\right) \times 100$$

The results are shown in Table 5. From the results, it can be seen that the present compounds exhibit much higher fungicidal activity than the known control compounds.

TEST EXAMPLE 13

Test for Controlling Rice Blight (Low Concentration Test)

Test was conducted in accordance with Test Example 9 except that the concentration each of the present compound and a control compound was changed to 500, 100 and 50 ppm. The protective value was calculated according to the following equation:

$$\text{Protective value} = \left(1 - \frac{\text{number of disease appearance in a treated plot}}{\text{number of disease appearance in a non-treated plot}}\right) \times 100$$

The results are shown in Table 5. From the results, it can be seen that the present compounds exhibit much higher fungicidal activity than the known control compounds.

(a) a compound described in European Laid-open Patent Application No. 0134439 Gazette.

(b) a compound encompassed by the general formula described in European Laid-open Patent Application No. 0088384 Gazette.

As the results of Test Examples 10 through 13, it was shown that the present compounds, compared with the control compounds, are not only markedly increased in activity for controlling each blight but also have a wider spectrum and that the present compounds have an excellent fungicidal activity which enables simultaneous control of downy mildew and powdery mildew of vegetables or powdery mildew and red rust of wheat.

TABLE 5

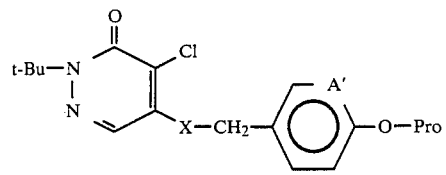

| Protective value (%) | ppm | A' = N, X = S Present Compound No. 997 | A' = N, X = O Present Compound No. 999 | A' = CH, X = S Reference Compound 1[a] | A' = CH, X = O Reference Compound 2[b] |
|---|---|---|---|---|---|
| Downy mildew of cucumber | 500 | 100 | 100 | 0 | 0 |
|  | 100 | 100 | 80 | 0 | 0 |
|  | 50 | 80 | 50 | 0 | 0 |
| Powdery mildew of cucumber | 500 | 100 | 100 | 0 | 100 |
|  | 100 | 100 | 100 | 0 | 70 |
|  | 50 | 60 | 80 | 0 | 30 |
| Leaf rust of wheat | 500 | 100 | 100 | 0 | 80 |
|  | 100 | 100 | 100 | 0 | 70 |
|  | 50 | 100 | 80 | 0 | 0 |
| Rice Blast (*Pyricularia oryze*) of rice plant | 500 | 100 | 100 | 80 | 0 |
|  | 100 | 100 | 80 | 0 | 0 |
|  | 50 | 70 | 40 | 0 | 0 |

TEST EXAMPLE 14

Insecticidal Test on Green Rice Leafhopper (*Nephotettix cincticeps*) (Low Concentration Test)

Test was conducted in accordance with Test Example 1 except that the concentration each of the present compound and a control compound was changed to 10 ppm. The results are shown in Table 6.

As the results, it was shown that the present compounds exhibit higher insecticidal activity compared with the known control compounds.

(a) a compound encompassed by the general formula described in European Laid-open Patent Application No. 0088384 Gazette.

Control compound A:

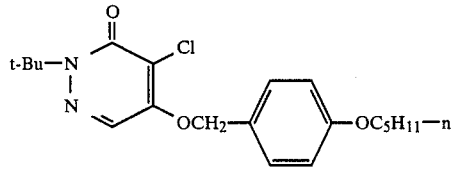

(b) a compound described in European Laid-open Patent Application No. 0134439 Gazette.

Control compound B:

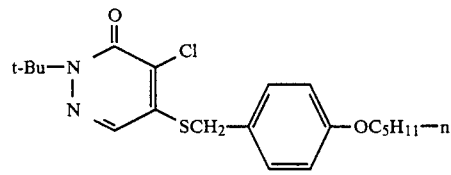

Control compound C:

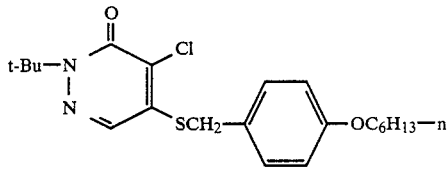

(c) Compound No. of the present invention

TABLE 6

| Compound No. | Green Rice Leafhopper mortality (%) | Compound No. | Green Rice Leafhopper mortality (%) |
|---|---|---|---|
| Reference Compound[a] A | 55 | 511[c] | 100 |
| Reference Compound[b] B | 30 | 521[c] | 100 |
| Reference Compound[b] C | 25 | 527[c] | 100 |
| 68[c] | 100 | 611[c] | 100 |
| 81[c] | 100 | 616[c] | 100 |

TEST EXAMPLE 15

Acaricidal Test on Kanzawa Spider Mite (*T. kanzawai*) (Low Concentration Test)

Test was conducted in accordance with Test Example 3 except that the concentration each of the present compound and a control compound was changed to 100 ppm. The results are shown in Table 7.

As the results, it was shown that the present compounds exhibit higher acaricidal activity compared with the known control compounds.

TABLE 7

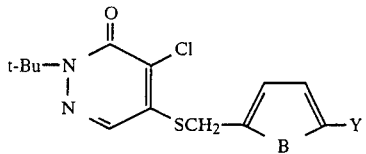

| | Compound | | | |
|---|---|---|---|---|
| | Present Compound B | | Reference Compound[a] | |
| | S | | CH=CH | |
| | | Y | | |
| Activity | Cl (No. 857) | Br (No. 860) | Cl | Br |
| Kanzawa Spider Mite mortality (%) | 100 | 100 | 50 | 50 |

[a] The compound described in European Laid-open Patent No. 0134439

TEST EXAMPLE 16

Acaricidal Test on Two-Spotted Spider Mite (*Tetranychus urticae*) (Low Concentration Test)

Test was conducted in accordance with Test Example 3 except that two-spotted spider mite adults were used and that the concentration each of the present compound and a control compound was changed to 100 ppm and 10 ppm. The results are shown in Table 8. As the results, it was shown that the present compounds exhibit much higher acaricidal activity compared with the known control compounds.

TABLE 8

| Reference Compound No. | Two-spotted spider mite mortality (%) | | Present Compound No. | Two-spotted spider mite mortality (%) | |
|---|---|---|---|---|---|
| | 100 ppm | 10 ppm | | 100 ppm | 10 ppm |
| B[a] | 95 | 40 | 504 | 100 | 100 |
| C[a] | 100 | 55 | 521 | 100 | 100 |
| D[a] | 95 | 35 | 612 | 100 | 100 |
| | | | 844 | 100 | 100 |

[a] The compound described in European Laid-open Patent No. 0134439

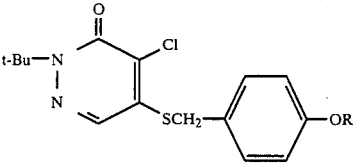

Reference Compound B: R′ = n-$C_5H_{11}$
Reference Compound C: R′ = n-$C_6H_{13}$
Reference Compound D: R′ = n-$C_4H_9$

TEST EXAMPLE 17

Residual Action Test on Two-Spotted Spider Mite (*Tetranychus urticae*)

Emulsifiable concentrates each containing a present compound or a control compound were diluted with water to give a drug solution having a concentration of 100 ppm. The drug solution was sprayed onto an eggplant in the sixth leaf-stage which had been grown in a 1/5000 are pot until the eggplant was drenched therewith. After air-drying, the pot was kept in a greenhouse. Seven days after and twenty eight days after the spraying, a leaf of the eggplant was cut into a round piece of 1.5 cm in diameter by a leaf punch and then placed on a moistened filter paper put on a styrol cup of 7 cm. in diameter. Each piece of the leaf was inoculated with 10 Two-spotted spider mite nymphs. The styrol cup was placed in a thermostatic chamber kept at 25° C. After 96 hours, the mortality of the nymph was checked. The results are shown in Table 9.

As the results, it was shown that the present compounds exhibit superior residual action to the known control compounds.

TABLE 9

| Compound No. | Two spotted spider mite aftereffective mortality (%) | | Compound No. | Two spotted spider mite aftereffective mortality (%) | |
|---|---|---|---|---|---|
| | after 7 days | after 28 days | | after 7 days | after 28 days |
| Reference Compound[a] B | 100 | 0 | 513[b] | 100 | 100 |
| Reference Compound[a] C | 100 | 0 | 521[b] | 100 | 100 |
| Reference Compound[a] D | 100 | 0 | 612[b] | 100 | 100 |
| 504[b] | 100 | 100 | 661[b] | 100 | 100 |

[a] The compound described in European Laid-Open Patent No. 0134439
[b] The compound No. of the present invention

TEST EXAMPLE 18

Nematicidal Test on Root-Knot Nematode (Meloidogyne sp.)

Soil contaminated with root-knot nematode was placed in a 1/10000 are pot. The present compound was formulated into a 5% dust according to Formulation Example 4, and 300 mg of the dust per pot was intimately mixed with the soil in the pot. The amount of the present compound in the soil corresponds to 30 kg of the compound per hectare. After 48 hours, a tomato seedling as an indicator was transplanted into the soil and kept in a greenhouse. Thirty days after the transplantation, the roots of the tomato were washed with water, and the root-knot parasitism was checked by observation and evaluated according to the following rating:

Rating of root-knot parasitism
0: no root-knot observed at all
1: a few root-knots observed
2: a medium number of root-knots observed
3: many root-knots observed
4: considerably many root-knots observed The results are shown in Table 10

TABLE 10

| Compound No. | Root-knot parasitism | Compound No. | Root-knot parasitism |
|---|---|---|---|
| Reference Compound[a] B | 2 | 81[b] | 0 |
| Reference Compound[a] C | 2 | 504[b] | 0 |
| Reference Compound[a] D | 3 | 513[b] | 0 |
| 7[b] | 0 | 533[b] | 0 |
| 15[b] | 0 | 582[b] | 0 |
| 45[b] | 0 | 1072[b] | 0 |
| 68[b] | 0 | 1073[b] | 0 |

[a] The compound described in European Laid-open Patent No. 0134439
[b] The compound No. of the present invention

What is claimed is:
1. A 3(2H)-pyridazinone of the formula:

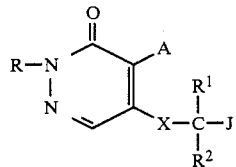

wherein
R represents an alkyl having 2 to 4 carbon atoms,
A represents an alkyl having 1 to 6 carbon atoms or a halogen atom,
X represents oxygen atom or sulfur atom,
$R^1$ and $R^2$ independently of one another represent hydrogen atom or an alkyl having 1 to 3 carbon atoms,
J respresents a radical of the formula:

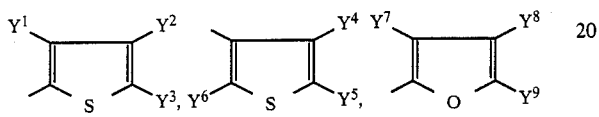

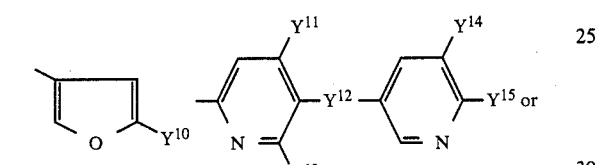

wherein
$Y^1$ represents a hydrogen atom, a chlorine atom or a bromine atom,
$Y^2$ represents a hydrogen atom, a halogen atom or an alkoxy having 1 to 4 carbon atoms,
$Y^3$ represents a hydrogen atom, a halogen atom, an alkyl having 1 to 6 carbon atoms, an alkoxy having 1 to 4 carbon atoms, a cyclohexyl, a haloalkylthio having 1 to 3 carbon atoms, a cyano, a nitro, a cyclohexyloxy, or a radical of the formula:

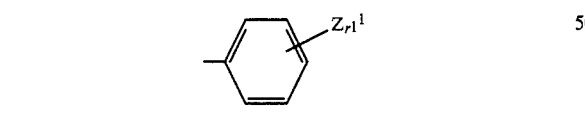

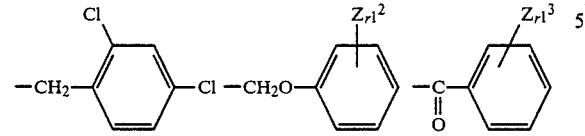

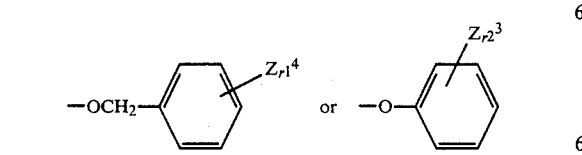

wherein
$Z^1$ represents a halogen atom,
$Z^2$ represents an alkyl having a 1 to 3 carbon atoms,
$Z^3$ represents a halogen atom or a haloalkyl having 1 to 3 carbon atoms
$Z^4$ represents a halogen atom or an alkyl having 1 to 3 carbon atoms,
$r^1$ is 1,
$r^2$ is 1 or 2, when $r^2$ is 2, $Z^3$s are different,
$Y^4$ represents a hydrogen atom, a chlorine atom or a bromine atom,
$Y^5$ represents a hydrogen atom, a halogen atom, an alkyl having 1 to 6 carbon atoms, an alkoxy having 1 to 4 carbon atoms, an alkoxycarbonyl having 1 to 4 carbon atoms, an alkylthio having 1 to 4 carbon atoms, or a radical of the formula:

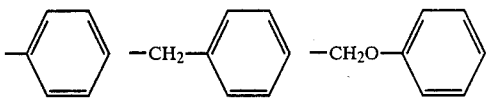

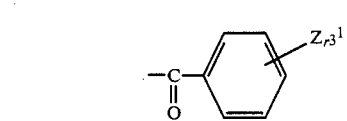

wherein
$r^3$ is 0 or 1,
$Y^6$ represents a hydrogen atom, a cholorine atom, a bromine atom or a cyclohexyl,
$Y^7$ represents a hydrogen atom, an alkoxy having 1 to 3 carbon atoms or an alkyl having 1 to 4 carbon atoms,
$Y^8$ represents a hydrogen atom, a chlorine atom, a bromine atom or an alkyl having 1 to 4 carbon atoms,
$Y^9$ represents a hydrogen atom, a halogen atom, an alkyl having 1 to 6 carbon atoms, a haloalkyl having 1 to 3 carbon atoms, a nitro, or a radical of the formula:

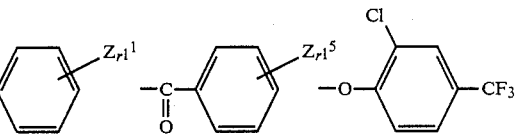

wherein
$Z^5$ represents a haloalkyl having 1 to 3 carbon atoms,
$Y^{10}$ represents an alkyl having 1 to 4 carbon atoms or a radical of the formula:

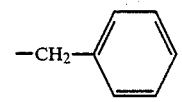

$Y^{11}$ represents a hydrogen atom, an alkyl having 1 to 4 carbon atoms or dimethylamino,
$Y^{12}$ represents a hydrogen atom, a halogen atom, an alkoxy having 1 to 3 carbon atoms, an alkyl having 1 to 6 carbon atoms, a haloalkyl having 1 to 3 carbon atoms, trimethylsilyl, an alkenyloxy having 3 to 4 carbon atoms, a haloalkoxy having 1 to 4 carbon atoms, or a radical of the formula:

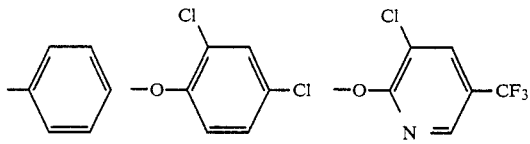

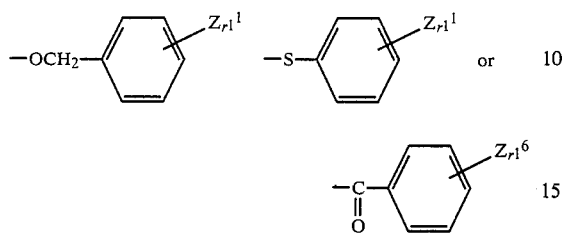    or

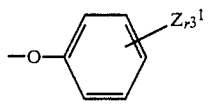

wherein
$Z^6$ represents a halogen atom or trifluoromethyl,
$Y^{13}$ represents a hydrogen atom, an alkyl having 1 to 4 carbon atoms or a radical of the formula:

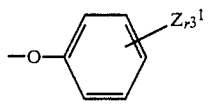

wherein
$Y^{14}$ represents a hydrogen atom, a halogen atom, or an alkoxycarbonyl having 1 to 4 carbon atoms,
$Y^{15}$ represents a hydrogen atom, a halogen atom, an alkyl having 1 to 6 carbon atoms, an alkoxy having 1 to 6 carbon atoms, a cycloalkyl having 3 to 6 carbon atoms, a cycloalkyloxy having 3 to 6 carbon atoms, a haloalkyl having 1 to 3 carbon atoms, a haloalkyloxy having 1 to 6 carbon atoms, an alkenyloxy having 3 to 4 carbon atoms, an alkylthio having 1 to 4 carbon atoms, an alkoxycarbonyl having 1 to 4 carbon atoms, or a radical of the formula:

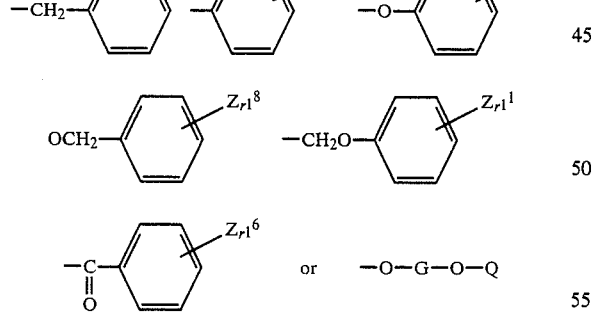    or   —O—G—O—Q wherein
$Z^7$ represents a halogen atom, trifluoromethyl, or an alkoxy having 1 to 3 carbon atoms,
$Z^8$ represents a halogen atom, an alkyl having 1 to 3 carbon atoms or cyclohexyl, $r^4$ is 1 or 2, when $r^4$ is 2, $Z^7$s are different from each other,
G represents a straight or branched chain alkylene having 2 to 3 carbon atoms,
Q represents am alkyl having 1 to 4 carbon atoms, and
$Y^{16}$ represents a hydrogen atom.

2. A compound according to claim 1 of the formula:

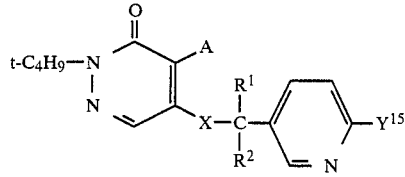

wherein
A represents a halogen atom or methyl,
X represents an oxygen or sulfur atom,
$R^1$ represents a hydrogen atom,
$R^2$ represents a hydrogen atom or methyl, and
$Y^{15}$ represents a straight or branched chain alkoxy having 1 to 6 carbon atoms, a straight or branched chain haloalkyloxy having 1 to 5 carbon atoms or a radical of the formula

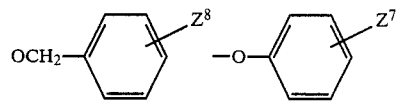

or —O—G—O—Q
wherein,
$Z^7$ and $Z^8$ represent a halogen atom, and G and Q have the same meanings as those given in claim 1.

3. A compound according to claim 1 of the formula:

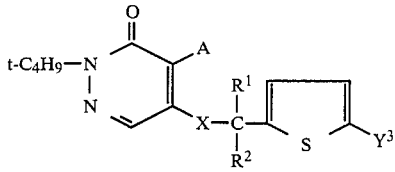

wherein
A represents a halogen atom or methyl,
X represents an oxygen or sulfur atom,
$R^1$ represents a hydrogen atom,
$R^2$ represents a hydrogen atom or methyl and
$Y^3$ represents a straight or branched chain alkyl having 1 to 6 carbon atoms or an alkoxy having 1 to 4 carbon atoms.

4. Insecticidal, acaricidal, nematicidal and fungicidal compositions for agricultural and horticultural uses, and expellent compositions for ticks parasitic on animals, which comprise an effective amount of the compound of claim 1; together with a suitable carrier and a diluent.

* * * * *